US008877449B2

(12) United States Patent
Ono et al.

(10) Patent No.: US 8,877,449 B2
(45) Date of Patent: Nov. 4, 2014

(54) METHOD FOR OBTAINING PANCREATIC PROGENITOR CELL USING NEPH3

(75) Inventors: Yuichi Ono, Hyogo (JP); Tomoya Nakatani, Hyogo (JP); Yasuko Nakagawa, Hyogo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 117 days.

(21) Appl. No.: 13/141,063

(22) PCT Filed: Dec. 18, 2009

(86) PCT No.: PCT/JP2009/071089
§ 371 (c)(1), (2), (4) Date: Jun. 20, 2011

(87) PCT Pub. No.: WO2010/073972
PCT Pub. Date: Jul. 1, 2010

(65) Prior Publication Data

US 2011/0256548 A1 Oct. 20, 2011

(30) Foreign Application Priority Data

Dec. 22, 2008 (JP) ................................ 2008-326401
Feb. 24, 2009 (JP) ................................ 2009-040667

(51) Int. Cl.
*G01N 33/53* (2006.01)
*G01N 33/68* (2006.01)
*C07K 14/47* (2006.01)
*C12N 5/071* (2010.01)

(52) U.S. Cl.
CPC .................................... *C12N 5/0678* (2013.01)
USPC ......................... 435/7.1; 435/7.21; 530/387.9

(58) Field of Classification Search
None
See application file for complete search history.

(56) References Cited

U.S. PATENT DOCUMENTS 7,622,270 B2 * 11/2009 Nakagawa et al. .......... 435/7.21
8,425,878 B2 * 4/2013 Eizirik et al. .................. 424/9.1
2007/0122882 A1 5/2007 Ono et al.
2010/0203570 A1 8/2010 Ono et al.
2010/0303771 A1 12/2010 Ono et al.
2011/0201003 A1 8/2011 Ono et al.

FOREIGN PATENT DOCUMENTS

EP 1561814 8/2005
WO WO 2004/038018 A1 5/2004
WO WO 2008/096817 A1 8/2008

OTHER PUBLICATIONS

Sun et al Genomics, 2003, v.82,pp. 130-142.*
Translation of the International Preliminary Report on Patentability for PCT/JP2009/071089 mailed Jul. 14, 2011, 8 pgs.
Copy of International Search Report for PCT/JP2009/071089, 2 pages, dated Feb. 9, 2010.
European Search Report for European application No. 09834773.5, Jan. 22, 2013.
Minaki et al., "Identification of a novel transcriptional corepressor, Corl2, as a cerebellar Purkinje cell-selective marker" Gene Expr Patterns, 2008, 8(6):418-23.
Zhou et al., "A multipotent progenitor domain guides pancreatic organogenesis" Dev Cell,, 2007, 13(1):103-14.
Holland, A., et al., "Conditional Expression Demonstrates the Role of the Homeodomain Transcription Factor Pdx1 in Maintenance and Regeneration of β-Cells in the Adult Pancreas," *Diabetes*, vol. 54(9), pp. 2586-2595 (Sep. 2005).
Kroon, E., et al., "Pancreatic endoderm derived from human embryonic stem cells generates glucose-responsive insulin-secreting cells in vivo," *Nature Biotechnology*, vol. 26(4), pp. 443-452 (Apr. 2008).
Rinta-Valkama, J., et al., "Podocyte-associated proteins FAT, alpha-actinin-4 and filtrin are expressed in Langerhans islets of the pancreas," *Mol Cell Biochem*, vol. 294(1-2), pp. 117-125 (Jan. 2007, Epub Jul. 14, 2006).
Suen, P.M., et al., "PDZ-domain containing-2 (PDZD2) is a novel factor that affects the growth and differentiation of human fetal pancreatic progenitor cells," *Int J Biochem Cell Biol.*, vol. 40(4), pp. 789-803 (2008, Epub Oct. 24, 2007).
Sun, C., et al., "*Kirrel2*, a novel immunoglobulin superfamily gene expressed primarily in β cells of the pancreatic islets," *Genomics*, vol. 82(2), pp. 130-142 (Aug. 2003).
Examination Report in EP App. Ser. No. 09834773.5, dated Dec. 3, 2013, 4 pages.
Office Action in JP App. Ser. No. 2010-544028, dated Jan. 14, 2014, 9 pages. (with English translation).
Response to Official Communication in EP App. Ser. No. 09834773.5, dated Feb. 24, 2014, 4 pages.
Response to Official Communication in EP App. Ser. No. 09834773.5, dated Aug. 14, 2013, 6 pages.
Written Argument and Amendment in JP App. Ser. No. 2010-544028, dated Feb. 21, 2014, 19 pages. (with English translation).

* cited by examiner

*Primary Examiner* — Michail Belyavskyi
(74) *Attorney, Agent, or Firm* — Fish & Richardson P.C.

(57) ABSTRACT

The present invention provides markers that can selectively distinguish pancreatic progenitor cells. The present invention also provides methods for distinguishing pancreatic progenitor cells by using the markers as an indicator, and reagents to be used in the methods.

The present inventors successfully identified the surface marker Nephrin-like 3 (Neph3) which is specifically expressed in pancreatic progenitor cells, and isolated pancreatic progenitor cells using the marker as an indicator or such. Viable pancreatic progenitor cells can be selected by using Neph3 as an indicator without using translated products and transcripts of any foreign genes. The marker is useful in preparing and identifying pancreatic progenitor cells which are applied to regenerative medicine or such for treatment of pancreatic diseases.

23 Claims, 6 Drawing Sheets

```
                              SEQUENCE LISTING


<160> NUMBER OF SEQ ID NOS: 28

<210> SEQ ID NO 1
<211> LENGTH: 2876
<212> TYPE: DNA
<213> ORGANISM: Mus musculus
<220> FEATURE:
<221> NAME/KEY: CDS
<222> LOCATION: (178)..(2277)

<400> SEQUENCE: 1

gatgagccag atttcgggga ctctgggcca gacataaaat cttccagccc ggagagaatt      60

gtgtgcagag aggggctcca gtccagcgtg gtgtgagagg cgtgctatca agaaagaagt     120

tggaggggaa ccagtgcaac cctaactcta cgagatcttg ggtacacac actcggg        177

atg ctg gcc tcc gcc ctc ctc gtt ttc ctt tgc tgt ttc aaa gga cat       225
Met Leu Ala Ser Ala Leu Leu Val Phe Leu Cys Cys Phe Lys Gly His
1               5                   10                  15

gca ggc tca tcg ccc cat ttc cta caa cag cca gag gac atg gtg gtg       273
Ala Gly Ser Ser Pro His Phe Leu Gln Gln Pro Glu Asp Met Val Val
            20                  25                  30

ctg ttg ggg gag gaa gcc cgg ctg ccc tgc gct ctg ggc gcg tac agg       321
Leu Leu Gly Glu Glu Ala Arg Leu Pro Cys Ala Leu Gly Ala Tyr Arg
        35                  40                  45

ggg ctc gtg cag tgg act aag gat ggg ctg gct cta ggg ggc gaa aga       369
Gly Leu Val Gln Trp Thr Lys Asp Gly Leu Ala Leu Gly Gly Glu Arg
    50                  55                  60

gac ctt cca ggg tgg tcc cgg tac tgg ata tcg ggg aat tca gcc agt       417
Asp Leu Pro Gly Trp Ser Arg Tyr Trp Ile Ser Gly Asn Ser Ala Ser
65                  70                  75                  80

ggc cag cat gac ctc cac att aag cct gtg gaa ttg gaa gat gag gca       465
Gly Gln His Asp Leu His Ile Lys Pro Val Glu Leu Glu Asp Glu Ala
                85                  90                  95

tcg tat gag tgc cag gct tcg caa gca ggt ctc cga tca cga cca gcc       513
Ser Tyr Glu Cys Gln Ala Ser Gln Ala Gly Leu Arg Ser Arg Pro Ala
            100                 105                 110

caa ctg cac gtg atg gtc ccc cca gaa gct ccc cag gta cta ggc ggc       561
Gln Leu His Val Met Val Pro Pro Glu Ala Pro Gln Val Leu Gly Gly
        115                 120                 125

ccc tct gtg tct ctg gtt gct gga gtt cct gga aat ctg acc tgt cgg       609
Pro Ser Val Ser Leu Val Ala Gly Val Pro Gly Asn Leu Thr Cys Arg
    130                 135                 140

agt cgt ggg gat tcc cga cct gcc cct gaa cta ctg tgg ttc cga gat       657
Ser Arg Gly Asp Ser Arg Pro Ala Pro Glu Leu Leu Trp Phe Arg Asp
145                 150                 155                 160

ggg atc cgg ctg gat gcg agc agc ttc cac cag acc acg ctg aag gac       705
Gly Ile Arg Leu Asp Ala Ser Ser Phe His Gln Thr Thr Leu Lys Asp
                165                 170                 175

aag gcc act gga aca gtg gaa aac acc tta ttc ctg acc cct tcc agt       753
Lys Ala Thr Gly Thr Val Glu Asn Thr Leu Phe Leu Thr Pro Ser Ser
            180                 185                 190

cat gat gat ggc gcc acc ttg atc tgc aga gcg cga agc cag gcc ctg       801
```

-continued

```
His Asp Asp Gly Ala Thr Leu Ile Cys Arg Ala Arg Ser Gln Ala Leu
        195                 200                 205

ccc aca ggg agg gac aca gct gtt aca ctg agc ctt cag tat ccc cca      849
Pro Thr Gly Arg Asp Thr Ala Val Thr Leu Ser Leu Gln Tyr Pro Pro
    210                 215                 220

atg gtg act ctg tct gct gag ccc cag act gtg cag gag gga gag aag      897
Met Val Thr Leu Ser Ala Glu Pro Gln Thr Val Gln Glu Gly Glu Lys
225                 230                 235                 240

gtg act ttc ctg tgt caa gcc act gcc cag cct cct gtc act ggc tac      945
Val Thr Phe Leu Cys Gln Ala Thr Ala Gln Pro Pro Val Thr Gly Tyr
                245                 250                 255

agg tgg gcg aag ggg gga tcc ccg gtg ctc ggg gca cgt ggg cca agg      993
Arg Trp Ala Lys Gly Gly Ser Pro Val Leu Gly Ala Arg Gly Pro Arg
            260                 265                 270

ttg gag gtc gtt gca gat gcc act ttc ctg act gag ccg gtg tcc tgc     1041
Leu Glu Val Val Ala Asp Ala Thr Phe Leu Thr Glu Pro Val Ser Cys
        275                 280                 285

gag gtc agc aac gcg gtc gga agc gcc aac cgc agc acg gcg ctg gaa     1089
Glu Val Ser Asn Ala Val Gly Ser Ala Asn Arg Ser Thr Ala Leu Glu
    290                 295                 300

gtg ttg tat gga ccc att ctg cag gca aaa cct aag tcc gtg tcc gtg     1137
Val Leu Tyr Gly Pro Ile Leu Gln Ala Lys Pro Lys Ser Val Ser Val
305                 310                 315                 320

gac gtg ggg aaa gat gcc tcc ttc agc tgt gtc tgg cgc ggg aac cca     1185
Asp Val Gly Lys Asp Ala Ser Phe Ser Cys Val Trp Arg Gly Asn Pro
                325                 330                 335

ctt cca cgg ata acc tgg acc cgc atg ggt ggc tct cag gtg ctg agc     1233
Leu Pro Arg Ile Thr Trp Thr Arg Met Gly Gly Ser Gln Val Leu Ser
            340                 345                 350

tcc ggg ccc acg ctg cgg ctt ccg tcc gtg gca ctg gag gat gcg ggc     1281
Ser Gly Pro Thr Leu Arg Leu Pro Ser Val Ala Leu Glu Asp Ala Gly
        355                 360                 365

gac tat gta tgc agg gct gag ccg agg aga acg ggt ctg gga ggc ggc     1329
Asp Tyr Val Cys Arg Ala Glu Pro Arg Arg Thr Gly Leu Gly Gly Gly
    370                 375                 380

aaa gcg cag gcg agg ctg act gtg aac gca ccc cct gta gtg aca gcc     1377
Lys Ala Gln Ala Arg Leu Thr Val Asn Ala Pro Pro Val Val Thr Ala
385                 390                 395                 400

ctg caa cct gca cca gcc ttt ctg agg ggt cct gct cgc ctc cag tgt     1425
Leu Gln Pro Ala Pro Ala Phe Leu Arg Gly Pro Ala Arg Leu Gln Cys
                405                 410                 415

gtg gtg ttt gcc tcc cct gcc cca gac tcg gtg gtt tgg tct tgg gac     1473
Val Val Phe Ala Ser Pro Ala Pro Asp Ser Val Val Trp Ser Trp Asp
            420                 425                 430

gag ggc ttc ttg gag gca ggc tca ctg ggc agg ttc cta gtg gaa gcc     1521
Glu Gly Phe Leu Glu Ala Gly Ser Leu Gly Arg Phe Leu Val Glu Ala
        435                 440                 445

ttc cca gcc ccg gaa gtg gag ggg gga cag ggc cct ggc ctt att tct     1569
Phe Pro Ala Pro Glu Val Glu Gly Gly Gln Gly Pro Gly Leu Ile Ser
    450                 455                 460

gtg cta cac att tcc gga acc cag gag tcc gac ttt acc acc ggc ttc     1617
Val Leu His Ile Ser Gly Thr Gln Glu Ser Asp Phe Thr Thr Gly Phe
465                 470                 475                 480

aac tgc agt gcc cgc aac cgg cta gga gag gga cga gtc cag atc cac     1665
Asn Cys Ser Ala Arg Asn Arg Leu Gly Glu Gly Arg Val Gln Ile His
                485                 490                 495

ttg ggc cgt aga gat ttg ctg cct act gtc cgg att gtg gct ggt gca     1713
Leu Gly Arg Arg Asp Leu Leu Pro Thr Val Arg Ile Val Ala Gly Ala
            500                 505                 510
```

```
gca tct gca gcc acc tct ctc ctt atg gtc atc act gga gtg gtc ctc      1761
Ala Ser Ala Ala Thr Ser Leu Leu Met Val Ile Thr Gly Val Val Leu
        515                 520                 525

tgc tgc tgg cgc cat ggc tct ctc tct aag caa aag aac ttg gtc cgg      1809
Cys Cys Trp Arg His Gly Ser Leu Ser Lys Gln Lys Asn Leu Val Arg
    530                 535                 540

atc cca gga agc agc gag ggt tcc agt tca cgt ggc cct gag gag gag      1857
Ile Pro Gly Ser Ser Glu Gly Ser Ser Ser Arg Gly Pro Glu Glu Glu
545                 550                 555                 560

aca ggc agc agt gag gac cgg ggt ccc att gtg cac acc gac cac agt      1905
Thr Gly Ser Ser Glu Asp Arg Gly Pro Ile Val His Thr Asp His Ser
                565                 570                 575

gat ttg gtt ctt gag gaa aaa gag gct ctg gag aca aag gat cca acc      1953
Asp Leu Val Leu Glu Glu Lys Glu Ala Leu Glu Thr Lys Asp Pro Thr
            580                 585                 590

aac ggt tac tac aag gtt cga ggg gtc agt gtg agc ctt agc ctt ggg      2001
Asn Gly Tyr Tyr Lys Val Arg Gly Val Ser Val Ser Leu Ser Leu Gly
        595                 600                 605

gaa gct cct gga gga ggc ctc ttc ttg cca ccg ccc tct ccg atc ggt      2049
Glu Ala Pro Gly Gly Gly Leu Phe Leu Pro Pro Pro Ser Pro Ile Gly
    610                 615                 620

ctc cca ggg act cct act tac tat gac ttc aag cca cat ctg gac tta      2097
Leu Pro Gly Thr Pro Thr Tyr Tyr Asp Phe Lys Pro His Leu Asp Leu
625                 630                 635                 640

gtc cct ccc tgc aga ctg tac aga gcg agg gca ggt tat ctt acc acc      2145
Val Pro Pro Cys Arg Leu Tyr Arg Ala Arg Ala Gly Tyr Leu Thr Thr
                645                 650                 655

ccc cat ccc cgt gcc ttc acc agc tac atg aaa ccc aca tcc ttt gga      2193
Pro His Pro Arg Ala Phe Thr Ser Tyr Met Lys Pro Thr Ser Phe Gly
            660                 665                 670

ccc cca gat ttg agc tct gga act ccc ccc ttc ccg tat gct acc ttg      2241
Pro Pro Asp Leu Ser Ser Gly Thr Pro Pro Phe Pro Tyr Ala Thr Leu
        675                 680                 685

tct cca ccc agc cac cag cgt ctc cag act cat gtg tgaatccatc           2287
Ser Pro Pro Ser His Gln Arg Leu Gln Thr His Val
    690                 695                 700

tctccaagtg aagggtcttg gaatcttctg tttgccatat agtgtgttgt ccagatttct   2347

ggggagtcag aacaagttga tgaccaaccc ctccaaaact gaacattgaa ggagggaaag   2407

atcattacaa gcatcaggac tgttggtgta cactcagttc agccaaagtg gattctccaa   2467

gtgggagcaa tatggccgct ttcccatgag aaagacattc aagatggtga ctaaatgact   2527

aaatactttg cagagggaca aagatgggaa ctagggatac ggatggaagt agtagagaag   2587

atatatgacc atctgcatca agaggaagga taacatatga caaatcaaga tgaaagaaat   2647

aatccacccc acccccaccg cgtcctggcc aataagtata gcctacatgg ctgttcatta   2707

tctgggaacc aaaatggcca ctatcttgac tccttcctta aagatacaga aagaattgaa   2767

tccaaggaat ggggtagggt ggaaatagaa gaaatgaagg ggactcttgg gctaagaata   2827

cttatgttta ataataaaag ggggaggcaa agatgcaaaa aaaaaaaaa               2876


<210> SEQ ID NO 2
<211> LENGTH: 700
<212> TYPE: PRT
<213> ORGANISM: Mus musculus

<400> SEQUENCE: 2

Met Leu Ala Ser Ala Leu Leu Val Phe Leu Cys Cys Phe Lys Gly His
1               5                   10                  15
```

```
Ala Gly Ser Ser Pro His Phe Leu Gln Gln Pro Glu Asp Met Val Val
            20                  25                  30

Leu Leu Gly Glu Glu Ala Arg Leu Pro Cys Ala Leu Gly Ala Tyr Arg
        35                  40                  45

Gly Leu Val Gln Trp Thr Lys Asp Gly Leu Ala Leu Gly Gly Glu Arg
    50                  55                  60

Asp Leu Pro Gly Trp Ser Arg Tyr Trp Ile Ser Gly Asn Ser Ala Ser
65                  70                  75                  80

Gly Gln His Asp Leu His Ile Lys Pro Val Glu Leu Glu Asp Glu Ala
                85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Ala Ser Ser Phe His Gln Thr Thr Leu Lys Asp
                165                 170                 175

Lys Ala Thr Gly Thr Val Glu Asn Thr Leu Phe Leu Thr Pro Ser Ser
            180                 185                 190

His Asp Asp Gly Ala Thr Leu Ile Cys Arg Ala Arg Ser Gln Ala Leu
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240

Val Thr Phe Leu Cys Gln Ala Thr Ala Gln Pro Pro Val Thr Gly Tyr
                245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
        275                 280                 285

Glu Val Ser Asn Ala Val Gly Ser Ala Asn Arg Ser Thr Ala Leu Glu
    290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
        355                 360                 365

Asp Tyr Val Cys Arg Ala Glu Pro Arg Arg Thr Gly Leu Gly Gly Gly
    370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
                405                 410                 415

Val Val Phe Ala Ser Pro Ala Pro Asp Ser Val Val Trp Ser Trp Asp
            420                 425                 430

Glu Gly Phe Leu Glu Ala Gly Ser Leu Gly Arg Phe Leu Val Glu Ala
```

```
        435                 440                 445

Phe Pro Ala Pro Glu Val Glu Gly Gly Gln Gly Pro Gly Leu Ile Ser
    450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
                485                 490                 495

Leu Gly Arg Arg Asp Leu Leu Pro Thr Val Arg Ile Val Ala Gly Ala
            500                 505                 510

Ala Ser Ala Ala Thr Ser Leu Leu Met Val Ile Thr Gly Val Val Leu
        515                 520                 525

Cys Cys Trp Arg His Gly Ser Leu Ser Lys Gln Lys Asn Leu Val Arg
    530                 535                 540

Ile Pro Gly Ser Ser Glu Gly Ser Ser Ser Arg Gly Pro Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Lys Val Arg Gly Val Ser Val Ser Leu Ser Leu Gly
        595                 600                 605

Glu Ala Pro Gly Gly Gly Leu Phe Leu Pro Pro Pro Ser Pro Ile Gly
    610                 615                 620

Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
                645                 650                 655

Pro His Pro Arg Ala Phe Thr Ser Tyr Met Lys Pro Thr Ser Phe Gly
            660                 665                 670

Pro Pro Asp Leu Ser Ser Gly Thr Pro Pro Phe Pro Tyr Ala Thr Leu
        675                 680                 685

Ser Pro Pro Ser His Gln Arg Leu Gln Thr His Val
    690                 695                 700


<210> SEQ ID NO 3
<211> LENGTH: 2243
<212> TYPE: DNA
<213> ORGANISM: Mus musculus
<220> FEATURE:
<221> NAME/KEY: CDS
<222> LOCATION: (127)..(2076)

<400> SEQUENCE: 3

gagagaattg tgtgcagaga gaggctccag tccagcgtgg tgtgagaggc gtgctatcaa      60

gaaagaagtt ggaggggaac cagtgcaacc ctaactctac gagatcttgg ggtacacaca     120

ctcggg atg ctg gcc tcc gcc ctc ctc gtt ttc ctt tgc tgt ttc aaa        168
       Met Leu Ala Ser Ala Leu Leu Val Phe Leu Cys Cys Phe Lys
       1               5                   10

gga cat gca ggg tgg tcc cgg tac tgg ata tcg ggg aat tca gcc agt       216
Gly His Ala Gly Trp Ser Arg Tyr Trp Ile Ser Gly Asn Ser Ala Ser
15                  20                  25                  30

ggc cag cat gac ctc cac att aag cct gtg gaa ttg gaa gat gag gca       264
Gly Gln His Asp Leu His Ile Lys Pro Val Glu Leu Glu Asp Glu Ala
                35                  40                  45

tcg tat gag tgc cag gct tcg caa gca ggt ctc cga tca cga cca gcc       312
Ser Tyr Glu Cys Gln Ala Ser Gln Ala Gly Leu Arg Ser Arg Pro Ala
```

```
            50                  55                  60

caa ctg cac gtg atg gtc ccc cca gaa gct ccc cag gta cta ggc ggc      360
Gln Leu His Val Met Val Pro Pro Glu Ala Pro Gln Val Leu Gly Gly
        65                  70                  75

ccc tct gtg tct ctg gtt gct gga gtt cct gga aat ctg acc tgt cgg      408
Pro Ser Val Ser Leu Val Ala Gly Val Pro Gly Asn Leu Thr Cys Arg
    80                  85                  90

agt cgt ggg gat tcc cga cct gcc cct gaa cta ctg tgg ttc cga gat      456
Ser Arg Gly Asp Ser Arg Pro Ala Pro Glu Leu Leu Trp Phe Arg Asp
95                  100                 105                 110

ggg atc cgg ctg gat gcg agc agc ttc cac cag acc acg ctg aag gac      504
Gly Ile Arg Leu Asp Ala Ser Ser Phe His Gln Thr Thr Leu Lys Asp
                115                 120                 125

aag gcc act gga aca gtg gaa aac acc tta ttc ctg acc cct tcc agt      552
Lys Ala Thr Gly Thr Val Glu Asn Thr Leu Phe Leu Thr Pro Ser Ser
            130                 135                 140

cat gat gat ggc gcc acc ttg atc tgc aga gcg cga agc cag gcc ctg      600
His Asp Asp Gly Ala Thr Leu Ile Cys Arg Ala Arg Ser Gln Ala Leu
        145                 150                 155

ccc aca ggg agg gac aca gct gtt aca ctg agc ctt cag tat ccc cca      648
Pro Thr Gly Arg Asp Thr Ala Val Thr Leu Ser Leu Gln Tyr Pro Pro
    160                 165                 170

atg gtg act ctg tct gct gag ccc cag act gtg cag gag gga gag aag      696
Met Val Thr Leu Ser Ala Glu Pro Gln Thr Val Gln Glu Gly Glu Lys
175                 180                 185                 190

gtg act ttc ctg tgt caa gcc act gcc cag cct cct gtc act ggc tac      744
Val Thr Phe Leu Cys Gln Ala Thr Ala Gln Pro Pro Val Thr Gly Tyr
                195                 200                 205

agg tgg gcg aag ggg gga tcc ccg gtg ctc ggg gca cgt ggg cca agg      792
Arg Trp Ala Lys Gly Gly Ser Pro Val Leu Gly Ala Arg Gly Pro Arg
            210                 215                 220

ttg gag gtc gtt gca gat gcc act ttc ctg act gag ccg gtg tcc tgc      840
Leu Glu Val Val Ala Asp Ala Thr Phe Leu Thr Glu Pro Val Ser Cys
        225                 230                 235

gag gtc agc aac gcg gtc gga agc gcc aac cgc agc acg gcg ctg gaa      888
Glu Val Ser Asn Ala Val Gly Ser Ala Asn Arg Ser Thr Ala Leu Glu
    240                 245                 250

gtg ttg tat gga ccc att ctg cag gca aaa cct aag tcc gtg tcc gtg      936
Val Leu Tyr Gly Pro Ile Leu Gln Ala Lys Pro Lys Ser Val Ser Val
255                 260                 265                 270

gac gtg ggg aaa gat gcc tcc ttc agc tgt gtc tgg cgc ggg aac cca      984
Asp Val Gly Lys Asp Ala Ser Phe Ser Cys Val Trp Arg Gly Asn Pro
                275                 280                 285

ctt cca cgg ata acc tgg acc cgc atg ggt ggc tct cag gtg ctg agc     1032
Leu Pro Arg Ile Thr Trp Thr Arg Met Gly Gly Ser Gln Val Leu Ser
            290                 295                 300

tcc ggg ccc acg ctg cgg ctt ccg tcc gtg gca ctg gag gat gcg ggc     1080
Ser Gly Pro Thr Leu Arg Leu Pro Ser Val Ala Leu Glu Asp Ala Gly
        305                 310                 315

gac tat gta tgc agg gct gag ccg agg aga acg ggt ctg gga ggc ggc     1128
Asp Tyr Val Cys Arg Ala Glu Pro Arg Arg Thr Gly Leu Gly Gly Gly
    320                 325                 330

aaa gcg cag gcg agg ctg act gtg aac gca ccc cct gta gtg aca gcc     1176
Lys Ala Gln Ala Arg Leu Thr Val Asn Ala Pro Pro Val Val Thr Ala
335                 340                 345                 350

ctg caa cct gca cca gcc ttt ctg agg ggt cct gct cgc ctc cag tgt     1224
Leu Gln Pro Ala Pro Ala Phe Leu Arg Gly Pro Ala Arg Leu Gln Cys
                355                 360                 365

gtg gtg ttt gcc tcc cct gcc cca gac tcg gtg gtt tgg tct tgg gac     1272
```

```
Val Val Phe Ala Ser Pro Ala Pro Asp Ser Val Val Trp Ser Trp Asp
            370                 375                 380

gag ggc ttc ttg gag gca ggc tca ctg ggc agg ttc cta gtg gaa gcc      1320
Glu Gly Phe Leu Glu Ala Gly Ser Leu Gly Arg Phe Leu Val Glu Ala
        385                 390                 395

ttc cca gcc ccg gaa gtg gag ggg gga cag ggc cct ggc ctt att tct      1368
Phe Pro Ala Pro Glu Val Glu Gly Gly Gln Gly Pro Gly Leu Ile Ser
    400                 405                 410

gtg cta cac att tcc gga acc cag gag tcc gac ttt acc acc ggc ttc      1416
Val Leu His Ile Ser Gly Thr Gln Glu Ser Asp Phe Thr Thr Gly Phe
415                 420                 425                 430

aac tgc agt gcc cgc aac cgg cta gga gag gga cga gtc cag atc cac      1464
Asn Cys Ser Ala Arg Asn Arg Leu Gly Glu Gly Arg Val Gln Ile His
                435                 440                 445

ttg ggc cgt aga gat ttg ctg cct act gtc cgg att gtg gct ggt gca      1512
Leu Gly Arg Arg Asp Leu Leu Pro Thr Val Arg Ile Val Ala Gly Ala
            450                 455                 460

gca tct gca gcc acc tct ctc ctt atg gtc atc act gga gtg gtc ctc      1560
Ala Ser Ala Ala Thr Ser Leu Leu Met Val Ile Thr Gly Val Val Leu
        465                 470                 475

tgc tgc tgg cgc cat ggc tct ctc tct aag caa aag aac ttg gtc cgg      1608
Cys Cys Trp Arg His Gly Ser Leu Ser Lys Gln Lys Asn Leu Val Arg
    480                 485                 490

atc cca gga agc agc gag ggt tcc agt tca cgt ggc cct gag gag gag      1656
Ile Pro Gly Ser Ser Glu Gly Ser Ser Ser Arg Gly Pro Glu Glu Glu
495                 500                 505                 510

aca ggc agc agt gag gac cgg ggt ccc att gtg cac acc gac cac agt      1704
Thr Gly Ser Ser Glu Asp Arg Gly Pro Ile Val His Thr Asp His Ser
                515                 520                 525

gat ttg gtt ctt gag gaa aaa gag gct ctg gag aca aag gat cca acc      1752
Asp Leu Val Leu Glu Glu Lys Glu Ala Leu Glu Thr Lys Asp Pro Thr
            530                 535                 540

aac ggt tac tac aag gtt cga ggg gtc agt gtg agc ctt agc ctt ggg      1800
Asn Gly Tyr Tyr Lys Val Arg Gly Val Ser Val Ser Leu Ser Leu Gly
        545                 550                 555

gaa gct cct gga gga ggc ctc ttc ttg cca ccg ccc tct ccg atc ggt      1848
Glu Ala Pro Gly Gly Gly Leu Phe Leu Pro Pro Pro Ser Pro Ile Gly
    560                 565                 570

ctc cca ggg act cct act tac tat gac ttc aag cca cat cag gac tta      1896
Leu Pro Gly Thr Pro Thr Tyr Tyr Asp Phe Lys Pro His Gln Asp Leu
575                 580                 585                 590

gtc cct ccc tgc aga ctg tac aga gcg agg gca ggt tat ctt acc acc      1944
Val Pro Pro Cys Arg Leu Tyr Arg Ala Arg Ala Gly Tyr Leu Thr Thr
                595                 600                 605

ccc cat ccc cgt gcc ttc acc agc tac atg aaa ccc aca tcc ttt gga      1992
Pro His Pro Arg Ala Phe Thr Ser Tyr Met Lys Pro Thr Ser Phe Gly
            610                 615                 620

ccc cca gat ttg agc tct gga act ccc ccc ttc ccg tat gct acc ttg      2040
Pro Pro Asp Leu Ser Ser Gly Thr Pro Pro Phe Pro Tyr Ala Thr Leu
        625                 630                 635

tct cca ccc agc cac cag cgt ctc cag act cat gtg tgaatccatc           2086
Ser Pro Pro Ser His Gln Arg Leu Gln Thr His Val
    640                 645                 650

tctccaagtg aagggtcttg gaatcttctg tttgccatat agtgtgttgt ccagatttct    2146

ggggagtcag aacaagttga tgaccaaccc ctccaaaact gaacattgaa ggagggaaag    2206

atcattacaa gcatcaggac tgttggtgta cactcag                             2243


<210> SEQ ID NO 4
```

```
<211> LENGTH: 650
<212> TYPE: PRT
<213> ORGANISM: Mus musculus

<400> SEQUENCE: 4

Met Leu Ala Ser Ala Leu Leu Val Phe Leu Cys Cys Phe Lys Gly His
1               5                   10                  15

Ala Gly Trp Ser Arg Tyr Trp Ile Ser Gly Asn Ser Ala Ser Gly Gln
            20                  25                  30

His Asp Leu His Ile Lys Pro Val Glu Leu Glu Asp Glu Ala Ser Tyr
        35                  40                  45

Glu Cys Gln Ala Ser Gln Ala Gly Leu Arg Ser Arg Pro Ala Gln Leu
    50                  55                  60

His Val Met Val Pro Pro Glu Ala Pro Gln Val Leu Gly Gly Pro Ser
65                  70                  75                  80

Val Ser Leu Val Ala Gly Val Pro Gly Asn Leu Thr Cys Arg Ser Arg
                85                  90                  95

Gly Asp Ser Arg Pro Ala Pro Glu Leu Leu Trp Phe Arg Asp Gly Ile
            100                 105                 110

Arg Leu Asp Ala Ser Ser Phe His Gln Thr Thr Leu Lys Asp Lys Ala
        115                 120                 125

Thr Gly Thr Val Glu Asn Thr Leu Phe Leu Thr Pro Ser Ser His Asp
    130                 135                 140

Asp Gly Ala Thr Leu Ile Cys Arg Ala Arg Ser Gln Ala Leu Pro Thr
145                 150                 155                 160

Gly Arg Asp Thr Ala Val Thr Leu Ser Leu Gln Tyr Pro Pro Met Val
                165                 170                 175

Thr Leu Ser Ala Glu Pro Gln Thr Val Gln Glu Gly Glu Lys Val Thr
            180                 185                 190

Phe Leu Cys Gln Ala Thr Ala Gln Pro Pro Val Thr Gly Tyr Arg Trp
        195                 200                 205

Ala Lys Gly Gly Ser Pro Val Leu Gly Ala Arg Gly Pro Arg Leu Glu
    210                 215                 220

Val Val Ala Asp Ala Thr Phe Leu Thr Glu Pro Val Ser Cys Glu Val
225                 230                 235                 240

Ser Asn Ala Val Gly Ser Ala Asn Arg Ser Thr Ala Leu Glu Val Leu
                245                 250                 255

Tyr Gly Pro Ile Leu Gln Ala Lys Pro Lys Ser Val Ser Val Asp Val
            260                 265                 270

Gly Lys Asp Ala Ser Phe Ser Cys Val Trp Arg Gly Asn Pro Leu Pro
        275                 280                 285

Arg Ile Thr Trp Thr Arg Met Gly Gly Ser Gln Val Leu Ser Ser Gly
    290                 295                 300

Pro Thr Leu Arg Leu Pro Ser Val Ala Leu Glu Asp Ala Gly Asp Tyr
305                 310                 315                 320

Val Cys Arg Ala Glu Pro Arg Arg Thr Gly Leu Gly Gly Gly Lys Ala
                325                 330                 335

Gln Ala Arg Leu Thr Val Asn Ala Pro Pro Val Val Thr Ala Leu Gln
            340                 345                 350

Pro Ala Pro Ala Phe Leu Arg Gly Pro Ala Arg Leu Gln Cys Val Val
        355                 360                 365

Phe Ala Ser Pro Ala Pro Asp Ser Val Val Trp Ser Trp Asp Glu Gly
    370                 375                 380

Phe Leu Glu Ala Gly Ser Leu Gly Arg Phe Leu Val Glu Ala Phe Pro
```

```
385                 390                 395                 400

Ala Pro Glu Val Glu Gly Gly Gln Gly Pro Gly Leu Ile Ser Val Leu
                405                 410                 415

His Ile Ser Gly Thr Gln Glu Ser Asp Phe Thr Thr Gly Phe Asn Cys
            420                 425                 430

Ser Ala Arg Asn Arg Leu Gly Glu Gly Arg Val Gln Ile His Leu Gly
        435                 440                 445

Arg Arg Asp Leu Leu Pro Thr Val Arg Ile Val Ala Gly Ala Ala Ser
    450                 455                 460

Ala Ala Thr Ser Leu Leu Met Val Ile Thr Gly Val Val Leu Cys Cys
465                 470                 475                 480

Trp Arg His Gly Ser Leu Ser Lys Gln Lys Asn Leu Val Arg Ile Pro
                485                 490                 495

Gly Ser Ser Glu Gly Ser Ser Ser Arg Gly Pro Glu Glu Glu Thr Gly
            500                 505                 510

Ser Ser Glu Asp Arg Gly Pro Ile Val His Thr Asp His Ser Asp Leu
        515                 520                 525

Val Leu Glu Glu Lys Glu Ala Leu Glu Thr Lys Asp Pro Thr Asn Gly
    530                 535                 540

Tyr Tyr Lys Val Arg Gly Val Ser Val Ser Leu Ser Leu Gly Glu Ala
545                 550                 555                 560

Pro Gly Gly Gly Leu Phe Leu Pro Pro Pro Ser Pro Ile Gly Leu Pro
                565                 570                 575

Gly Thr Pro Thr Tyr Tyr Asp Phe Lys Pro His Gln Asp Leu Val Pro
            580                 585                 590

Pro Cys Arg Leu Tyr Arg Ala Arg Ala Gly Tyr Leu Thr Thr Pro His
        595                 600                 605

Pro Arg Ala Phe Thr Ser Tyr Met Lys Pro Thr Ser Phe Gly Pro Pro
    610                 615                 620

Asp Leu Ser Ser Gly Thr Pro Pro Phe Pro Tyr Ala Thr Leu Ser Pro
625                 630                 635                 640

Pro Ser His Gln Arg Leu Gln Thr His Val
                645                 650
```

<210> SEQ ID NO 5
<211> LENGTH: 3123
<212> TYPE: DNA
<213> ORGANISM: Mus musculus
<220> FEATURE:
<221> NAME/KEY: CDS
<222> LOCATION: (668)..(2767)

<400> SEQUENCE: 5

```
gctctctccg acccgcaggc ccacgggagc ctgagctccg cctccccagg gcgcggaagc     60

tggcgaagcc ccagggattc ccatttatag cttggtttcc actcagctca gtccctccag    120

gactcgggct gagcaagttt cttccattcc cttctctcct ccctccaccc ccttctcctc    180

ctccttctcc ttcttttctt cctcctcatt cccgcctccc cttcaacctc agcagggtgc    240

aggtgtccaa ctcgaacaag ggccccaact tggactcaga tgttcccact ctcagacccc    300

ctgataatgc aggggcgccc gcctgctgcg cggacagcta ccctgagcat ccgtagccgt    360

ccgcacacaa ggcgcgggag tttctcaatg ggaagaggcc gggactctag gaggcggggc    420

gaataggatt cctcccgcct agtgggtccc tcgcagtcct agggttgcaa cccttgagcg    480

gtagagaaca ccggagactg cggatgagcc agatttcggg gacataaaat cttccagccc    540
```

```
ggagagaatt gtgtgcagag aggggctcca gtccagcgtg gtgtgagagg cgtgctatca    600

agaaagaagt tggaggggaa ccagtgcaac cctaactctg cgagatcttg ggtacacac     660

actcggg atg ctg gcc tcc gcc ctc ctc gtt ttc ctt tgc tgt ttc aaa      709
        Met Leu Ala Ser Ala Leu Leu Val Phe Leu Cys Cys Phe Lys
        1               5                   10

gga cat gca ggc tca tcg ccc cat ttc cta caa cag cca gag gac atg      757
Gly His Ala Gly Ser Ser Pro His Phe Leu Gln Gln Pro Glu Asp Met
15                  20                  25                  30

gtg gtg ctg ttg ggg gag gaa gcc cgg ctg ccc tgc gct ctg ggc gcg      805
Val Val Leu Leu Gly Glu Glu Ala Arg Leu Pro Cys Ala Leu Gly Ala
                35                  40                  45

tac agg ggg ctc gtg cag tgg act aag gat ggg ctg gct cta ggg ggc      853
Tyr Arg Gly Leu Val Gln Trp Thr Lys Asp Gly Leu Ala Leu Gly Gly
            50                  55                  60

gaa aga gac ctt cca ggg tgg tcc cgg tac tgg ata tcg ggg aat tca      901
Glu Arg Asp Leu Pro Gly Trp Ser Arg Tyr Trp Ile Ser Gly Asn Ser
        65                  70                  75

gcc agt ggc cag cat gac ctc cac att aag cct gtg gaa ttg gaa gat      949
Ala Ser Gly Gln His Asp Leu His Ile Lys Pro Val Glu Leu Glu Asp
    80                  85                  90

gag gca tcg tat gag tgc cag gct tcg caa gca ggt ctc cga tca cga      997
Glu Ala Ser Tyr Glu Cys Gln Ala Ser Gln Ala Gly Leu Arg Ser Arg
95                  100                 105                 110

cca gcc caa ctg cac gtg atg gtc ccc cca gaa gct ccc cag gta cta     1045
Pro Ala Gln Leu His Val Met Val Pro Pro Glu Ala Pro Gln Val Leu
                115                 120                 125

ggc ggc ccc tct gtg tct ctg gtt gct gga gtt cct gga aat ctg acc     1093
Gly Gly Pro Ser Val Ser Leu Val Ala Gly Val Pro Gly Asn Leu Thr
            130                 135                 140

tgt cgg agt cgt ggg gat tca cga cct gcc cct gaa cta ctg tgg ttc     1141
Cys Arg Ser Arg Gly Asp Ser Arg Pro Ala Pro Glu Leu Leu Trp Phe
        145                 150                 155

cga gat ggg atc cgg ctg gat ggg agc agc ttc cac cag acc acg ctg     1189
Arg Asp Gly Ile Arg Leu Asp Gly Ser Ser Phe His Gln Thr Thr Leu
    160                 165                 170

aag gac aag gcc act gga aca gtg gaa aac acc tta ttc ctg acc cct     1237
Lys Asp Lys Ala Thr Gly Thr Val Glu Asn Thr Leu Phe Leu Thr Pro
175                 180                 185                 190

tcc agt cat gat gat ggt gcc acc ttg atc tgc aga gcg cga agc cag     1285
Ser Ser His Asp Asp Gly Ala Thr Leu Ile Cys Arg Ala Arg Ser Gln
                195                 200                 205

gcc ctg ccc aca ggg agg gac aca gct gtt aca ctg agc ctt cag tat     1333
Ala Leu Pro Thr Gly Arg Asp Thr Ala Val Thr Leu Ser Leu Gln Tyr
            210                 215                 220

ccc cca atg gtg act ctg tct gct gag ccc cag act gtg cag gag gga     1381
Pro Pro Met Val Thr Leu Ser Ala Glu Pro Gln Thr Val Gln Glu Gly
        225                 230                 235

gag aag gtg act ttc ctg tgt caa gcc act gcc cag cct cct gtc act     1429
Glu Lys Val Thr Phe Leu Cys Gln Ala Thr Ala Gln Pro Pro Val Thr
    240                 245                 250

ggc tac agg tgg gcg aag ggg gga tcc ccg gtg ctt ggg gca cgt ggg     1477
Gly Tyr Arg Trp Ala Lys Gly Gly Ser Pro Val Leu Gly Ala Arg Gly
255                 260                 265                 270

cca agg ttg gag gtc gtt gca gat gcc act ttc ctg act gag ccg gtg     1525
Pro Arg Leu Glu Val Val Ala Asp Ala Thr Phe Leu Thr Glu Pro Val
                275                 280                 285

tcc tgc gag gtc agc aac gcg gtc gga agc gcc aac cgc agc acc gcg     1573
Ser Cys Glu Val Ser Asn Ala Val Gly Ser Ala Asn Arg Ser Thr Ala
            290                 295                 300
```

```
ctg gaa gtg ttg tat gga ccc att ctg cag gca aaa cct aag tcc gtg      1621
Leu Glu Val Leu Tyr Gly Pro Ile Leu Gln Ala Lys Pro Lys Ser Val
        305                 310                 315

tcc gtg gac gtg ggg aaa gat gcc tcc ttc agc tgt gtc tgg cgc ggg      1669
Ser Val Asp Val Gly Lys Asp Ala Ser Phe Ser Cys Val Trp Arg Gly
    320                 325                 330

aac cca ctt cca cgg ata acc tgg acc cgc atg ggt ggc tct cag gtg      1717
Asn Pro Leu Pro Arg Ile Thr Trp Thr Arg Met Gly Gly Ser Gln Val
335                 340                 345                 350

ctg agc tcc ggg ccc acg ctg cgg ctt ccg tcc gtg gca ctg gag gat      1765
Leu Ser Ser Gly Pro Thr Leu Arg Leu Pro Ser Val Ala Leu Glu Asp
                355                 360                 365

gcg ggc gac tat gta tgc agg gct gag ccg agg aga acg ggt ctg gga      1813
Ala Gly Asp Tyr Val Cys Arg Ala Glu Pro Arg Arg Thr Gly Leu Gly
            370                 375                 380

ggc ggc aaa gcg cag gcg agg ctg act gtg aac gca ccc cct gta gtg      1861
Gly Gly Lys Ala Gln Ala Arg Leu Thr Val Asn Ala Pro Pro Val Val
        385                 390                 395

aca gcc ctg caa cct gca cca gcc ttt ctg agg ggt cct gct cgc ctc      1909
Thr Ala Leu Gln Pro Ala Pro Ala Phe Leu Arg Gly Pro Ala Arg Leu
    400                 405                 410

cag tgt gtg gtg ttt gcc tcc cct gcc cca gac tcg gtg gtt tgg tct      1957
Gln Cys Val Val Phe Ala Ser Pro Ala Pro Asp Ser Val Val Trp Ser
415                 420                 425                 430

tgg gac gag ggc ttc ttg gag gca ggc tca ctg ggc agg ttc cta gtg      2005
Trp Asp Glu Gly Phe Leu Glu Ala Gly Ser Leu Gly Arg Phe Leu Val
                435                 440                 445

gaa gcc ttc cca gcc ccg gaa gtg gag ggg gga cag ggc cct ggc ctt      2053
Glu Ala Phe Pro Ala Pro Glu Val Glu Gly Gly Gln Gly Pro Gly Leu
            450                 455                 460

att tct gtg cta cac att tcc gga acc cag gag tcc gac ttt acc acc      2101
Ile Ser Val Leu His Ile Ser Gly Thr Gln Glu Ser Asp Phe Thr Thr
        465                 470                 475

ggc ttc aac tgc agt gcc cgc aac cgg cta gga gag gga cga gtc cag      2149
Gly Phe Asn Cys Ser Ala Arg Asn Arg Leu Gly Glu Gly Arg Val Gln
    480                 485                 490

atc cac ttg ggc cgt aga gac ttg ctg cct act gtc cgg att gtg gct      2197
Ile His Leu Gly Arg Arg Asp Leu Leu Pro Thr Val Arg Ile Val Ala
495                 500                 505                 510

ggt gca gca tct gca gcc acc tct ctc ctt atg gtc atc act gga gtg      2245
Gly Ala Ala Ser Ala Ala Thr Ser Leu Leu Met Val Ile Thr Gly Val
                515                 520                 525

gtc ctc tgc tgc tgg cgc cat ggc tct ctc tct aag caa aag aac ttg      2293
Val Leu Cys Cys Trp Arg His Gly Ser Leu Ser Lys Gln Lys Asn Leu
            530                 535                 540

gtc cgg atc ccg gga agc agc gag ggt tcc agt tca cgt ggc cct gag      2341
Val Arg Ile Pro Gly Ser Ser Glu Gly Ser Ser Ser Arg Gly Pro Glu
        545                 550                 555

gag gag aca ggc agc agt gag gac cgg ggt ccc att gtg cac acc gac      2389
Glu Glu Thr Gly Ser Ser Glu Asp Arg Gly Pro Ile Val His Thr Asp
    560                 565                 570

cac agt gat ttg gtt ctt gag gaa aaa gag gct ctg gag aca aag gat      2437
His Ser Asp Leu Val Leu Glu Glu Lys Glu Ala Leu Glu Thr Lys Asp
575                 580                 585                 590

cca acc aac ggt tac tac agg gtt cga ggg gtc agt gtg agc ctt agc      2485
Pro Thr Asn Gly Tyr Tyr Arg Val Arg Gly Val Ser Val Ser Leu Ser
                595                 600                 605

ctt ggg gaa gct cct gga gga ggc ctc ttc ttg cca ccg ccc tct ccg      2533
Leu Gly Glu Ala Pro Gly Gly Gly Leu Phe Leu Pro Pro Pro Ser Pro
```

```
            610                 615                 620

atc ggt ctc cca ggg act cct act tac tat gac ttc aag cca cat ctg      2581
Ile Gly Leu Pro Gly Thr Pro Thr Tyr Tyr Asp Phe Lys Pro His Leu
        625                 630                 635

gac tta gtc cct ccc tgc aga ctg tac aga gcg agg gca ggt tat ctt      2629
Asp Leu Val Pro Pro Cys Arg Leu Tyr Arg Ala Arg Ala Gly Tyr Leu
    640                 645                 650

acc acc ccc cat ccc cgt gcc ttc acc agc tac atg aaa ccc aca tcc      2677
Thr Thr Pro His Pro Arg Ala Phe Thr Ser Tyr Met Lys Pro Thr Ser
655                 660                 665                 670

ttt gga ccc cca gaa ttg agc tct gga act ccc ccc ttc ccg tat gct      2725
Phe Gly Pro Pro Glu Leu Ser Ser Gly Thr Pro Pro Phe Pro Tyr Ala
                675                 680                 685

acc ttg tct cca ccc agc cac cag cgt ctc cag act cat gtg              2767
Thr Leu Ser Pro Pro Ser His Gln Arg Leu Gln Thr His Val
            690                 695                 700

tgaatccatc tctccaagtg aagggtcttg gaatcttctg tttgccatat agtgtgttgt   2827

ccagatttct ggggagtcag aacaagttga tgaccaaccc ctccaaaact gaacattgaa   2887

ggagggaaag atcattacaa gcatcaggac tgttggtgta cactcagttc agccaaagtg   2947

gattctccaa gtgggagcaa tatggccgct ttcccatgag aaagacattc aagatggtga   3007

ctaaatgact aaatactttg cagagggaca aagatgggaa ctagggatat ggatggaagt   3067

agtagagaag atatatgacc atctgcatca agagaaagga taacataaga caaatc       3123


<210> SEQ ID NO 6
<211> LENGTH: 700
<212> TYPE: PRT
<213> ORGANISM: Mus musculus

<400> SEQUENCE: 6

Met Leu Ala Ser Ala Leu Leu Val Phe Leu Cys Cys Phe Lys Gly His
1               5                   10                  15

Ala Gly Ser Ser Pro His Phe Leu Gln Gln Pro Glu Asp Met Val Val
            20                  25                  30

Leu Leu Gly Glu Glu Ala Arg Leu Pro Cys Ala Leu Gly Ala Tyr Arg
        35                  40                  45

Gly Leu Val Gln Trp Thr Lys Asp Gly Leu Ala Leu Gly Gly Glu Arg
    50                  55                  60

Asp Leu Pro Gly Trp Ser Arg Tyr Trp Ile Ser Gly Asn Ser Ala Ser
65                  70                  75                  80

Gly Gln His Asp Leu His Ile Lys Pro Val Glu Leu Glu Asp Glu Ala
                85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Gly Ser Ser Phe His Gln Thr Thr Leu Lys Asp
                165                 170                 175

Lys Ala Thr Gly Thr Val Glu Asn Thr Leu Phe Leu Thr Pro Ser Ser
            180                 185                 190

His Asp Asp Gly Ala Thr Leu Ile Cys Arg Ala Arg Ser Gln Ala Leu
```

```
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240

Val Thr Phe Leu Cys Gln Ala Thr Ala Gln Pro Pro Val Thr Gly Tyr
                245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
        275                 280                 285

Glu Val Ser Asn Ala Val Gly Ser Ala Asn Arg Ser Thr Ala Leu Glu
    290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
        355                 360                 365

Asp Tyr Val Cys Arg Ala Glu Pro Arg Arg Thr Gly Leu Gly Gly Gly
    370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
                405                 410                 415

Val Val Phe Ala Ser Pro Ala Pro Asp Ser Val Val Trp Ser Trp Asp
            420                 425                 430

Glu Gly Phe Leu Glu Ala Gly Ser Leu Gly Arg Phe Leu Val Glu Ala
        435                 440                 445

Phe Pro Ala Pro Glu Val Glu Gly Gly Gln Gly Pro Gly Leu Ile Ser
    450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
                485                 490                 495

Leu Gly Arg Arg Asp Leu Leu Pro Thr Val Arg Ile Val Ala Gly Ala
            500                 505                 510

Ala Ser Ala Ala Thr Ser Leu Leu Met Val Ile Thr Gly Val Val Leu
        515                 520                 525

Cys Cys Trp Arg His Gly Ser Leu Ser Lys Gln Lys Asn Leu Val Arg
    530                 535                 540

Ile Pro Gly Ser Ser Glu Gly Ser Ser Ser Arg Gly Pro Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Arg Val Arg Gly Val Ser Val Ser Leu Ser Leu Gly
        595                 600                 605

Glu Ala Pro Gly Gly Gly Leu Phe Leu Pro Pro Pro Ser Pro Ile Gly
    610                 615                 620
```

```
Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
                645                 650                 655

Pro His Pro Arg Ala Phe Thr Ser Tyr Met Lys Pro Thr Ser Phe Gly
            660                 665                 670

Pro Pro Glu Leu Ser Ser Gly Thr Pro Pro Phe Pro Tyr Ala Thr Leu
        675                 680                 685

Ser Pro Pro Ser His Gln Arg Leu Gln Thr His Val
    690                 695                 700


<210> SEQ ID NO 7
<211> LENGTH: 2847
<212> TYPE: DNA
<213> ORGANISM: Mus musculus
<220> FEATURE:
<221> NAME/KEY: CDS
<222> LOCATION: (130)..(2229)

<400> SEQUENCE: 7

ggtccggaat tcccgggatg agaggggctc cagtccagcg tggtgtgaga ggcgtgctat      60

caagaaagaa gttggagggg aaccagtgca accctaactc tgcgagatct tggggtacac     120

acactcggg atg ctg gcc tcc gcc ctc ctc gtt ttc ctt tgc tgt ttc aaa     171
          Met Leu Ala Ser Ala Leu Leu Val Phe Leu Cys Cys Phe Lys
          1               5                   10

gga cat gca ggc tca tcg ccc cat ttc cta caa cag cca gag gac atg       219
Gly His Ala Gly Ser Ser Pro His Phe Leu Gln Gln Pro Glu Asp Met
15                  20                  25                  30

gtg gtg ctg ttg ggg gag gaa gcc cgg ctg ccc tgc gct ctg ggc gcg       267
Val Val Leu Leu Gly Glu Glu Ala Arg Leu Pro Cys Ala Leu Gly Ala
                35                  40                  45

tac agg ggg ctc gtg cag tgg act aag gat ggg ctg gct cta ggg ggc       315
Tyr Arg Gly Leu Val Gln Trp Thr Lys Asp Gly Leu Ala Leu Gly Gly
            50                  55                  60

gaa aga gac ctt cca ggg tgg tcc cgg tac tgg ata tcg ggg aat tca       363
Glu Arg Asp Leu Pro Gly Trp Ser Arg Tyr Trp Ile Ser Gly Asn Ser
        65                  70                  75

gcc agt ggc cag cat gac ctc cac att aag cct gtg gaa ttg gaa gat       411
Ala Ser Gly Gln His Asp Leu His Ile Lys Pro Val Glu Leu Glu Asp
    80                  85                  90

gag gca tcg tat gag tgc cag gct tcg caa gca ggt ctc cga tca cga       459
Glu Ala Ser Tyr Glu Cys Gln Ala Ser Gln Ala Gly Leu Arg Ser Arg
95                  100                 105                 110

cca gcc caa ctg cac gtg atg gtc ccc cca gaa gct ccc cag gta cta       507
Pro Ala Gln Leu His Val Met Val Pro Pro Glu Ala Pro Gln Val Leu
                115                 120                 125

ggc ggc ccc tct gtg tct ctg gtt gct gga gtt cct gga aat ctg acc       555
Gly Gly Pro Ser Val Ser Leu Val Ala Gly Val Pro Gly Asn Leu Thr
            130                 135                 140

tgt cgg agt cgt ggg gat tca cga cct gcc cct gaa cta ctg tgg ttc       603
Cys Arg Ser Arg Gly Asp Ser Arg Pro Ala Pro Glu Leu Leu Trp Phe
        145                 150                 155

cga gat ggg atc cgg ctg gat ggg agc agc ttc cac cag acc acg ctg       651
Arg Asp Gly Ile Arg Leu Asp Gly Ser Ser Phe His Gln Thr Thr Leu
    160                 165                 170

aag gac aag gcc act gga aca gtg gaa aac acc tta ttc ctg acc cct       699
Lys Asp Lys Ala Thr Gly Thr Val Glu Asn Thr Leu Phe Leu Thr Pro
175                 180                 185                 190
```

```
tcc agt cat gat gat ggt gcc acc ttg atc tgc aga gcg cga agc cag      747
Ser Ser His Asp Asp Gly Ala Thr Leu Ile Cys Arg Ala Arg Ser Gln
                195                 200                 205

gcc ctg ccc aca ggg agg gac aca gct gtt aca ctg agc ctt cag tat      795
Ala Leu Pro Thr Gly Arg Asp Thr Ala Val Thr Leu Ser Leu Gln Tyr
            210                 215                 220

ccc cca atg gtg act ctg tct gct gag ccc cag act gtg cag gag gga      843
Pro Pro Met Val Thr Leu Ser Ala Glu Pro Gln Thr Val Gln Glu Gly
        225                 230                 235

gag aag gtg act ttc ctg tgt caa gcc act gcc cag cct cct gtc act      891
Glu Lys Val Thr Phe Leu Cys Gln Ala Thr Ala Gln Pro Pro Val Thr
    240                 245                 250

ggc tac agg tgg gcg aag ggg gga tcc ccg gtg ctt ggg gca cgt ggg      939
Gly Tyr Arg Trp Ala Lys Gly Gly Ser Pro Val Leu Gly Ala Arg Gly
255                 260                 265                 270

cca agg ttg gag gtc gtt gca gat gcc act ttc ctg act gag ccg gtg      987
Pro Arg Leu Glu Val Val Ala Asp Ala Thr Phe Leu Thr Glu Pro Val
                275                 280                 285

tcc tgc gag gtc agc aac gcg gtc gga agc gcc aac cgc agc acc gcg     1035
Ser Cys Glu Val Ser Asn Ala Val Gly Ser Ala Asn Arg Ser Thr Ala
            290                 295                 300

ctg gaa gtg ttg tat gga ccc att ctg cag gca aaa cct aag tcc gtg     1083
Leu Glu Val Leu Tyr Gly Pro Ile Leu Gln Ala Lys Pro Lys Ser Val
        305                 310                 315

tcc gtg gac gtg ggg aaa gat gcc tcc ttc agc tgt gtc tgg cgc ggg     1131
Ser Val Asp Val Gly Lys Asp Ala Ser Phe Ser Cys Val Trp Arg Gly
    320                 325                 330

aac cca ctt cca cgg ata acc tgg acc cgc atg ggt ggc tct cag gtg     1179
Asn Pro Leu Pro Arg Ile Thr Trp Thr Arg Met Gly Gly Ser Gln Val
335                 340                 345                 350

ctg agc tcc ggg ccc acg ctg cgg ctt ccg tcc gtg gca ctg gag gat     1227
Leu Ser Ser Gly Pro Thr Leu Arg Leu Pro Ser Val Ala Leu Glu Asp
                355                 360                 365

gcg ggc gac tat gta tgc agg gct gag ccg agg aga acg ggt ctg gga     1275
Ala Gly Asp Tyr Val Cys Arg Ala Glu Pro Arg Arg Thr Gly Leu Gly
            370                 375                 380

ggc ggc aaa gcg cag gcg agg ctg act gtg aac gca ccc cct gta gtg     1323
Gly Gly Lys Ala Gln Ala Arg Leu Thr Val Asn Ala Pro Pro Val Val
        385                 390                 395

aca gcc ctg caa cct gca cca gcc ttt ctg agg ggt cct gct cgc ctc     1371
Thr Ala Leu Gln Pro Ala Pro Ala Phe Leu Arg Gly Pro Ala Arg Leu
    400                 405                 410

cag tgt gtg gtg ttt gcc tcc cct gcc cca gac tcg gtg gtt tgg tct     1419
Gln Cys Val Val Phe Ala Ser Pro Ala Pro Asp Ser Val Val Trp Ser
415                 420                 425                 430

tgg gac gag ggc ttc ttg gag gca ggc tca ctg ggc agg ttc cta gtg     1467
Trp Asp Glu Gly Phe Leu Glu Ala Gly Ser Leu Gly Arg Phe Leu Val
                435                 440                 445

gaa gcc ttc cca gcc ccg gaa gtg gag ggg gga cag ggc cct ggc ctt     1515
Glu Ala Phe Pro Ala Pro Glu Val Glu Gly Gly Gln Gly Pro Gly Leu
            450                 455                 460

att tct gtg cta cac att tcc gga acc cag gag tcc gac ttt acc acc     1563
Ile Ser Val Leu His Ile Ser Gly Thr Gln Glu Ser Asp Phe Thr Thr
        465                 470                 475

ggc ttc aac tgc agt gcc cgc aac cgg cta gga gag gga cga gtc cag     1611
Gly Phe Asn Cys Ser Ala Arg Asn Arg Leu Gly Glu Gly Arg Val Gln
    480                 485                 490

atc cac ttg ggc cgt aga gac ttg ctg cct act gtc cgg att gtg gct     1659
Ile His Leu Gly Arg Arg Asp Leu Leu Pro Thr Val Arg Ile Val Ala
495                 500                 505                 510
```

```
ggt gca gca tct gca gcc acc tct ctc ctt atg gtc atc act gga gtg      1707
Gly Ala Ala Ser Ala Ala Thr Ser Leu Leu Met Val Ile Thr Gly Val
                515                 520                 525

gtc ctc tgc tgc tgg cgc cat ggc tct ctc tct aag caa aag aac ttg      1755
Val Leu Cys Cys Trp Arg His Gly Ser Leu Ser Lys Gln Lys Asn Leu
            530                 535                 540

gtc cgg atc cca gga agc agc gag ggt tcc agt tca cgt ggc cct gag      1803
Val Arg Ile Pro Gly Ser Ser Glu Gly Ser Ser Ser Arg Gly Pro Glu
        545                 550                 555

gag gag aca ggc agc agt gag gac cgg ggt ccc att gtg cac acc gac      1851
Glu Glu Thr Gly Ser Ser Glu Asp Arg Gly Pro Ile Val His Thr Asp
    560                 565                 570

cac agt gat ttg gtt ctt gag gaa aaa gag gct ctg gag aca aag gat      1899
His Ser Asp Leu Val Leu Glu Glu Lys Glu Ala Leu Glu Thr Lys Asp
575                 580                 585                 590

cca acc aac ggt tac tac agg gtt cga ggg gtc agt gtg agc ctt agc      1947
Pro Thr Asn Gly Tyr Tyr Arg Val Arg Gly Val Ser Val Ser Leu Ser
                595                 600                 605

ctt ggg gaa gct cct gga gga ggc ctc ttc ttg cca ccg ccc tct ccg      1995
Leu Gly Glu Ala Pro Gly Gly Gly Leu Phe Leu Pro Pro Pro Ser Pro
            610                 615                 620

atc ggt ctc cca ggg act cct act tac tat gac ttc aag cca cat ctg      2043
Ile Gly Leu Pro Gly Thr Pro Thr Tyr Tyr Asp Phe Lys Pro His Leu
        625                 630                 635

gac tta gtc cct ccc tgc aga ctg tac aga gcg agg gca ggt tat ctt      2091
Asp Leu Val Pro Pro Cys Arg Leu Tyr Arg Ala Arg Ala Gly Tyr Leu
    640                 645                 650

acc acc ccc cat ccc cgt gcc ttc acc agc tac atg aaa ccc aca tcc      2139
Thr Thr Pro His Pro Arg Ala Phe Thr Ser Tyr Met Lys Pro Thr Ser
655                 660                 665                 670

ttt gga ccc cca gaa ttg agc tct gga act ccc ccc ttc ccg tat gct      2187
Phe Gly Pro Pro Glu Leu Ser Ser Gly Thr Pro Pro Phe Pro Tyr Ala
                675                 680                 685

acc ttg tct cca ccc agc cac cag cgt ctc cag act cat gtg              2229
Thr Leu Ser Pro Pro Ser His Gln Arg Leu Gln Thr His Val
            690                 695                 700

tgaatccatc tctccaagtg aagggtcttg gaatcttctg tttgccatat agtgtgttgt    2289

ccagatttct ggggagtcag aacaagttga tgaccaaccc ctccaaaact gaacattgaa    2349

ggagggaaag atcattacaa gcatcaggac tgttggtgta cactcagttc agccaaagtg    2409

gattctccaa gtgggagcaa tatggccgct ttcccatgag aaagacattc aagatggtga    2469

ctaaatgact aaatactttg cagagggaca aagatgggaa ctagggatat ggatggaagt    2529

agtagagaag atatatgacc atctgcatca agagaaagga taacataaga caaatcaaga    2589

tgaaagaaat aatccacacc ccccccccca ccgcgtcctg gccaataagt atagcctaca    2649

tggctgttca ttatctggga accaaaatgg ccactatctt gactccttcc ttaaagatac    2709

agaaagaatt gaatccaagg aatggggtag ggtggaaata gaagaaatga aggggactct    2769

tgggctaaga atacttatgt ttaataataa aagggggagg caaagaaaaa aaaaaaaaaa    2829

aaaaaaaaaa aaaaaaa                                                   2847
```

```
<210> SEQ ID NO 8
<211> LENGTH: 700
<212> TYPE: PRT
<213> ORGANISM: Mus musculus

<400> SEQUENCE: 8
```

-continued

```
Met Leu Ala Ser Ala Leu Leu Val Phe Leu Cys Cys Phe Lys Gly His
1               5                   10                  15

Ala Gly Ser Ser Pro His Phe Leu Gln Gln Pro Glu Asp Met Val Val
            20                  25                  30

Leu Leu Gly Glu Glu Ala Arg Leu Pro Cys Ala Leu Gly Ala Tyr Arg
        35                  40                  45

Gly Leu Val Gln Trp Thr Lys Asp Gly Leu Ala Leu Gly Gly Glu Arg
    50                  55                  60

Asp Leu Pro Gly Trp Ser Arg Tyr Trp Ile Ser Gly Asn Ser Ala Ser
65                  70                  75                  80

Gly Gln His Asp Leu His Ile Lys Pro Val Glu Leu Glu Asp Glu Ala
                85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Gly Ser Ser Phe His Gln Thr Thr Leu Lys Asp
                165                 170                 175

Lys Ala Thr Gly Thr Val Glu Asn Thr Leu Phe Leu Thr Pro Ser Ser
            180                 185                 190

His Asp Asp Gly Ala Thr Leu Ile Cys Arg Ala Arg Ser Gln Ala Leu
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240

Val Thr Phe Leu Cys Gln Ala Thr Ala Gln Pro Pro Val Thr Gly Tyr
                245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
        275                 280                 285

Glu Val Ser Asn Ala Val Gly Ser Ala Asn Arg Ser Thr Ala Leu Glu
    290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
        355                 360                 365

Asp Tyr Val Cys Arg Ala Glu Pro Arg Arg Thr Gly Leu Gly Gly Gly
    370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
                405                 410                 415

Val Val Phe Ala Ser Pro Ala Pro Asp Ser Val Val Trp Ser Trp Asp
```

```
            420                 425                 430

Glu Gly Phe Leu Glu Ala Gly Ser Leu Gly Arg Phe Leu Val Glu Ala
        435                 440                 445

Phe Pro Ala Pro Glu Val Glu Gly Gly Gln Gly Pro Gly Leu Ile Ser
    450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
                485                 490                 495

Leu Gly Arg Arg Asp Leu Leu Pro Thr Val Arg Ile Val Ala Gly Ala
            500                 505                 510

Ala Ser Ala Ala Thr Ser Leu Leu Met Val Ile Thr Gly Val Val Leu
        515                 520                 525

Cys Cys Trp Arg His Gly Ser Leu Ser Lys Gln Lys Asn Leu Val Arg
    530                 535                 540

Ile Pro Gly Ser Ser Glu Gly Ser Ser Ser Arg Gly Pro Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Arg Val Arg Gly Val Ser Val Ser Leu Ser Leu Gly
        595                 600                 605

Glu Ala Pro Gly Gly Gly Leu Phe Leu Pro Pro Pro Ser Pro Ile Gly
    610                 615                 620

Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
                645                 650                 655

Pro His Pro Arg Ala Phe Thr Ser Tyr Met Lys Pro Thr Ser Phe Gly
            660                 665                 670

Pro Pro Glu Leu Ser Ser Gly Thr Pro Pro Phe Pro Tyr Ala Thr Leu
        675                 680                 685

Ser Pro Pro Ser His Gln Arg Leu Gln Thr His Val
    690                 695                 700


<210> SEQ ID NO 9
<211> LENGTH: 2153
<212> TYPE: DNA
<213> ORGANISM: Homo sapiens
<220> FEATURE:
<221> NAME/KEY: CDS
<222> LOCATION: (199)..(2097)

<400> SEQUENCE: 9

ccgcggaact ggcaggcgtt tcagagcgtc agaggctgcg gatgagcaga cttggaggac      60

tccaggccag agactaggct gggcgaagag tcgagcgtga agggggctcc gggccagggt     120

gacaggaggc gtgcttgaga ggaagaagtt gacgggaagg ccagtgcgac ggcaaatctc     180

gtgaaccttg ggggacga atg ctc agg atg cgg gtc ccc gcc ctc ctc gtc       231
                    Met Leu Arg Met Arg Val Pro Ala Leu Leu Val
                    1               5                   10

ctc ctc ttc tgc ttc aga ggg aga gca ggc ccg tcg ccc cat ttc ctg       279
Leu Leu Phe Cys Phe Arg Gly Arg Ala Gly Pro Ser Pro His Phe Leu
            15                  20                  25

caa cag cca gag gac ctg gtg gtg ctg ctg ggg gag gaa gcc cgg ctg       327
```

```
Gln Gln Pro Glu Asp Leu Val Val Leu Leu Gly Glu Glu Ala Arg Leu
        30                  35                  40

ccg tgt gct ctg ggc gcc tac tgg ggg cta gtt cag tgg act aag agt      375
Pro Cys Ala Leu Gly Ala Tyr Trp Gly Leu Val Gln Trp Thr Lys Ser
    45                  50                  55

ggg ctg gcc cta ggg ggc caa agg gac cta cca ggg tgg tcc cgg tac      423
Gly Leu Ala Leu Gly Gly Gln Arg Asp Leu Pro Gly Trp Ser Arg Tyr
60                  65                  70                  75

tgg ata tca ggg aat gca gcc aat ggc cag cat gac ctc cac att agg      471
Trp Ile Ser Gly Asn Ala Ala Asn Gly Gln His Asp Leu His Ile Arg
                80                  85                  90

ccc gtg gag cta gag gat gaa gca tca tat gaa tgt cag gct aca caa      519
Pro Val Glu Leu Glu Asp Glu Ala Ser Tyr Glu Cys Gln Ala Thr Gln
            95                  100                 105

gca ggc ctc cgc tcc aga cca gcc caa ctg cac gtg ctg gtc ccc cca      567
Ala Gly Leu Arg Ser Arg Pro Ala Gln Leu His Val Leu Val Pro Pro
        110                 115                 120

gaa gcc ccc cag gtg ctg ggc ggc ccc tct gtg tct ctg gtt gct gga      615
Glu Ala Pro Gln Val Leu Gly Gly Pro Ser Val Ser Leu Val Ala Gly
    125                 130                 135

gtt cct gcg aac ctg aca tgt cgg agc cgt ggg gat gcc cgc cct acc      663
Val Pro Ala Asn Leu Thr Cys Arg Ser Arg Gly Asp Ala Arg Pro Thr
140                 145                 150                 155

cct gaa ttg ctg tgg ttc cga gat ggg gtc ctg ttg gat gga gcc acc      711
Pro Glu Leu Leu Trp Phe Arg Asp Gly Val Leu Leu Asp Gly Ala Thr
                160                 165                 170

ttc cat cag acc ctg ctg aag gaa ggg acc cct ggg tca gtg gag agc      759
Phe His Gln Thr Leu Leu Lys Glu Gly Thr Pro Gly Ser Val Glu Ser
            175                 180                 185

acc tta acc ctg acc cct ttc agc cat gat gat gga gcc acc ttt gtc      807
Thr Leu Thr Leu Thr Pro Phe Ser His Asp Asp Gly Ala Thr Phe Val
        190                 195                 200

tgc cgg gcc cgg agc cag gcc ctg ccc aca gga aga gac aca gct atc      855
Cys Arg Ala Arg Ser Gln Ala Leu Pro Thr Gly Arg Asp Thr Ala Ile
    205                 210                 215

aca ctg agc ctg cag tac ccc cca gag gtg act ctg tct gct tcg cca      903
Thr Leu Ser Leu Gln Tyr Pro Pro Glu Val Thr Leu Ser Ala Ser Pro
220                 225                 230                 235

cac act gtg cag gag gga gag aag gtc att ttc ctg tgc cag gcc aca      951
His Thr Val Gln Glu Gly Glu Lys Val Ile Phe Leu Cys Gln Ala Thr
                240                 245                 250

gcc cag cct cct gtc aca ggc tac agg tgg gca aaa ggg ggc tct ccg      999
Ala Gln Pro Pro Val Thr Gly Tyr Arg Trp Ala Lys Gly Gly Ser Pro
            255                 260                 265

gtg ctc ggg gcc cgc ggg cca agg tta gag gtc gtg gca gac gcc tcg     1047
Val Leu Gly Ala Arg Gly Pro Arg Leu Glu Val Val Ala Asp Ala Ser
        270                 275                 280

ttc ctg act gag ccc gtg tcc tgc gag gtc agc aac gcc gtg ggt agc     1095
Phe Leu Thr Glu Pro Val Ser Cys Glu Val Ser Asn Ala Val Gly Ser
    285                 290                 295

gcc aac cgc agt act gcg ctg gat gtg ctg ttt ggg ccg att ctg cag     1143
Ala Asn Arg Ser Thr Ala Leu Asp Val Leu Phe Gly Pro Ile Leu Gln
300                 305                 310                 315

gca aag ccg gag ccc gtg tcc gtg gac gtg ggg gaa gac gct tcc ttc     1191
Ala Lys Pro Glu Pro Val Ser Val Asp Val Gly Glu Asp Ala Ser Phe
                320                 325                 330

agc tgc gcc tgg cgc ggg aac ccg ctt cca cgg gta acc tgg acc cgc     1239
Ser Cys Ala Trp Arg Gly Asn Pro Leu Pro Arg Val Thr Trp Thr Arg
            335                 340                 345
```

```
cgc ggt ggc gcg cag gtg ctg ggc tct gga gcc aca ctg cgt ctt ccg      1287
Arg Gly Gly Ala Gln Val Leu Gly Ser Gly Ala Thr Leu Arg Leu Pro
        350                 355                 360

tcg gtg ggg ccc gag gac gca ggc gac tat gtg tgc aga gct gag gct      1335
Ser Val Gly Pro Glu Asp Ala Gly Asp Tyr Val Cys Arg Ala Glu Ala
    365                 370                 375

ggg cta tcg ggc ctg cgg ggc ggc gcc gcg gag gct cgg ctg act gtg      1383
Gly Leu Ser Gly Leu Arg Gly Gly Ala Ala Glu Ala Arg Leu Thr Val
380                 385                 390                 395

aac gct ccc cca gta gtg acc gcc ctg cac tct gcg cct gcc ttc ctg      1431
Asn Ala Pro Pro Val Val Thr Ala Leu His Ser Ala Pro Ala Phe Leu
                400                 405                 410

agg ggc cct gct cgc ctc cag tgt ctg gtt ttc gcc tct ccc gcc cca      1479
Arg Gly Pro Ala Arg Leu Gln Cys Leu Val Phe Ala Ser Pro Ala Pro
            415                 420                 425

gat gcc gtg gtc tgg tct tgg gat gag ggc ttc ctg gag gcg ggg tcg      1527
Asp Ala Val Val Trp Ser Trp Asp Glu Gly Phe Leu Glu Ala Gly Ser
        430                 435                 440

cag ggc cgg ttc ctg gtg gag aca ttc cct gcc cca gag agc cgc ggg      1575
Gln Gly Arg Phe Leu Val Glu Thr Phe Pro Ala Pro Glu Ser Arg Gly
    445                 450                 455

gga ctg ggt ccg ggc ctg atc tct gtg cta cac att tcg ggg acc cag      1623
Gly Leu Gly Pro Gly Leu Ile Ser Val Leu His Ile Ser Gly Thr Gln
460                 465                 470                 475

gag tct gac ttt agc agg agc ttt aac tgc agt gcc cgg aac cgg ctg      1671
Glu Ser Asp Phe Ser Arg Ser Phe Asn Cys Ser Ala Arg Asn Arg Leu
                480                 485                 490

ggc gag gga ggt gcc cag gcc agc ctg ggc cgt aga gac ttg ctg ccc      1719
Gly Glu Gly Gly Ala Gln Ala Ser Leu Gly Arg Arg Asp Leu Leu Pro
            495                 500                 505

act gtg cgg ata gtg gcc gga gtg gcc gct gcc acc aca act ctc ctt      1767
Thr Val Arg Ile Val Ala Gly Val Ala Ala Ala Thr Thr Thr Leu Leu
        510                 515                 520

atg gtc atc act ggg gtg gcc ctc tgc tgc tgg cgc cac agc aag gcc      1815
Met Val Ile Thr Gly Val Ala Leu Cys Cys Trp Arg His Ser Lys Ala
    525                 530                 535

tca gcc tct ttc tcc gag caa aag aac ctg atg cga atc cct ggc agc      1863
Ser Ala Ser Phe Ser Glu Gln Lys Asn Leu Met Arg Ile Pro Gly Ser
540                 545                 550                 555

agc gac ggc tcc agt tca cga ggt cct gaa gaa gag gag aca ggc agc      1911
Ser Asp Gly Ser Ser Ser Arg Gly Pro Glu Glu Glu Glu Thr Gly Ser
                560                 565                 570

cgc gag gac cgg ggc ccc att gtg cac act gac cac agt gat ctg gtt      1959
Arg Glu Asp Arg Gly Pro Ile Val His Thr Asp His Ser Asp Leu Val
            575                 580                 585

ctg gag gag gaa ggg act ctg gag acc aag gac cca acc aac ggt tac      2007
Leu Glu Glu Glu Gly Thr Leu Glu Thr Lys Asp Pro Thr Asn Gly Tyr
        590                 595                 600

tac aag gtc cga gga gtc agt cca ccc gcg tct cca gac tca cgt gtg      2055
Tyr Lys Val Arg Gly Val Ser Pro Pro Ala Ser Pro Asp Ser Arg Val
    605                 610                 615

aca tct ttc caa tgg aag agt cct ggg atc tcc aac ttg cca              2097
Thr Ser Phe Gln Trp Lys Ser Pro Gly Ile Ser Asn Leu Pro
620                 625                 630

taatggattg ttctgatttc tgaggagcca ggacaagttg gcgaccttac tcctcc        2153
```

<210> SEQ ID NO 10
<211> LENGTH: 633
<212> TYPE: PRT
<213> ORGANISM: Homo sapiens

<400> SEQUENCE: 10

```
Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Gly Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
```

```
                405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Pro Pro Ala Ser Pro Asp Ser Arg Val Thr Ser Phe Gln Trp
    610                 615                 620

Lys Ser Pro Gly Ile Ser Asn Leu Pro
625                 630


<210> SEQ ID NO 11
<211> LENGTH: 2979
<212> TYPE: DNA
<213> ORGANISM: Homo sapiens
<220> FEATURE:
<221> NAME/KEY: CDS
<222> LOCATION: (199)..(2322)

<400> SEQUENCE: 11

ccgcggaact ggcaggcgtt tcagagcgtc agaggctgcg gatgagcaga cttggaggac      60

tccaggccag agactaggct gggcgaagag tcgagcgtga agggggctcc gggccagggt     120

gacaggaggc gtgcttgaga ggaagaagtt gacgggaagg ccagtgcgac ggcaaatctc     180

gtgaaccttg ggggacga atg ctc agg atg cgg gtc ccc gcc ctc ctc gtc       231
                    Met Leu Arg Met Arg Val Pro Ala Leu Leu Val
                    1               5                   10

ctc ctc ttc tgc ttc aga ggg aga gca ggc ccg tcg ccc cat ttc ctg       279
Leu Leu Phe Cys Phe Arg Gly Arg Ala Gly Pro Ser Pro His Phe Leu
            15                  20                  25

caa cag cca gag gac ctg gtg gtg ctg ctg ggg gag gaa gcc cgg ctg       327
Gln Gln Pro Glu Asp Leu Val Val Leu Leu Gly Glu Glu Ala Arg Leu
        30                  35                  40

ccg tgt gct ctg ggc gcc tac tgg ggg cta gtt cag tgg act aag agt       375
Pro Cys Ala Leu Gly Ala Tyr Trp Gly Leu Val Gln Trp Thr Lys Ser
    45                  50                  55

ggg ctg gcc cta ggg ggc caa agg gac cta cca ggg tgg tcc cgg tac       423
Gly Leu Ala Leu Gly Gly Gln Arg Asp Leu Pro Gly Trp Ser Arg Tyr
```

-continued

```
60                65                70                75

tgg ata tca ggg aat gca gcc aat ggc cag cat gac ctc cac att agg      471
Trp Ile Ser Gly Asn Ala Ala Asn Gly Gln His Asp Leu His Ile Arg
                80                85                90

ccc gtg gag cta gag gat gaa gca tca tat gaa tgt cag gct aca caa      519
Pro Val Glu Leu Glu Asp Glu Ala Ser Tyr Glu Cys Gln Ala Thr Gln
            95                100               105

gca ggc ctc cgc tcc aga cca gcc caa ctg cac gtg ctg gtc ccc cca      567
Ala Gly Leu Arg Ser Arg Pro Ala Gln Leu His Val Leu Val Pro Pro
        110               115               120

gaa gcc ccc cag gtg ctg ggc ggc ccc tct gtg tct ctg gtt gct gga      615
Glu Ala Pro Gln Val Leu Gly Gly Pro Ser Val Ser Leu Val Ala Gly
    125               130               135

gtt cct gcg aac ctg aca tgt cgg agc cgt ggg gat gcc cgc cct acc      663
Val Pro Ala Asn Leu Thr Cys Arg Ser Arg Gly Asp Ala Arg Pro Thr
140               145               150               155

cct gaa ttg ctg tgg ttc cga gat ggg gtc ctg ttg gat gga gcc acc      711
Pro Glu Leu Leu Trp Phe Arg Asp Gly Val Leu Leu Asp Gly Ala Thr
                160               165               170

ttc cat cag acc ctg ctg aag gaa ggg acc cct ggg tca gtg gag agc      759
Phe His Gln Thr Leu Leu Lys Glu Gly Thr Pro Gly Ser Val Glu Ser
            175               180               185

acc tta acc ctg acc cct ttc agc cat gat gat gga gcc acc ttt gtc      807
Thr Leu Thr Leu Thr Pro Phe Ser His Asp Asp Gly Ala Thr Phe Val
        190               195               200

tgc cgg gcc cgg agc cag gcc ctg ccc aca gga aga gac aca gct atc      855
Cys Arg Ala Arg Ser Gln Ala Leu Pro Thr Gly Arg Asp Thr Ala Ile
    205               210               215

aca ctg agc ctg cag tac ccc cca gag gtg act ctg tct gct tcg cca      903
Thr Leu Ser Leu Gln Tyr Pro Pro Glu Val Thr Leu Ser Ala Ser Pro
220               225               230               235

cac act gtg cag gag gga gag aag gtc att ttc ctg tgc cag gcc aca      951
His Thr Val Gln Glu Gly Glu Lys Val Ile Phe Leu Cys Gln Ala Thr
                240               245               250

gcc cag cct cct gtc aca ggc tac agg tgg gca aaa ggg ggc tct ccg      999
Ala Gln Pro Pro Val Thr Gly Tyr Arg Trp Ala Lys Gly Gly Ser Pro
            255               260               265

gtg ctc ggg gcc cgc ggg cca agg tta gag gtc gtg gca gac gcc tcg     1047
Val Leu Gly Ala Arg Gly Pro Arg Leu Glu Val Val Ala Asp Ala Ser
        270               275               280

ttc ctg act gag ccc gtg tcc tgc gag gtc agc aac gcc gtg ggt agc     1095
Phe Leu Thr Glu Pro Val Ser Cys Glu Val Ser Asn Ala Val Gly Ser
    285               290               295

gcc aac cgc agt act gcg ctg gat gtg ctg ttt ggg ccg att ctg cag     1143
Ala Asn Arg Ser Thr Ala Leu Asp Val Leu Phe Gly Pro Ile Leu Gln
300               305               310               315

gca aag ccg gag ccc gtg tcc gtg gac gtg ggg gaa gac gct tcc ttc     1191
Ala Lys Pro Glu Pro Val Ser Val Asp Val Gly Glu Asp Ala Ser Phe
                320               325               330

agc tgc gcc tgg cgc ggg aac ccg ctt cca cgg gta acc tgg acc cgc     1239
Ser Cys Ala Trp Arg Gly Asn Pro Leu Pro Arg Val Thr Trp Thr Arg
            335               340               345

cgc ggt ggc gcg cag gtg ctg ggc tct gga gcc aca ctg cgt ctt ccg     1287
Arg Gly Gly Ala Gln Val Leu Gly Ser Gly Ala Thr Leu Arg Leu Pro
        350               355               360

tcg gtg ggg ccc gag gac gca ggc gac tat gtg tgc aga gct gag gct     1335
Ser Val Gly Pro Glu Asp Ala Gly Asp Tyr Val Cys Arg Ala Glu Ala
    365               370               375

ggg cta tcg ggc ctg cgg ggc ggc gcc gcg gag gct cgg ctg act gtg     1383
```

```
Gly Leu Ser Gly Leu Arg Gly Gly Ala Ala Glu Ala Arg Leu Thr Val
380                 385                 390                 395

aac gct ccc cca gta gtg acc gcc ctg cac tct gcg cct gcc ttc ctg      1431
Asn Ala Pro Pro Val Val Thr Ala Leu His Ser Ala Pro Ala Phe Leu
                400                 405                 410

agg ggc cct gct cgc ctc cag tgt ctg gtt ttc gcc tct ccc gcc cca      1479
Arg Gly Pro Ala Arg Leu Gln Cys Leu Val Phe Ala Ser Pro Ala Pro
            415                 420                 425

gat gcc gtg gtc tgg tct tgg gat gag ggc ttc ctg gag gcg ggg tcg      1527
Asp Ala Val Val Trp Ser Trp Asp Glu Gly Phe Leu Glu Ala Gly Ser
        430                 435                 440

cag ggc cgg ttc ctg gtg gag aca ttc cct gcc cca gag agc cgc ggg      1575
Gln Gly Arg Phe Leu Val Glu Thr Phe Pro Ala Pro Glu Ser Arg Gly
    445                 450                 455

gga ctg ggt ccg ggc ctg atc tct gtg cta cac att tcg ggg acc cag      1623
Gly Leu Gly Pro Gly Leu Ile Ser Val Leu His Ile Ser Gly Thr Gln
460                 465                 470                 475

gag tct gac ttt agc agg agc ttt aac tgc agt gcc cgg aac cgg ctg      1671
Glu Ser Asp Phe Ser Arg Ser Phe Asn Cys Ser Ala Arg Asn Arg Leu
                480                 485                 490

ggc gag gga ggt gcc cag gcc agc ctg ggc cgt aga gac ttg ctg ccc      1719
Gly Glu Gly Gly Ala Gln Ala Ser Leu Gly Arg Arg Asp Leu Leu Pro
            495                 500                 505

act gtg cgg ata gtg gcc gga gtg gcc gct gcc acc aca act ctc ctt      1767
Thr Val Arg Ile Val Ala Gly Val Ala Ala Ala Thr Thr Thr Leu Leu
        510                 515                 520

atg gtc atc act ggg gtg gcc ctc tgc tgc tgg cgc cac agc aag gcc      1815
Met Val Ile Thr Gly Val Ala Leu Cys Cys Trp Arg His Ser Lys Ala
    525                 530                 535

tca gcc tct ttc tcc gag caa aag aac ctg atg cga atc cct ggc agc      1863
Ser Ala Ser Phe Ser Glu Gln Lys Asn Leu Met Arg Ile Pro Gly Ser
540                 545                 550                 555

agc gac ggc tcc agt tca cga ggt cct gaa gaa gag gag aca ggc agc      1911
Ser Asp Gly Ser Ser Ser Arg Gly Pro Glu Glu Glu Glu Thr Gly Ser
                560                 565                 570

cgc gag gac cgg ggc ccc att gtg cac act gac cac agt gat ctg gtt      1959
Arg Glu Asp Arg Gly Pro Ile Val His Thr Asp His Ser Asp Leu Val
            575                 580                 585

ctg gag gag gaa ggg act ctg gag acc aag gac cca acc aac ggt tac      2007
Leu Glu Glu Glu Gly Thr Leu Glu Thr Lys Asp Pro Thr Asn Gly Tyr
        590                 595                 600

tac aag gtc cga gga gtc agt gtg agc ctg agc ctt ggc gaa gcc cct      2055
Tyr Lys Val Arg Gly Val Ser Val Ser Leu Ser Leu Gly Glu Ala Pro
    605                 610                 615

gga gga ggt ctc ttc ctg cca cca ccc tcc ccc ctt ggg ccc cca ggg      2103
Gly Gly Gly Leu Phe Leu Pro Pro Pro Ser Pro Leu Gly Pro Pro Gly
620                 625                 630                 635

acc cct acc ttc tat gac ttc aac cca cac ctg ggc atg gtc ccc ccc      2151
Thr Pro Thr Phe Tyr Asp Phe Asn Pro His Leu Gly Met Val Pro Pro
                640                 645                 650

tgc aga ctt tac aga gcc agg gca ggc tat ctc acc aca ccc cac cct      2199
Cys Arg Leu Tyr Arg Ala Arg Ala Gly Tyr Leu Thr Thr Pro His Pro
            655                 660                 665

cga gct ttc acc agc tac atc aaa ccc aca tcc ttt ggg ccc cca gat      2247
Arg Ala Phe Thr Ser Tyr Ile Lys Pro Thr Ser Phe Gly Pro Pro Asp
        670                 675                 680

ctg gcc ccc ggg act ccc ccc ttc cca tat gct gcc ttc ccc aca cct      2295
Leu Ala Pro Gly Thr Pro Pro Phe Pro Tyr Ala Ala Phe Pro Thr Pro
    685                 690                 695
```

```
agc cac ccg cgt ctc cag act cac gtg tgacatcttt ccaatggaag          2342
Ser His Pro Arg Leu Gln Thr His Val
700                 705

agtcctggga tctccaactt gccataatgg attgttctga tttctgagga gccaggacaa  2402

gttggcgacc ttactcctcc aaaactgaac acaaggggag ggaaagatca ttacatttgt  2462

caggagcatt tgtatacagt cagctcagcc aaaggagatg ccccaagtgg gagcaacatg  2522

gccacccaat atgcccacct attccccggt gtaaaagaga ttcaagatgg caggtaggcc  2582

ctttgaggag agatggggac agggcagtgg gtgttgggag tttggggccg ggatggaagt  2642

tgtttctagc cactgaaaga agatatttca agatgaccat ctgcattgag aggaaaggta  2702

gcataggata gatgaagatg aagagcatac caggccccac cctggctctc cctgagggga  2762

actttgctcg gccaatggaa atgcagccaa gatggccata tactccctag gaacccaaga  2822

tggccaccat cttgatttta ctttccttaa agactcagaa agacttggac ccaaggagtg  2882

gggatacagt gagaattacc actgttgggg caaaatattg ggataaaaat atttatgttt  2942

aataataaaa aaaagtcaaa gaggcaaaaa aaaaaaa                            2979


<210> SEQ ID NO 12
<211> LENGTH: 708
<212> TYPE: PRT
<213> ORGANISM: Homo sapiens

<400> SEQUENCE: 12

Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240
```

```
Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Gly Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Val Ser Leu Ser Leu Gly Glu Ala Pro Gly Gly Gly Leu Phe
    610                 615                 620

Leu Pro Pro Pro Ser Pro Leu Gly Pro Pro Gly Thr Pro Thr Phe Tyr
625                 630                 635                 640

Asp Phe Asn Pro His Leu Gly Met Val Pro Pro Cys Arg Leu Tyr Arg
                645                 650                 655

Ala Arg Ala Gly Tyr Leu Thr Thr Pro His Pro Arg Ala Phe Thr Ser
```

```
            660                 665                 670

Tyr Ile Lys Pro Thr Ser Phe Gly Pro Pro Asp Leu Ala Pro Gly Thr
        675                 680                 685

Pro Pro Phe Pro Tyr Ala Ala Phe Pro Thr Pro Ser His Pro Arg Leu
    690                 695                 700

Gln Thr His Val
705


<210> SEQ ID NO 13
<211> LENGTH: 2973
<212> TYPE: DNA
<213> ORGANISM: Homo sapiens
<220> FEATURE:
<221> NAME/KEY: CDS
<222> LOCATION: (199)..(2322)

<400> SEQUENCE: 13

ccgcggaact ggcaggcgtt tcagagcgtc agaggctgcg gatgagcaga cttggaggac      60

tccaggccag agactaggct gggcgaagag tcgagcgtga agggggctcc gggccagggt     120

gacaggaggc gtgcttgaga ggaagaagtt gacgggaagg ccagtgcgac ggcaaatctc     180

gtgaaccttg ggggacga atg ctc agg atg cgg gtc ccc gcc ctc ctc gtc       231
                    Met Leu Arg Met Arg Val Pro Ala Leu Leu Val
                    1               5                   10

ctc ctc ttc tgc ttc aga ggg aga gca ggc ccg tcg ccc cat ttc ctg       279
Leu Leu Phe Cys Phe Arg Gly Arg Ala Gly Pro Ser Pro His Phe Leu
            15                  20                  25

caa cag cca gag gac ctg gtg gtg ctg ctg ggg gag gaa gcc cgg ctg       327
Gln Gln Pro Glu Asp Leu Val Val Leu Leu Gly Glu Glu Ala Arg Leu
        30                  35                  40

ccg tgt gct ctg ggc gcc tac tgg ggg cta gtt cag tgg act aag agt       375
Pro Cys Ala Leu Gly Ala Tyr Trp Gly Leu Val Gln Trp Thr Lys Ser
    45                  50                  55

ggg ctg gcc cta ggg ggc caa agg gac cta cca ggg tgg tcc cgg tac       423
Gly Leu Ala Leu Gly Gly Gln Arg Asp Leu Pro Gly Trp Ser Arg Tyr
60                  65                  70                  75

tgg ata tca ggg aat gca gcc aat ggc cag cat gac ctc cac att agg       471
Trp Ile Ser Gly Asn Ala Ala Asn Gly Gln His Asp Leu His Ile Arg
                80                  85                  90

ccc gtg gag cta gag gat gaa gca tca tat gaa tgt cag gct aca caa       519
Pro Val Glu Leu Glu Asp Glu Ala Ser Tyr Glu Cys Gln Ala Thr Gln
            95                  100                 105

gca ggc ctc cgc tcc aga cca gcc caa ctg cac gtg ctg gtc ccc cca       567
Ala Gly Leu Arg Ser Arg Pro Ala Gln Leu His Val Leu Val Pro Pro
        110                 115                 120

gaa gcc ccc cag gtg ctg ggc ggc ccc tct gtg tct ctg gtt gct gga       615
Glu Ala Pro Gln Val Leu Gly Gly Pro Ser Val Ser Leu Val Ala Gly
    125                 130                 135

gtt cct gcg aac ctg aca tgt cgg agc cgt ggg gat gcc cgc cct acc       663
Val Pro Ala Asn Leu Thr Cys Arg Ser Arg Gly Asp Ala Arg Pro Thr
140                 145                 150                 155

cct gaa ttg ctg tgg ttc cga gat ggg gtc ctg ttg gat gga gcc acc       711
Pro Glu Leu Leu Trp Phe Arg Asp Gly Val Leu Leu Asp Gly Ala Thr
                160                 165                 170

ttt cat cag acc ctg ctg aag gaa ggg acc cct ggg tca gtg gag agc       759
Phe His Gln Thr Leu Leu Lys Glu Gly Thr Pro Gly Ser Val Glu Ser
            175                 180                 185

acc tta acc ctg acc cct ttc agc cat gat gat gga gcc acc ttt gtc       807
Thr Leu Thr Leu Thr Pro Phe Ser His Asp Asp Gly Ala Thr Phe Val
        190                 195                 200
```

```
tgc cgg gcc cgg agc cag gcc ctg ccc aca gga aga gac aca gct atc      855
Cys Arg Ala Arg Ser Gln Ala Leu Pro Thr Gly Arg Asp Thr Ala Ile
    205                 210                 215

aca ctg agc ctg cag tac ccc cca gag gtg act ctg tct gct tcg cca      903
Thr Leu Ser Leu Gln Tyr Pro Pro Glu Val Thr Leu Ser Ala Ser Pro
220                 225                 230                 235

cac act gtg cag gag gga gag aag gtc att ttc ctg tgc cag gcc aca      951
His Thr Val Gln Glu Gly Glu Lys Val Ile Phe Leu Cys Gln Ala Thr
                240                 245                 250

gcc cag cct cct gtc aca ggc tac agg tgg gca aaa ggg ggc tct ccg      999
Ala Gln Pro Pro Val Thr Gly Tyr Arg Trp Ala Lys Gly Gly Ser Pro
            255                 260                 265

gtg ctc ggg gcc cgc ggg cca agg tta gag gtc gtg gca gac gcc tcg     1047
Val Leu Gly Ala Arg Gly Pro Arg Leu Glu Val Val Ala Asp Ala Ser
        270                 275                 280

ttc ctg act gag ccc gtg tcc tgc gag gtc agc aac gcc gtg ggt agc     1095
Phe Leu Thr Glu Pro Val Ser Cys Glu Val Ser Asn Ala Val Gly Ser
    285                 290                 295

gcc aac cgc agt act gcg ctg gat gtg ctg ttt ggg ccg att ctg cag     1143
Ala Asn Arg Ser Thr Ala Leu Asp Val Leu Phe Gly Pro Ile Leu Gln
300                 305                 310                 315

gca aag ccg gag ccc gtg tcc gtg gac gtg ggg gaa gac gct tcc ttc     1191
Ala Lys Pro Glu Pro Val Ser Val Asp Val Gly Glu Asp Ala Ser Phe
                320                 325                 330

agc tgc gcc tgg cgc ggg aac ccg ctt cca cgg gta acc tgg acc cgc     1239
Ser Cys Ala Trp Arg Gly Asn Pro Leu Pro Arg Val Thr Trp Thr Arg
            335                 340                 345

cgc ggt ggc gcg cag gtg ctg ggc tct gga gcc aca ctg cgt ctt ccg     1287
Arg Gly Gly Ala Gln Val Leu Gly Ser Gly Ala Thr Leu Arg Leu Pro
        350                 355                 360

tcg gtg ggg ccc gag gac gca ggc gac tat gtg tgc aga gct gag gct     1335
Ser Val Gly Pro Glu Asp Ala Gly Asp Tyr Val Cys Arg Ala Glu Ala
    365                 370                 375

ggg cta tcg ggc ctg cgg ggc ggc gcc gcg gag gct cgg ctg act gtg     1383
Gly Leu Ser Gly Leu Arg Gly Gly Ala Ala Glu Ala Arg Leu Thr Val
380                 385                 390                 395

aac gct ccc cca gta gtg acc gcc ctg cac tct gcg cct gcc ttc ctg     1431
Asn Ala Pro Pro Val Val Thr Ala Leu His Ser Ala Pro Ala Phe Leu
                400                 405                 410

agg ggc cct gct cgc ctc cag tgt ctg gtt ttc gcc tct ccc gcc cca     1479
Arg Gly Pro Ala Arg Leu Gln Cys Leu Val Phe Ala Ser Pro Ala Pro
            415                 420                 425

gat gcc gtg gtc tgg tct tgg gat gag ggc ttc ctg gag gcg ggg tcg     1527
Asp Ala Val Val Trp Ser Trp Asp Glu Gly Phe Leu Glu Ala Gly Ser
        430                 435                 440

cag ggc cgg ttc ctg gtg gag aca ttc cct gcc cca gag agc cgc ggg     1575
Gln Gly Arg Phe Leu Val Glu Thr Phe Pro Ala Pro Glu Ser Arg Gly
    445                 450                 455

gga ctg ggt ccg ggc ctg atc tct gtg cta cac att tcg ggg acc cag     1623
Gly Leu Gly Pro Gly Leu Ile Ser Val Leu His Ile Ser Gly Thr Gln
460                 465                 470                 475

gag tct gac ttt agc agg agc ttt aac tgc agt gcc cgg aac cgg ctg     1671
Glu Ser Asp Phe Ser Arg Ser Phe Asn Cys Ser Ala Arg Asn Arg Leu
                480                 485                 490

ggc gag gga ggt gcc cag gcc agc ctg ggc cgt aga gac ttg ctg ccc     1719
Gly Glu Gly Gly Ala Gln Ala Ser Leu Gly Arg Arg Asp Leu Leu Pro
            495                 500                 505

act gtg cgg ata gtg gcc gga gtg gcc gct gcc acc aca act ctc ctt     1767
Thr Val Arg Ile Val Ala Gly Val Ala Ala Ala Thr Thr Thr Leu Leu
```

```
        510                 515                 520

atg gtc atc act ggg gtg gcc ctc tgc tgc tgg cgc cac agc aag gcc     1815
Met Val Ile Thr Gly Val Ala Leu Cys Cys Trp Arg His Ser Lys Ala
    525                 530                 535

tca gcc tct ttc tcc gag caa aag aac ctg atg cga atc cct ggc agc     1863
Ser Ala Ser Phe Ser Glu Gln Lys Asn Leu Met Arg Ile Pro Gly Ser
540                 545                 550                 555

agc gac ggc tcc agt tca cga ggt cct gaa gaa gag gag aca ggc agc     1911
Ser Asp Gly Ser Ser Ser Arg Gly Pro Glu Glu Glu Glu Thr Gly Ser
                560                 565                 570

cgc gag gac cgg ggc ccc att gtg cac act gac cac agt gat ctg gtt     1959
Arg Glu Asp Arg Gly Pro Ile Val His Thr Asp His Ser Asp Leu Val
            575                 580                 585

ctg gag gag gaa ggg act ctg gag acc aag gac cca acc aac ggt tac     2007
Leu Glu Glu Glu Gly Thr Leu Glu Thr Lys Asp Pro Thr Asn Gly Tyr
        590                 595                 600

tac aag gtc cga gga gtc agt gtg agc ctg agc ctt ggc gaa gcc cct     2055
Tyr Lys Val Arg Gly Val Ser Val Ser Leu Ser Leu Gly Glu Ala Pro
    605                 610                 615

gga gga ggt ctc ttc ctg cca cca ccc tcc ccc ctt ggg ccc cca ggg     2103
Gly Gly Gly Leu Phe Leu Pro Pro Pro Ser Pro Leu Gly Pro Pro Gly
620                 625                 630                 635

acc cct acc ttc tat gac ttc aac cca cac ctg ggc atg gtc ccc ccc     2151
Thr Pro Thr Phe Tyr Asp Phe Asn Pro His Leu Gly Met Val Pro Pro
                640                 645                 650

tgc aga ctt tac aga gcc agg gca ggc tat ctc acc aca ccc cac cct     2199
Cys Arg Leu Tyr Arg Ala Arg Ala Gly Tyr Leu Thr Thr Pro His Pro
            655                 660                 665

cga gct ttc acc agc tac atc aaa ccc aca tcc ttt ggg ccc cca gat     2247
Arg Ala Phe Thr Ser Tyr Ile Lys Pro Thr Ser Phe Gly Pro Pro Asp
        670                 675                 680

ctg gcc ccc ggg act ccc ccc ttc cca tat gct gcc ttc ccc aca cct     2295
Leu Ala Pro Gly Thr Pro Pro Phe Pro Tyr Ala Ala Phe Pro Thr Pro
    685                 690                 695

agc cac ccg cgt ctc cag act cac gtg tgacatcttt ccaatggaag           2342
Ser His Pro Arg Leu Gln Thr His Val
700                 705

agtcctggga tctccaactt gccataatgg attgttctga tttctgagga gccaggacaa   2402

gttggcgacc ttactcctcc aaaactgaac acaaggggag ggaaagatca ttacatttgt   2462

caggagcatt tgtatacagt cagctcagcc aaaggagatg ccccaagtgg gagcaacatg   2522

gccacccaat atgcccacct attccccggt gtaaaagaga ttcaagatgg caggtaggcc   2582

ctttgaggag agatggggac agggcagtgg gtgttgggag tttggggccg ggatggaagt   2642

tgtttctagc cactgaaaga agatatttca agatgaccat ctgcattgag aggaaaggta   2702

gcataggata gatgaagatg aagagcatac caggccccac cctggctctc cctgagggga   2762

actttgctcg gccaatggaa atgcagccaa gatggccata tactccctag gaacccaaaa   2822

tggccaccat cttgatttta ctttccttaa agactcagaa agacttggac ccaaggagtg   2882

gggatacagt gagaattacc actgttgggg caaaatattg ggataaaaat atttatgttt   2942

aataataaaa aaaagtcaaa gagaaaaaaa a                                  2973


<210> SEQ ID NO 14
<211> LENGTH: 708
<212> TYPE: PRT
<213> ORGANISM: Homo sapiens

<400> SEQUENCE: 14
```

```
Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Gly Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415
```

```
Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Val Ser Leu Ser Leu Gly Glu Ala Pro Gly Gly Gly Leu Phe
    610                 615                 620

Leu Pro Pro Pro Ser Pro Leu Gly Pro Pro Gly Thr Pro Thr Phe Tyr
625                 630                 635                 640

Asp Phe Asn Pro His Leu Gly Met Val Pro Pro Cys Arg Leu Tyr Arg
                645                 650                 655

Ala Arg Ala Gly Tyr Leu Thr Thr Pro His Pro Arg Ala Phe Thr Ser
            660                 665                 670

Tyr Ile Lys Pro Thr Ser Phe Gly Pro Pro Asp Leu Ala Pro Gly Thr
        675                 680                 685

Pro Pro Phe Pro Tyr Ala Ala Phe Pro Thr Pro Ser His Pro Arg Leu
    690                 695                 700

Gln Thr His Val
705


<210> SEQ ID NO 15
<211> LENGTH: 1969
<212> TYPE: DNA
<213> ORGANISM: Homo sapiens
<220> FEATURE:
<221> NAME/KEY: CDS
<222> LOCATION: (15)..(1913)

<400> SEQUENCE: 15

accttggggg acga atg ctc agg atg cgg gtc ccc gcc ctc ctc gtc ctc        50
                Met Leu Arg Met Arg Val Pro Ala Leu Leu Val Leu
                1               5                   10

ctc ttc tgc ttc aga ggg aga gca ggc ccg tcg ccc cat ttc ctg caa        98
Leu Phe Cys Phe Arg Gly Arg Ala Gly Pro Ser Pro His Phe Leu Gln
        15                  20                  25

cag cca gag gac ctg gtg gtg ctg ctg ggg gag gaa gcc cgg ctg ccg       146
Gln Pro Glu Asp Leu Val Val Leu Leu Gly Glu Glu Ala Arg Leu Pro
    30                  35                  40
```

```
tgt gct ctg ggc gcc tac tgg ggg cta gtt cag tgg act aag agt ggg      194
Cys Ala Leu Gly Ala Tyr Trp Gly Leu Val Gln Trp Thr Lys Ser Gly
45                  50                  55                  60

ctg gcc cta ggg ggc caa agg gac cta cca ggg tgg tcc cgg tac tgg      242
Leu Ala Leu Gly Gly Gln Arg Asp Leu Pro Gly Trp Ser Arg Tyr Trp
                65                  70                  75

ata tca ggg aat gca gcc aat ggc cag cat gac ctc cac att agg ccc      290
Ile Ser Gly Asn Ala Ala Asn Gly Gln His Asp Leu His Ile Arg Pro
            80                  85                  90

gtg gag cta gag gat gaa gca tca tat gaa tgt cag gct aca caa gca      338
Val Glu Leu Glu Asp Glu Ala Ser Tyr Glu Cys Gln Ala Thr Gln Ala
        95                  100                 105

ggc ctc cgc tcc aga cca gcc caa ctg cac gtg ctg gtc ccc cca gaa      386
Gly Leu Arg Ser Arg Pro Ala Gln Leu His Val Leu Val Pro Pro Glu
    110                 115                 120

gcc ccc cag gtg ctg ggc ggc ccc tct gtg tct ctg gtt gct gga gtt      434
Ala Pro Gln Val Leu Gly Gly Pro Ser Val Ser Leu Val Ala Gly Val
125                 130                 135                 140

cct gcg aac ctg aca tgt cgg agc cgt ggg gat gcc cgc cct acc cct      482
Pro Ala Asn Leu Thr Cys Arg Ser Arg Gly Asp Ala Arg Pro Thr Pro
                145                 150                 155

gaa ttg ctg tgg ttc cga gat ggg gtc ctg ttg gat gga gcc acc ttc      530
Glu Leu Leu Trp Phe Arg Asp Gly Val Leu Leu Asp Gly Ala Thr Phe
            160                 165                 170

cat cag acc ctg ctg aag gaa ggg acc cct ggg tca gtg gag agc acc      578
His Gln Thr Leu Leu Lys Glu Gly Thr Pro Gly Ser Val Glu Ser Thr
        175                 180                 185

tta acc ctg acc cct ttc agc cat gat gat gga gcc acc ctt gtc tgc      626
Leu Thr Leu Thr Pro Phe Ser His Asp Asp Gly Ala Thr Leu Val Cys
    190                 195                 200

cgg gcc cgg agc cag gcc ctg ccc aca gga aga gac aca gct atc aca      674
Arg Ala Arg Ser Gln Ala Leu Pro Thr Gly Arg Asp Thr Ala Ile Thr
205                 210                 215                 220

ctg agc ctg cag tac ccc cca gag gtg act ctg tct gct tcg cca cac      722
Leu Ser Leu Gln Tyr Pro Pro Glu Val Thr Leu Ser Ala Ser Pro His
                225                 230                 235

act gtg cag gag gga gag aag gtc att ttc ctg tgc cag gcc aca gcc      770
Thr Val Gln Glu Gly Glu Lys Val Ile Phe Leu Cys Gln Ala Thr Ala
            240                 245                 250

cag cct cct gtc aca ggc tac agg tgg gca aaa ggg ggc tct ccg gtg      818
Gln Pro Pro Val Thr Gly Tyr Arg Trp Ala Lys Gly Gly Ser Pro Val
        255                 260                 265

ctc ggg gcc cgc ggg cca agg tta gag gtc gtg gca gac gcc tcg ttc      866
Leu Gly Ala Arg Gly Pro Arg Leu Glu Val Val Ala Asp Ala Ser Phe
    270                 275                 280

ctg act gag ccc gtg tcc tgc gag gtc agc aac gcc gtg ggt agc gcc      914
Leu Thr Glu Pro Val Ser Cys Glu Val Ser Asn Ala Val Gly Ser Ala
285                 290                 295                 300

aac cgc agt act gcg ctg gat gtg ctg ttt ggg ccg att ctg cag gca      962
Asn Arg Ser Thr Ala Leu Asp Val Leu Phe Gly Pro Ile Leu Gln Ala
                305                 310                 315

aag ccg gag ccc gtg tcc gtg gac gtg ggg gaa gac gct tcc ttc agc     1010
Lys Pro Glu Pro Val Ser Val Asp Val Gly Glu Asp Ala Ser Phe Ser
            320                 325                 330

tgc gcc tgg cgc ggg aat ccg ctt cca cgg gta acc tgg acc cgc cgc     1058
Cys Ala Trp Arg Gly Asn Pro Leu Pro Arg Val Thr Trp Thr Arg Arg
        335                 340                 345

ggt ggc gcg cag gtg ctg ggc tct gga gcc aca ctg cgt ctt ccg tcg     1106
Gly Gly Ala Gln Val Leu Gly Ser Gly Ala Thr Leu Arg Leu Pro Ser
```

```
    350                 355                 360

gtg ggg ccc gag gac gca gac gac tat gtg tgc aga gct gag gct ggg     1154
Val Gly Pro Glu Asp Ala Asp Asp Tyr Val Cys Arg Ala Glu Ala Gly
365                 370                 375                 380

cta tcg ggc ctg cgg ggc ggc gcc gcg gag gct cgg ctg act gtg aac     1202
Leu Ser Gly Leu Arg Gly Gly Ala Ala Glu Ala Arg Leu Thr Val Asn
                385                 390                 395

gct ccc cca gta gtg acc gcc ctg cac tct gcg cct gcc ttc ctg agg     1250
Ala Pro Pro Val Val Thr Ala Leu His Ser Ala Pro Ala Phe Leu Arg
            400                 405                 410

ggc cct gct cgc ctc cag tgt ctg gtt ttc gcc tct ccc gcc cca gat     1298
Gly Pro Ala Arg Leu Gln Cys Leu Val Phe Ala Ser Pro Ala Pro Asp
        415                 420                 425

gcc gtg gtc tgg tct tgg gat gag ggc ttc ctg gag gcg ggg tcg cag     1346
Ala Val Val Trp Ser Trp Asp Glu Gly Phe Leu Glu Ala Gly Ser Gln
    430                 435                 440

ggt cgg ttc ctg gtg gag aca ttc cct gcc cca gag agc cgc ggg gga     1394
Gly Arg Phe Leu Val Glu Thr Phe Pro Ala Pro Glu Ser Arg Gly Gly
445                 450                 455                 460

ctg ggt ccg ggc ctg atc tct gtg cta cac att tcg ggg acc cag gag     1442
Leu Gly Pro Gly Leu Ile Ser Val Leu His Ile Ser Gly Thr Gln Glu
                465                 470                 475

tct gac ttt agc agg agc ttt aac tgc agt gcc cgg aac cgg ctg ggc     1490
Ser Asp Phe Ser Arg Ser Phe Asn Cys Ser Ala Arg Asn Arg Leu Gly
            480                 485                 490

gag gga ggt gcc cag gcc agc ctg ggc cgt aga gac ttg ctg ccc act     1538
Glu Gly Gly Ala Gln Ala Ser Leu Gly Arg Arg Asp Leu Leu Pro Thr
        495                 500                 505

gtg cgg ata gtg gcc gga gtg gtc gct gcc acc aca act ctc ctt atg     1586
Val Arg Ile Val Ala Gly Val Val Ala Ala Thr Thr Thr Leu Leu Met
    510                 515                 520

gtc atc act ggg gtg gcc ctc tgc tgc tgg cgc cac agc aag gcc tca     1634
Val Ile Thr Gly Val Ala Leu Cys Cys Trp Arg His Ser Lys Ala Ser
525                 530                 535                 540

gcc tct ttc tcc gag caa aag aac ctg atg cga atc cct ggc agc agc     1682
Ala Ser Phe Ser Glu Gln Lys Asn Leu Met Arg Ile Pro Gly Ser Ser
                545                 550                 555

gac ggc tcc agt tca cga ggt cct gaa gaa gag gag aca ggc agc cgc     1730
Asp Gly Ser Ser Ser Arg Gly Pro Glu Glu Glu Glu Thr Gly Ser Arg
            560                 565                 570

gag gac cgg ggc ccc att gtg cac act gac cac agt gat ctg gtt ctg     1778
Glu Asp Arg Gly Pro Ile Val His Thr Asp His Ser Asp Leu Val Leu
        575                 580                 585

gag gag gaa ggg act ctg gag acc aag gac cca acc aac ggt tac tac     1826
Glu Glu Glu Gly Thr Leu Glu Thr Lys Asp Pro Thr Asn Gly Tyr Tyr
    590                 595                 600

aag gtc cga gga gtc agt cca ccc gcg tct cca gac tca cgt gtg aca     1874
Lys Val Arg Gly Val Ser Pro Pro Ala Ser Pro Asp Ser Arg Val Thr
605                 610                 615                 620

tct ttc caa tgg aag agt cct ggg atc tcc aac ttg cca taatggattg      1923
Ser Phe Gln Trp Lys Ser Pro Gly Ile Ser Asn Leu Pro
                625                 630

ttctgatttc tgaggagcca ggacaagttg gcgaccttac tcctcc                  1969


<210> SEQ ID NO 16
<211> LENGTH: 633
<212> TYPE: PRT
<213> ORGANISM: Homo sapiens

<400> SEQUENCE: 16
```

```
Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Leu Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Asp Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415
```

```
Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Val Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Pro Pro Ala Ser Pro Asp Ser Arg Val Thr Ser Phe Gln Trp
    610                 615                 620

Lys Ser Pro Gly Ile Ser Asn Leu Pro
625                 630


<210> SEQ ID NO 17
<211> LENGTH: 2003
<212> TYPE: DNA
<213> ORGANISM: Homo sapiens
<220> FEATURE:
<221> NAME/KEY: CDS
<222> LOCATION: (199)..(1947)

<400> SEQUENCE: 17

ccgcggaact ggcaggcgtt tcagagcgtc agaggctgcg gatgagcaga cttggaggac      60

tccaggccag agactaggct gggcgaagag tcgagcgtga agggggctcc gggccagggt     120

gacaggaggc gtgcttgaga ggaagaagtt gacgggaagg ccagtgcgac ggcaaatctc     180

gtgaaccttg ggggacga atg ctc agg atg cgg gtc ccc gcc ctc ctc gtc       231
                    Met Leu Arg Met Arg Val Pro Ala Leu Leu Val
                    1               5                   10

ctc ctc ttc tgc ttc aga ggg aga gca ggg tgg tcc cgg tac tgg ata       279
Leu Leu Phe Cys Phe Arg Gly Arg Ala Gly Trp Ser Arg Tyr Trp Ile
            15                  20                  25

tca ggg aat gca gcc aat ggc cag cat gac ctc cac att agg ccc gtg       327
Ser Gly Asn Ala Ala Asn Gly Gln His Asp Leu His Ile Arg Pro Val
        30                  35                  40

gag cta gag gat gaa gca tca tat gaa tgt cag gct aca caa gca ggc       375
Glu Leu Glu Asp Glu Ala Ser Tyr Glu Cys Gln Ala Thr Gln Ala Gly
    45                  50                  55

ctc cgc tcc aga cca gcc caa ctg cac gtg ctg gtc ccc cca gaa gcc       423
Leu Arg Ser Arg Pro Ala Gln Leu His Val Leu Val Pro Pro Glu Ala
60                  65                  70                  75
```

```
ccc cag gtg ctg ggc ggc ccc tct gtg tct ctg gtt gct gga gtt cct      471
Pro Gln Val Leu Gly Gly Pro Ser Val Ser Leu Val Ala Gly Val Pro
                80                  85                  90

gcg aac ctg aca tgt cgg agc cgt ggg gat gcc cgc cct acc cct gaa      519
Ala Asn Leu Thr Cys Arg Ser Arg Gly Asp Ala Arg Pro Thr Pro Glu
            95                  100                 105

ttg ctg tgg ttc cga gat ggg gtc ctg ttg gat gga gcc acc ttc cat      567
Leu Leu Trp Phe Arg Asp Gly Val Leu Leu Asp Gly Ala Thr Phe His
        110                 115                 120

cag acc ctg ctg aag gaa ggg acc cct ggg tca gtg gag agc acc tta      615
Gln Thr Leu Leu Lys Glu Gly Thr Pro Gly Ser Val Glu Ser Thr Leu
    125                 130                 135

acc ctg acc cct ttc agc cat gat gat gga gcc acc ttt gtc tgc cgg      663
Thr Leu Thr Pro Phe Ser His Asp Asp Gly Ala Thr Phe Val Cys Arg
140                 145                 150                 155

gcc cgg agc cag gcc ctg ccc aca gga aga gac aca gct atc aca ctg      711
Ala Arg Ser Gln Ala Leu Pro Thr Gly Arg Asp Thr Ala Ile Thr Leu
                160                 165                 170

agc ctg cag tac ccc cca gag gtg act ctg tct gct tcg cca cac act      759
Ser Leu Gln Tyr Pro Pro Glu Val Thr Leu Ser Ala Ser Pro His Thr
            175                 180                 185

gtg cag gag gga gag aag gtc att ttc ctg tgc cag gcc aca gcc cag      807
Val Gln Glu Gly Glu Lys Val Ile Phe Leu Cys Gln Ala Thr Ala Gln
        190                 195                 200

cct cct gtc aca ggc tac agg tgg gca aaa ggg ggc tct ccg gtg ctc      855
Pro Pro Val Thr Gly Tyr Arg Trp Ala Lys Gly Gly Ser Pro Val Leu
    205                 210                 215

ggg gcc cgc ggg cca agg tta gag gtc gtg gca gac gcc tcg ttc ctg      903
Gly Ala Arg Gly Pro Arg Leu Glu Val Val Ala Asp Ala Ser Phe Leu
220                 225                 230                 235

act gag ccc gtg tcc tgc gag gtc agc aac gcc gtg ggt agc gcc aac      951
Thr Glu Pro Val Ser Cys Glu Val Ser Asn Ala Val Gly Ser Ala Asn
                240                 245                 250

cgc agt act gcg ctg gat gtg ctg ttt ggg ccg att ctg cag gca aag      999
Arg Ser Thr Ala Leu Asp Val Leu Phe Gly Pro Ile Leu Gln Ala Lys
            255                 260                 265

ccg gag ccc gtg tcc gtg gac gtg ggg gaa gac gct tcc ttc agc tgc     1047
Pro Glu Pro Val Ser Val Asp Val Gly Glu Asp Ala Ser Phe Ser Cys
        270                 275                 280

gcc tgg cgc ggg aac ccg ctt cca cgg gta acc tgg acc cgc cgc ggt     1095
Ala Trp Arg Gly Asn Pro Leu Pro Arg Val Thr Trp Thr Arg Arg Gly
    285                 290                 295

ggc gcg cag gtg ctg ggc tct gga gcc aca ctg cgt ctt ccg tcg gtg     1143
Gly Ala Gln Val Leu Gly Ser Gly Ala Thr Leu Arg Leu Pro Ser Val
300                 305                 310                 315

ggg ccc gag gac gca ggc gac tat gtg tgc aga gct gag gct ggg cta     1191
Gly Pro Glu Asp Ala Gly Asp Tyr Val Cys Arg Ala Glu Ala Gly Leu
                320                 325                 330

tcg ggc ctg cgg ggc ggc gcc gcg gag gct cgg ctg act gtg aac gct     1239
Ser Gly Leu Arg Gly Gly Ala Ala Glu Ala Arg Leu Thr Val Asn Ala
            335                 340                 345

ccc cca gta gtg acc gcc ctg cac tct gcg cct gcc ttc ctg agg ggc     1287
Pro Pro Val Val Thr Ala Leu His Ser Ala Pro Ala Phe Leu Arg Gly
        350                 355                 360

cct gct cgc ctc cag tgt ctg gtt ttc gcc tct ccc gcc cca gat gcc     1335
Pro Ala Arg Leu Gln Cys Leu Val Phe Ala Ser Pro Ala Pro Asp Ala
    365                 370                 375

gtg gtc tgg tct tgg gat gag ggc ttc ctg gag gcg ggg tcg cag ggc     1383
Val Val Trp Ser Trp Asp Glu Gly Phe Leu Glu Ala Gly Ser Gln Gly
380                 385                 390                 395
```

```
cgg ttc ctg gtg gag aca ttc cct gcc cca gag agc cgc ggg gga ctg     1431
Arg Phe Leu Val Glu Thr Phe Pro Ala Pro Glu Ser Arg Gly Gly Leu
                400                 405                 410

ggt ccg ggc ctg atc tct gtg cta cac att tcg ggg acc cag gag tct     1479
Gly Pro Gly Leu Ile Ser Val Leu His Ile Ser Gly Thr Gln Glu Ser
            415                 420                 425

gac ttt agc agg agc ttt aac tgc agt gcc cgg aac cgg ctg ggc gag     1527
Asp Phe Ser Arg Ser Phe Asn Cys Ser Ala Arg Asn Arg Leu Gly Glu
        430                 435                 440

gga ggt gcc cag gcc agc ctg ggc cgt aga gac ttg ctg ccc act gtg     1575
Gly Gly Ala Gln Ala Ser Leu Gly Arg Arg Asp Leu Leu Pro Thr Val
    445                 450                 455

cgg ata gtg gcc gga gtg gcc gct gcc acc aca act ctc ctt atg gtc     1623
Arg Ile Val Ala Gly Val Ala Ala Ala Thr Thr Thr Leu Leu Met Val
460                 465                 470                 475

atc act ggg gtg gcc ctc tgc tgc tgg cgc cac agc aag gcc tca gcc     1671
Ile Thr Gly Val Ala Leu Cys Cys Trp Arg His Ser Lys Ala Ser Ala
                480                 485                 490

tct ttc tcc gag caa aag aac ctg atg cga atc cct ggc agc agc gac     1719
Ser Phe Ser Glu Gln Lys Asn Leu Met Arg Ile Pro Gly Ser Ser Asp
            495                 500                 505

ggc tcc agt tca cga ggt cct gaa gaa gag gag aca ggc agc cgc gag     1767
Gly Ser Ser Ser Arg Gly Pro Glu Glu Glu Glu Thr Gly Ser Arg Glu
        510                 515                 520

gac cgg ggc ccc att gtg cac act gac cac agt gat ctg gtt ctg gag     1815
Asp Arg Gly Pro Ile Val His Thr Asp His Ser Asp Leu Val Leu Glu
    525                 530                 535

gag gaa ggg act ctg gag acc aag gac cca acc aac ggt tac tac aag     1863
Glu Glu Gly Thr Leu Glu Thr Lys Asp Pro Thr Asn Gly Tyr Tyr Lys
540                 545                 550                 555

gtc cga gga gtc agt cca ccc gcg tct cca gac tca cgt gtg aca tct     1911
Val Arg Gly Val Ser Pro Pro Ala Ser Pro Asp Ser Arg Val Thr Ser
                560                 565                 570

ttc caa tgg aag agt cct ggg atc tcc aac ttg cca taatggattg          1957
Phe Gln Trp Lys Ser Pro Gly Ile Ser Asn Leu Pro
            575                 580

ttctgatttc tgaggagcca ggacaagttg gcgaccttac tcctcc                  2003


<210> SEQ ID NO 18
<211> LENGTH: 583
<212> TYPE: PRT
<213> ORGANISM: Homo sapiens

<400> SEQUENCE: 18

Met Leu Arg Met Arg Val Pro Ala Leu Leu Val Leu Leu Phe Cys Phe
1               5                   10                  15

Arg Gly Arg Ala Gly Trp Ser Arg Tyr Trp Ile Ser Gly Asn Ala Ala
            20                  25                  30

Asn Gly Gln His Asp Leu His Ile Arg Pro Val Glu Leu Glu Asp Glu
        35                  40                  45

Ala Ser Tyr Glu Cys Gln Ala Thr Gln Ala Gly Leu Arg Ser Arg Pro
    50                  55                  60

Ala Gln Leu His Val Leu Val Pro Pro Glu Ala Pro Gln Val Leu Gly
65                  70                  75                  80

Gly Pro Ser Val Ser Leu Val Ala Gly Val Pro Ala Asn Leu Thr Cys
                85                  90                  95

Arg Ser Arg Gly Asp Ala Arg Pro Thr Pro Glu Leu Leu Trp Phe Arg
            100                 105                 110
```

```
Asp Gly Val Leu Leu Asp Gly Ala Thr Phe His Gln Thr Leu Leu Lys
        115                 120                 125

Glu Gly Thr Pro Gly Ser Val Glu Ser Thr Leu Thr Leu Thr Pro Phe
    130                 135                 140

Ser His Asp Asp Gly Ala Thr Phe Val Cys Arg Ala Arg Ser Gln Ala
145                 150                 155                 160

Leu Pro Thr Gly Arg Asp Thr Ala Ile Thr Leu Ser Leu Gln Tyr Pro
                165                 170                 175

Pro Glu Val Thr Leu Ser Ala Ser Pro His Thr Val Gln Glu Gly Glu
            180                 185                 190

Lys Val Ile Phe Leu Cys Gln Ala Thr Ala Gln Pro Pro Val Thr Gly
        195                 200                 205

Tyr Arg Trp Ala Lys Gly Gly Ser Pro Val Leu Gly Ala Arg Gly Pro
    210                 215                 220

Arg Leu Glu Val Val Ala Asp Ala Ser Phe Leu Thr Glu Pro Val Ser
225                 230                 235                 240

Cys Glu Val Ser Asn Ala Val Gly Ser Ala Asn Arg Ser Thr Ala Leu
                245                 250                 255

Asp Val Leu Phe Gly Pro Ile Leu Gln Ala Lys Pro Glu Pro Val Ser
            260                 265                 270

Val Asp Val Gly Glu Asp Ala Ser Phe Ser Cys Ala Trp Arg Gly Asn
        275                 280                 285

Pro Leu Pro Arg Val Thr Trp Thr Arg Arg Gly Gly Ala Gln Val Leu
    290                 295                 300

Gly Ser Gly Ala Thr Leu Arg Leu Pro Ser Val Gly Pro Glu Asp Ala
305                 310                 315                 320

Gly Asp Tyr Val Cys Arg Ala Glu Ala Gly Leu Ser Gly Leu Arg Gly
                325                 330                 335

Gly Ala Ala Glu Ala Arg Leu Thr Val Asn Ala Pro Pro Val Val Thr
            340                 345                 350

Ala Leu His Ser Ala Pro Ala Phe Leu Arg Gly Pro Ala Arg Leu Gln
        355                 360                 365

Cys Leu Val Phe Ala Ser Pro Ala Pro Asp Ala Val Val Trp Ser Trp
    370                 375                 380

Asp Glu Gly Phe Leu Glu Ala Gly Ser Gln Gly Arg Phe Leu Val Glu
385                 390                 395                 400

Thr Phe Pro Ala Pro Glu Ser Arg Gly Gly Leu Gly Pro Gly Leu Ile
                405                 410                 415

Ser Val Leu His Ile Ser Gly Thr Gln Glu Ser Asp Phe Ser Arg Ser
            420                 425                 430

Phe Asn Cys Ser Ala Arg Asn Arg Leu Gly Glu Gly Gly Ala Gln Ala
        435                 440                 445

Ser Leu Gly Arg Arg Asp Leu Leu Pro Thr Val Arg Ile Val Ala Gly
    450                 455                 460

Val Ala Ala Ala Thr Thr Thr Leu Leu Met Val Ile Thr Gly Val Ala
465                 470                 475                 480

Leu Cys Cys Trp Arg His Ser Lys Ala Ser Ala Ser Phe Ser Glu Gln
                485                 490                 495

Lys Asn Leu Met Arg Ile Pro Gly Ser Ser Asp Gly Ser Ser Ser Arg
            500                 505                 510

Gly Pro Glu Glu Glu Glu Thr Gly Ser Arg Glu Asp Arg Gly Pro Ile
        515                 520                 525
```

```
Val His Thr Asp His Ser Asp Leu Val Leu Glu Glu Glu Gly Thr Leu
    530                 535                 540

Glu Thr Lys Asp Pro Thr Asn Gly Tyr Tyr Lys Val Arg Gly Val Ser
545                 550                 555                 560

Pro Pro Ala Ser Pro Asp Ser Arg Val Thr Ser Phe Gln Trp Lys Ser
                565                 570                 575

Pro Gly Ile Ser Asn Leu Pro
            580


<210> SEQ ID NO 19
<211> LENGTH: 1819
<212> TYPE: DNA
<213> ORGANISM: Homo sapiens
<220> FEATURE:
<221> NAME/KEY: CDS
<222> LOCATION: (15)..(1763)

<400> SEQUENCE: 19

accttggggg acga atg ctc tgg atg cgg gtc ccc gcc ctc ctc gtc ctc       50
                Met Leu Trp Met Arg Val Pro Ala Leu Leu Val Leu
                1               5                   10

ctc ttc tgc ttc aga ggg aga gca ggg tgg tcc cgg tac tgg ata tca       98
Leu Phe Cys Phe Arg Gly Arg Ala Gly Trp Ser Arg Tyr Trp Ile Ser
        15                  20                  25

ggg aat gca gcc aat ggc cag cat gac ctc cac att agg ccc gtg gag      146
Gly Asn Ala Ala Asn Gly Gln His Asp Leu His Ile Arg Pro Val Glu
    30                  35                  40

cta gag gat gaa gca tca tat gaa tgt cag gct aca caa gca ggc ctc      194
Leu Glu Asp Glu Ala Ser Tyr Glu Cys Gln Ala Thr Gln Ala Gly Leu
45                  50                  55                  60

cgc tcc aga cca gcc caa ctg cac gtg ctg gtc ccc cca gaa gcc ccc      242
Arg Ser Arg Pro Ala Gln Leu His Val Leu Val Pro Pro Glu Ala Pro
                65                  70                  75

cag gtg ctg ggc ggc ccc tct gtg tct ctg gtt gct gga gtt cct gcg      290
Gln Val Leu Gly Gly Pro Ser Val Ser Leu Val Ala Gly Val Pro Ala
            80                  85                  90

aac ctg aca tgt cgg agc cgt ggg gat gcc cgc cct acc cct gaa ttg      338
Asn Leu Thr Cys Arg Ser Arg Gly Asp Ala Arg Pro Thr Pro Glu Leu
        95                  100                 105

ctg tgg ttc cga gat ggg gtc ctg ttg gat gga gcc acc ttc cat cag      386
Leu Trp Phe Arg Asp Gly Val Leu Leu Asp Gly Ala Thr Phe His Gln
    110                 115                 120

acc ctg ctg aag gaa ggg acc cct ggg tca gtg gag agc acc tta acc      434
Thr Leu Leu Lys Glu Gly Thr Pro Gly Ser Val Glu Ser Thr Leu Thr
125                 130                 135                 140

ctg acc cct ttc agc cat gat gat gga gcc acc ttt gtc tgc cgg gcc      482
Leu Thr Pro Phe Ser His Asp Asp Gly Ala Thr Phe Val Cys Arg Ala
                145                 150                 155

cgg agc cag gcc ctg ccc aca gga aga gac aca gct atc aca ctg agc      530
Arg Ser Gln Ala Leu Pro Thr Gly Arg Asp Thr Ala Ile Thr Leu Ser
            160                 165                 170

ctg cag tac ccc cca gag gtg act ctg tct gct tcg cca cac act gtg      578
Leu Gln Tyr Pro Pro Glu Val Thr Leu Ser Ala Ser Pro His Thr Val
        175                 180                 185

cag gag gga gag aag gtc att ttc ctg tgc cag gcc aca gcc cag cct      626
Gln Glu Gly Glu Lys Val Ile Phe Leu Cys Gln Ala Thr Ala Gln Pro
    190                 195                 200

cct gtc aca ggc tac agg tgg gca aaa ggg ggc tct ccg gtg ctc ggg      674
Pro Val Thr Gly Tyr Arg Trp Ala Lys Gly Gly Ser Pro Val Leu Gly
205                 210                 215                 220
```

-continued

```
gcc cgc ggg cca agg tta gag gtc gtg gca gac gcc tcg ttc ctg act      722
Ala Arg Gly Pro Arg Leu Glu Val Val Ala Asp Ala Ser Phe Leu Thr
                225                 230                 235

gag ccc gtg tcc tgc gag gtc agc aac gcc gtg ggt agc gcc aac cgc      770
Glu Pro Val Ser Cys Glu Val Ser Asn Ala Val Gly Ser Ala Asn Arg
            240                 245                 250

agt act gcg ctg gat gtg ctg ttt ggg ccg att ctg cag gca aag ccg      818
Ser Thr Ala Leu Asp Val Leu Phe Gly Pro Ile Leu Gln Ala Lys Pro
        255                 260                 265

gag ccc gtg tcc gtg gac gtg ggg gaa gac gct tcc ttc agc tgc gcc      866
Glu Pro Val Ser Val Asp Val Gly Glu Asp Ala Ser Phe Ser Cys Ala
    270                 275                 280

tgg cgc ggg aat ccg ctt cca cgg gta acc tgg acc cgc cgc ggt ggc      914
Trp Arg Gly Asn Pro Leu Pro Arg Val Thr Trp Thr Arg Arg Gly Gly
285                 290                 295                 300

gcg cag gtg ctg ggc tct gga gcc aca ctg cgt ctt ccg tcg gtg ggg      962
Ala Gln Val Leu Gly Ser Gly Ala Thr Leu Arg Leu Pro Ser Val Gly
                305                 310                 315

ccc gag gac gca gac gac tat gtg tgc aga gct gag gct ggg cta tcg     1010
Pro Glu Asp Ala Asp Asp Tyr Val Cys Arg Ala Glu Ala Gly Leu Ser
            320                 325                 330

ggt ctg cgg ggc ggc gcc gtg gag gct cgg ctg act gtg gac gct ccc     1058
Gly Leu Arg Gly Gly Ala Val Glu Ala Arg Leu Thr Val Asp Ala Pro
        335                 340                 345

cca gta gtg acc gcc ctg cac tct gcg cct gcc ttc ctg agg ggc cct     1106
Pro Val Val Thr Ala Leu His Ser Ala Pro Ala Phe Leu Arg Gly Pro
    350                 355                 360

gct cgc ctc cag tgt ctg gtt ttc gcc tct ccc gcc cca gat gcc gtg     1154
Ala Arg Leu Gln Cys Leu Val Phe Ala Ser Pro Ala Pro Asp Ala Val
365                 370                 375                 380

gtc tgg tct tgg gat gag ggc ttc ctg gag gcg ggg tcg cag ggt cgg     1202
Val Trp Ser Trp Asp Glu Gly Phe Leu Glu Ala Gly Ser Gln Gly Arg
                385                 390                 395

ttc ctg gtg gag aca ttc cct gcc cca gag agc cgc ggg gga ctg ggt     1250
Phe Leu Val Glu Thr Phe Pro Ala Pro Glu Ser Arg Gly Gly Leu Gly
            400                 405                 410

ccg ggc ctg atc tct gtg cta cac att tcg ggg acc cag gag tct gac     1298
Pro Gly Leu Ile Ser Val Leu His Ile Ser Gly Thr Gln Glu Ser Asp
        415                 420                 425

ttt agc agg agc ttt aac tgc agt gcc cgg aac cgg ctg ggc gag gga     1346
Phe Ser Arg Ser Phe Asn Cys Ser Ala Arg Asn Arg Leu Gly Glu Gly
    430                 435                 440

ggt gcc cag gcc agc ctg ggc cgt aga gac ttg ctg ccc act gtg cgg     1394
Gly Ala Gln Ala Ser Leu Gly Arg Arg Asp Leu Leu Pro Thr Val Arg
445                 450                 455                 460

ata gtg gcc gga gtg gtc gct gcc acc aca act ctc ctt atg gtc atc     1442
Ile Val Ala Gly Val Val Ala Ala Thr Thr Thr Leu Leu Met Val Ile
                465                 470                 475

act ggg gtg gcc ctc tgc tgc tgg cgc cac agc aag gcc tca gcc tct     1490
Thr Gly Val Ala Leu Cys Cys Trp Arg His Ser Lys Ala Ser Ala Ser
            480                 485                 490

ttc tcc gag caa aag aac ctg atg cga atc cct ggc agc agc gac ggc     1538
Phe Ser Glu Gln Lys Asn Leu Met Arg Ile Pro Gly Ser Ser Asp Gly
        495                 500                 505

tcc agt tca cga ggt cct gaa gaa gag gag aca ggc agc cgc gag gac     1586
Ser Ser Ser Arg Gly Pro Glu Glu Glu Glu Thr Gly Ser Arg Glu Asp
    510                 515                 520

cgg ggc ccc att gtg cac act gac cac agt gat ctg gtt ctg gag gag     1634
Arg Gly Pro Ile Val His Thr Asp His Ser Asp Leu Val Leu Glu Glu
525                 530                 535                 540
```

```
gaa ggg act ctg gag acc aag gac cca acc aac ggt tac tac aag gtc     1682
Glu Gly Thr Leu Glu Thr Lys Asp Pro Thr Asn Gly Tyr Tyr Lys Val
                545                 550                 555

cga gga gtc agt cca ccc gcg tct cca gac tca cgt gtg aca tct ttc     1730
Arg Gly Val Ser Pro Pro Ala Ser Pro Asp Ser Arg Val Thr Ser Phe
            560                 565                 570

caa tgg aag agt cct ggg atc tcc aac ttg cca taatggattg ttctgatttc   1783
Gln Trp Lys Ser Pro Gly Ile Ser Asn Leu Pro
        575                 580

tgaggagcca ggacaagttg gcgaccttac tcctcc                             1819


<210> SEQ ID NO 20
<211> LENGTH: 583
<212> TYPE: PRT
<213> ORGANISM: Homo sapiens

<400> SEQUENCE: 20

Met Leu Trp Met Arg Val Pro Ala Leu Leu Val Leu Leu Phe Cys Phe
1               5                   10                  15

Arg Gly Arg Ala Gly Trp Ser Arg Tyr Trp Ile Ser Gly Asn Ala Ala
            20                  25                  30

Asn Gly Gln His Asp Leu His Ile Arg Pro Val Glu Leu Glu Asp Glu
        35                  40                  45

Ala Ser Tyr Glu Cys Gln Ala Thr Gln Ala Gly Leu Arg Ser Arg Pro
    50                  55                  60

Ala Gln Leu His Val Leu Val Pro Pro Glu Ala Pro Gln Val Leu Gly
65                  70                  75                  80

Gly Pro Ser Val Ser Leu Val Ala Gly Val Pro Ala Asn Leu Thr Cys
                85                  90                  95

Arg Ser Arg Gly Asp Ala Arg Pro Thr Pro Glu Leu Leu Trp Phe Arg
            100                 105                 110

Asp Gly Val Leu Leu Asp Gly Ala Thr Phe His Gln Thr Leu Leu Lys
        115                 120                 125

Glu Gly Thr Pro Gly Ser Val Glu Ser Thr Leu Thr Leu Thr Pro Phe
    130                 135                 140

Ser His Asp Asp Gly Ala Thr Phe Val Cys Arg Ala Arg Ser Gln Ala
145                 150                 155                 160

Leu Pro Thr Gly Arg Asp Thr Ala Ile Thr Leu Ser Leu Gln Tyr Pro
                165                 170                 175

Pro Glu Val Thr Leu Ser Ala Ser Pro His Thr Val Gln Glu Gly Glu
            180                 185                 190

Lys Val Ile Phe Leu Cys Gln Ala Thr Ala Gln Pro Pro Val Thr Gly
        195                 200                 205

Tyr Arg Trp Ala Lys Gly Gly Ser Pro Val Leu Gly Ala Arg Gly Pro
    210                 215                 220

Arg Leu Glu Val Val Ala Asp Ala Ser Phe Leu Thr Glu Pro Val Ser
225                 230                 235                 240

Cys Glu Val Ser Asn Ala Val Gly Ser Ala Asn Arg Ser Thr Ala Leu
                245                 250                 255

Asp Val Leu Phe Gly Pro Ile Leu Gln Ala Lys Pro Glu Pro Val Ser
            260                 265                 270

Val Asp Val Gly Glu Asp Ala Ser Phe Ser Cys Ala Trp Arg Gly Asn
        275                 280                 285

Pro Leu Pro Arg Val Thr Trp Thr Arg Arg Gly Gly Ala Gln Val Leu
    290                 295                 300
```

```
Gly Ser Gly Ala Thr Leu Arg Leu Pro Ser Val Gly Pro Glu Asp Ala
305                 310                 315                 320

Asp Asp Tyr Val Cys Arg Ala Glu Ala Gly Leu Ser Gly Leu Arg Gly
                325                 330                 335

Gly Ala Val Glu Ala Arg Leu Thr Val Asp Ala Pro Pro Val Val Thr
            340                 345                 350

Ala Leu His Ser Ala Pro Ala Phe Leu Arg Gly Pro Ala Arg Leu Gln
        355                 360                 365

Cys Leu Val Phe Ala Ser Pro Ala Pro Asp Ala Val Val Trp Ser Trp
    370                 375                 380

Asp Glu Gly Phe Leu Glu Ala Gly Ser Gln Gly Arg Phe Leu Val Glu
385                 390                 395                 400

Thr Phe Pro Ala Pro Glu Ser Arg Gly Gly Leu Gly Pro Gly Leu Ile
                405                 410                 415

Ser Val Leu His Ile Ser Gly Thr Gln Glu Ser Asp Phe Ser Arg Ser
            420                 425                 430

Phe Asn Cys Ser Ala Arg Asn Arg Leu Gly Glu Gly Gly Ala Gln Ala
        435                 440                 445

Ser Leu Gly Arg Arg Asp Leu Leu Pro Thr Val Arg Ile Val Ala Gly
    450                 455                 460

Val Val Ala Ala Thr Thr Thr Leu Leu Met Val Ile Thr Gly Val Ala
465                 470                 475                 480

Leu Cys Cys Trp Arg His Ser Lys Ala Ser Ala Ser Phe Ser Glu Gln
                485                 490                 495

Lys Asn Leu Met Arg Ile Pro Gly Ser Ser Asp Gly Ser Ser Ser Arg
            500                 505                 510

Gly Pro Glu Glu Glu Glu Thr Gly Ser Arg Glu Asp Arg Gly Pro Ile
        515                 520                 525

Val His Thr Asp His Ser Asp Leu Val Leu Glu Glu Glu Gly Thr Leu
    530                 535                 540

Glu Thr Lys Asp Pro Thr Asn Gly Tyr Tyr Lys Val Arg Gly Val Ser
545                 550                 555                 560

Pro Pro Ala Ser Pro Asp Ser Arg Val Thr Ser Phe Gln Trp Lys Ser
                565                 570                 575

Pro Gly Ile Ser Asn Leu Pro
            580


<210> SEQ ID NO 21
<211> LENGTH: 2959
<212> TYPE: DNA
<213> ORGANISM: Homo sapiens
<220> FEATURE:
<221> NAME/KEY: CDS
<222> LOCATION: (196)..(2259)

<400> SEQUENCE: 21

atgcacttga gtgcaccttg agtctccagc ctctcaagga accgggagat caggccatca      60

gcgtctcagc cagcaaaggc ctgaaccacc agtcccttat aaccctgcgt ttcagagcgt     120

cagaggcgtg cttgagagga agaagttgac gggaaggcca gtgcgacggc aaatctcgtg     180

aaccttgggg gacga atg ctc agg atg cgg gtc ccc gcc ctc ctc gtc ctc      231
                 Met Leu Arg Met Arg Val Pro Ala Leu Leu Val Leu
                 1               5                   10

ctc ttc tgc ttc aga ggg aga gca ggc ccg tcg ccc cat ttc ctg caa      279
Leu Phe Cys Phe Arg Gly Arg Ala Gly Pro Ser Pro His Phe Leu Gln
        15                  20                  25
```

```
cag cca gag gac ctg gtg gtg ctg ctg ggg gag gaa gcc cgg ctg ccg      327
Gln Pro Glu Asp Leu Val Val Leu Leu Gly Glu Glu Ala Arg Leu Pro
    30                  35                  40

tgt gct ctg ggc gcc tac tgg ggg cta gtt cag tgg act aag agt ggg      375
Cys Ala Leu Gly Ala Tyr Trp Gly Leu Val Gln Trp Thr Lys Ser Gly
45                  50                  55                  60

ctg gcc cta ggg ggc caa agg gac cta cca ggg tgg tcc cgg tac tgg      423
Leu Ala Leu Gly Gly Gln Arg Asp Leu Pro Gly Trp Ser Arg Tyr Trp
                65                  70                  75

ata tca ggg aat gca gcc aat ggc cag cat gac ctc cac att agg ccc      471
Ile Ser Gly Asn Ala Ala Asn Gly Gln His Asp Leu His Ile Arg Pro
            80                  85                  90

gtg gag cta gag gat gaa gca tca tat gaa tgt cag gct aca caa gca      519
Val Glu Leu Glu Asp Glu Ala Ser Tyr Glu Cys Gln Ala Thr Gln Ala
        95                  100                 105

ggc ctc cgc tcc aga cca gcc caa ctg cac gtg ctg gtc ccc cca gaa      567
Gly Leu Arg Ser Arg Pro Ala Gln Leu His Val Leu Val Pro Pro Glu
    110                 115                 120

gcc ccc cag gtg ctg ggc ggc ccc tct gtg tct ctg gtt gct gga gtt      615
Ala Pro Gln Val Leu Gly Gly Pro Ser Val Ser Leu Val Ala Gly Val
125                 130                 135                 140

cct gcg aac ctg aca tgt cgg agc cgt ggg gat gcc cgc cct acc cct      663
Pro Ala Asn Leu Thr Cys Arg Ser Arg Gly Asp Ala Arg Pro Thr Pro
                145                 150                 155

gaa ttg ctg tgg ttc cga gat ggg gtc ctg ttg gat gga gcc acc ttc      711
Glu Leu Leu Trp Phe Arg Asp Gly Val Leu Leu Asp Gly Ala Thr Phe
            160                 165                 170

cat cag acc ctg ctg aag gaa ggg acc cct ggg tca gtg gag agc acc      759
His Gln Thr Leu Leu Lys Glu Gly Thr Pro Gly Ser Val Glu Ser Thr
        175                 180                 185

tta acc ctg ccc aca gga aga gac aca gct atc aca ctg agc ctg cag      807
Leu Thr Leu Pro Thr Gly Arg Asp Thr Ala Ile Thr Leu Ser Leu Gln
    190                 195                 200

tac ccc cca gag gtg act ctg tct gct tcg cca cac act gtg cag gag      855
Tyr Pro Pro Glu Val Thr Leu Ser Ala Ser Pro His Thr Val Gln Glu
205                 210                 215                 220

gga gag aag gtc att ttc ctg tgc cag gcc aca gcc cag cct cct gtc      903
Gly Glu Lys Val Ile Phe Leu Cys Gln Ala Thr Ala Gln Pro Pro Val
                225                 230                 235

aca ggc tac agg tgg gca aaa ggg ggc tct ccg gtg ctc ggg gcc cgc      951
Thr Gly Tyr Arg Trp Ala Lys Gly Gly Ser Pro Val Leu Gly Ala Arg
            240                 245                 250

ggg cca agg tta gag gtc gtg gca gac gcc tcg ttc ctg act gag ccc      999
Gly Pro Arg Leu Glu Val Val Ala Asp Ala Ser Phe Leu Thr Glu Pro
        255                 260                 265

gtg tcc tgc gag gtc agc aac gcc gtg ggt agc gcc aac cgc agt act     1047
Val Ser Cys Glu Val Ser Asn Ala Val Gly Ser Ala Asn Arg Ser Thr
    270                 275                 280

gcg ctg gat gtg ctg ttt ggg ccg att ctg cag gca aag ccg gag ccc     1095
Ala Leu Asp Val Leu Phe Gly Pro Ile Leu Gln Ala Lys Pro Glu Pro
285                 290                 295                 300

gtg tcc gtg gac gtg ggg gaa gac gct tcc ttc agc tgc gcc tgg cgc     1143
Val Ser Val Asp Val Gly Glu Asp Ala Ser Phe Ser Cys Ala Trp Arg
                305                 310                 315

ggg aac ccg ctt cca cgg gta acc tgg acc cgc cgc ggt ggc gcg cag     1191
Gly Asn Pro Leu Pro Arg Val Thr Trp Thr Arg Arg Gly Gly Ala Gln
            320                 325                 330

gtg ctg ggc tct gga gcc aca ctg cgt ctt ccg tcg gtg ggg ccc gag     1239
Val Leu Gly Ser Gly Ala Thr Leu Arg Leu Pro Ser Val Gly Pro Glu
```

```
        335                 340                 345

gac gca ggc gac tat gtg tgc aga gct gag gct ggg cta tcg ggc ctg     1287
Asp Ala Gly Asp Tyr Val Cys Arg Ala Glu Ala Gly Leu Ser Gly Leu
    350                 355                 360

cgg ggc ggc gcc gcg gag gct cgg ctg act gtg aac gct ccc cca gta     1335
Arg Gly Gly Ala Ala Glu Ala Arg Leu Thr Val Asn Ala Pro Pro Val
365                 370                 375                 380

gtg acc gcc ctg cac tct gcg cct gcc ttc ctg agg ggc cct gct cgc     1383
Val Thr Ala Leu His Ser Ala Pro Ala Phe Leu Arg Gly Pro Ala Arg
                385                 390                 395

ctc cag tgt ctg gtt ttc gcc tct ccc gcc cca gat gcc gtg gtc tgg     1431
Leu Gln Cys Leu Val Phe Ala Ser Pro Ala Pro Asp Ala Val Val Trp
            400                 405                 410

tct tgg gat gag ggc ttc ctg gag gcg ggg tcg cag ggc cgg ttc ctg     1479
Ser Trp Asp Glu Gly Phe Leu Glu Ala Gly Ser Gln Gly Arg Phe Leu
        415                 420                 425

gtg gag aca ttc cct gcc cca gag agc cgc ggg gga ctg ggt ccg ggc     1527
Val Glu Thr Phe Pro Ala Pro Glu Ser Arg Gly Gly Leu Gly Pro Gly
    430                 435                 440

ctg atc tct gtg cta cac att tcg ggg acc cag gag tct gac ttt agc     1575
Leu Ile Ser Val Leu His Ile Ser Gly Thr Gln Glu Ser Asp Phe Ser
445                 450                 455                 460

agg agc ttt aac tgc agt gcc cgg aac cgg ctg ggc gag gga ggt gcc     1623
Arg Ser Phe Asn Cys Ser Ala Arg Asn Arg Leu Gly Glu Gly Gly Ala
                465                 470                 475

cag gcc agc ctg ggc cgt aga gac ttg ctg ccc act gtg cgg ata gtg     1671
Gln Ala Ser Leu Gly Arg Arg Asp Leu Leu Pro Thr Val Arg Ile Val
            480                 485                 490

gcc gga gtg gcc gct gcc acc aca act ctc ctt atg gtc atc act ggg     1719
Ala Gly Val Ala Ala Ala Thr Thr Thr Leu Leu Met Val Ile Thr Gly
        495                 500                 505

gtg gcc ctc tgc tgc tgg cgc cac agc aag gcc tca gcc tct ttc tcc     1767
Val Ala Leu Cys Cys Trp Arg His Ser Lys Ala Ser Ala Ser Phe Ser
    510                 515                 520

gag caa aag aac ctg atg cga atc cct ggc agc agc gac ggc tcc agt     1815
Glu Gln Lys Asn Leu Met Arg Ile Pro Gly Ser Ser Asp Gly Ser Ser
525                 530                 535                 540

tca cga ggt cct gaa gaa gag gag aca ggc agc cgc gag gac cgg ggc     1863
Ser Arg Gly Pro Glu Glu Glu Glu Thr Gly Ser Arg Glu Asp Arg Gly
                545                 550                 555

ccc att gtg cac act gac cac agt gat ctg gtt ctg gag gag gaa ggg     1911
Pro Ile Val His Thr Asp His Ser Asp Leu Val Leu Glu Glu Glu Gly
            560                 565                 570

act ctg gag acc aag gac cca acc aac ggt tac tac aag gtc cga gga     1959
Thr Leu Glu Thr Lys Asp Pro Thr Asn Gly Tyr Tyr Lys Val Arg Gly
        575                 580                 585

gtc agt gtg agc ctg agc ctt ggc gaa gcc cct gga gga ggt ctc ttc     2007
Val Ser Val Ser Leu Ser Leu Gly Glu Ala Pro Gly Gly Gly Leu Phe
    590                 595                 600

ctg cca cca ccc tcc ccc ctt ggg ccc cca ggg acc cct acc ttc tat     2055
Leu Pro Pro Pro Ser Pro Leu Gly Pro Pro Gly Thr Pro Thr Phe Tyr
605                 610                 615                 620

gac ttc aac cca cac ctg ggc atg gtc ccc ccc tgc aga ctt tac aga     2103
Asp Phe Asn Pro His Leu Gly Met Val Pro Pro Cys Arg Leu Tyr Arg
                625                 630                 635

gcc agg gca ggc tat ctc acc aca ccc cac cct cga gct ttc acc agc     2151
Ala Arg Ala Gly Tyr Leu Thr Thr Pro His Pro Arg Ala Phe Thr Ser
            640                 645                 650

tac atc aaa ccc aca tcc ttt ggg ccc cca gat ctg gcc ccc ggg act     2199
```

```
Tyr Ile Lys Pro Thr Ser Phe Gly Pro Pro Asp Leu Ala Pro Gly Thr
        655                 660                 665

ccc ccc ttc cca tat gct gcc ttc ccc aca cct agc cac ccg cgt ctc      2247
Pro Pro Phe Pro Tyr Ala Ala Phe Pro Thr Pro Ser His Pro Arg Leu
    670                 675                 680

cag act cac gtg tgacatcttt ccaatggaag agtcctggga tctccaactt          2299
Gln Thr His Val
685

gccataatgg attgttctga tttctgagga gccaggacaa gttggcgacc ttactcctcc   2359

aaaactgaac acaaggggag ggaaagatca ttacatttgt caggagcatt tgtatacagt   2419

cagctcagcc aaaggagatg ccccaagtgg gagcaacatg gccacccaat atgcccacct   2479

attccccggt gtaaaagaga ttcaagatgg caggtaggcc ctttgaggag agatggggac   2539

agggcagtgg gtgttgggag tttggggccg ggatggaagt tgtttctagc cactgaaaga   2599

agatatttca agatgaccat ctgcattgag aggaaaggta gcataggata gatgaagatg   2659

aagagcatac caggccccac cctggctctc cctgagggga actttgctcg gccaatggaa   2719

atgcagccaa gatggccata tactccctag gaacccaaga tggccaccat cttgatttta   2779

ctttccttaa agactcagaa agacttggac ccaaggagtg ggatacagt gagaattacc    2839

actgttgggg caaaatattg ggataaaaat atttatgttt aataataaaa aaaagtcaaa   2899

gaggaaaaaa aaaaaaaaaa aaaaaaaaaa aaaaaaaaaa aaaaaaaaaa aaaaaaaaaa   2959


<210> SEQ ID NO 22
<211> LENGTH: 688
<212> TYPE: PRT
<213> ORGANISM: Homo sapiens

<400> SEQUENCE: 22

Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Pro
            180                 185                 190

Thr Gly Arg Asp Thr Ala Ile Thr Leu Ser Leu Gln Tyr Pro Pro Glu
        195                 200                 205
```

```
Val Thr Leu Ser Ala Ser Pro His Thr Val Gln Glu Gly Glu Lys Val
    210                 215                 220

Ile Phe Leu Cys Gln Ala Thr Ala Gln Pro Pro Val Thr Gly Tyr Arg
225                 230                 235                 240

Trp Ala Lys Gly Gly Ser Pro Val Leu Gly Ala Arg Gly Pro Arg Leu
                245                 250                 255

Glu Val Val Ala Asp Ala Ser Phe Leu Thr Glu Pro Val Ser Cys Glu
            260                 265                 270

Val Ser Asn Ala Val Gly Ser Ala Asn Arg Ser Thr Ala Leu Asp Val
        275                 280                 285

Leu Phe Gly Pro Ile Leu Gln Ala Lys Pro Glu Pro Val Ser Val Asp
    290                 295                 300

Val Gly Glu Asp Ala Ser Phe Ser Cys Ala Trp Arg Gly Asn Pro Leu
305                 310                 315                 320

Pro Arg Val Thr Trp Thr Arg Arg Gly Gly Ala Gln Val Leu Gly Ser
                325                 330                 335

Gly Ala Thr Leu Arg Leu Pro Ser Val Gly Pro Glu Asp Ala Gly Asp
            340                 345                 350

Tyr Val Cys Arg Ala Glu Ala Gly Leu Ser Gly Leu Arg Gly Gly Ala
        355                 360                 365

Ala Glu Ala Arg Leu Thr Val Asn Ala Pro Pro Val Val Thr Ala Leu
    370                 375                 380

His Ser Ala Pro Ala Phe Leu Arg Gly Pro Ala Arg Leu Gln Cys Leu
385                 390                 395                 400

Val Phe Ala Ser Pro Ala Pro Asp Ala Val Val Trp Ser Trp Asp Glu
                405                 410                 415

Gly Phe Leu Glu Ala Gly Ser Gln Gly Arg Phe Leu Val Glu Thr Phe
            420                 425                 430

Pro Ala Pro Glu Ser Arg Gly Gly Leu Gly Pro Gly Leu Ile Ser Val
        435                 440                 445

Leu His Ile Ser Gly Thr Gln Glu Ser Asp Phe Ser Arg Ser Phe Asn
    450                 455                 460

Cys Ser Ala Arg Asn Arg Leu Gly Glu Gly Gly Ala Gln Ala Ser Leu
465                 470                 475                 480

Gly Arg Arg Asp Leu Leu Pro Thr Val Arg Ile Val Ala Gly Val Ala
                485                 490                 495

Ala Ala Thr Thr Thr Leu Leu Met Val Ile Thr Gly Val Ala Leu Cys
            500                 505                 510

Cys Trp Arg His Ser Lys Ala Ser Ala Ser Phe Ser Glu Gln Lys Asn
        515                 520                 525

Leu Met Arg Ile Pro Gly Ser Ser Asp Gly Ser Ser Ser Arg Gly Pro
    530                 535                 540

Glu Glu Glu Glu Thr Gly Ser Arg Glu Asp Arg Gly Pro Ile Val His
545                 550                 555                 560

Thr Asp His Ser Asp Leu Val Leu Glu Glu Glu Gly Thr Leu Glu Thr
                565                 570                 575

Lys Asp Pro Thr Asn Gly Tyr Tyr Lys Val Arg Gly Val Ser Val Ser
            580                 585                 590

Leu Ser Leu Gly Glu Ala Pro Gly Gly Gly Leu Phe Leu Pro Pro Pro
        595                 600                 605

Ser Pro Leu Gly Pro Pro Gly Thr Pro Thr Phe Tyr Asp Phe Asn Pro
    610                 615                 620
```

His Leu Gly Met Val Pro Pro Cys Arg Leu Tyr Arg Ala Arg Ala Gly
625 630 635 640

Tyr Leu Thr Thr Pro His Pro Arg Ala Phe Thr Ser Tyr Ile Lys Pro
645 650 655

Thr Ser Phe Gly Pro Pro Asp Leu Ala Pro Gly Thr Pro Pro Phe Pro
660 665 670

Tyr Ala Ala Phe Pro Thr Pro Ser His Pro Arg Leu Gln Thr His Val
675 680 685

<210> SEQ ID NO 23
<211> LENGTH: 291
<212> TYPE: DNA
<213> ORGANISM: Artificial
<220> FEATURE:
<223> OTHER INFORMATION: an artificially synthesized sequence

<400> SEQUENCE: 23
aagctttcta gagggcccgt ttaaacccgc tgatcagcct cgactgtgcc ttctagttgc 60
cagccatctg ttgtttgccc ctcccccgtg ccttccttga ccctggaagg tgccactccc 120
actgtccttt cctaataaaa tgaggaaatt gcatcgcatt gtctgagtag gtgtcattct 180
attctggggg gtggggtggg gcaggacagc aagggggagg attgggaaga caatagcagg 240
catgctgggg atgcggtggg ctctatggct tctgaggcgg aaagactcga g 291

<210> SEQ ID NO 24
<211> LENGTH: 32
<212> TYPE: DNA
<213> ORGANISM: Artificial
<220> FEATURE:
<223> OTHER INFORMATION: an artificially synthesized sequence

<400> SEQUENCE: 24
gtaccactag tgctagcacg cgtgcggccg cg 32

<210> SEQ ID NO 25
<211> LENGTH: 32
<212> TYPE: DNA
<213> ORGANISM: Artificial
<220> FEATURE:
<223> OTHER INFORMATION: an artificially synthesized sequence

<400> SEQUENCE: 25
gatccgcggc cgcacgcgtg ctagcactag tg 32

<210> SEQ ID NO 26
<211> LENGTH: 3261
<212> TYPE: DNA
<213> ORGANISM: Artificial
<220> FEATURE:
<223> OTHER INFORMATION: an artificially synthesized sequence

<400> SEQUENCE: 26
atcgattagg agcctatggt ggcacttgtg agcaccagca gcttgtttgt tgctgtcttc 60
cctgagcctc tctctgtgtg ccctgctttt ctgttctttc aatctctttc taactcgccc 120
ttctctcttc cctccctccc tccctccctt ccttctttct cttatcttcc taccattgtc 180
tgtgactgtc gcagtctttc tgtcccggca tcgccttttc tgcccttttc tccccctttc 240
tcccccgtta acagttcttt ctctgagctc taaccccaag accttaaaaa tgccccccttc 300 tctctgtttt tctttactat cacctccctc tcacccactc acaggtactc aaagagcacc 360
ggctgctcta agtccagcag gttcacgaac ccaaagcagt cagccacagc actgagcatt 420

```
gcttggaccc agtgtgaact cattctgctg cttcccccaa gtccttcctg agtctgccca    480
gccgggcaat gaaatcccct gtcagcacat gccaggaaca ttctttggtg cctccccagc    540
ccgggtgacc ccaaggcccc gggagagcat ttctgatcag ggccatctcc agctcaggat    600
ggaacgcaga gctaggcctg tgtgcgtggg aaggctacaa cccccccccc aggacatcct    660
tgctctttgc agcccagact gtggcatgta ccgcacccct gctggtgaat atgcaggagt    720
gtgttgttaa accaagagag tatgggacag agagaagcca cttctgtggg tatgggtttc    780
agagtgtgcg tgttccaggg gagacgagag cagattttca tctgtggacg tatttggagt    840
gtctcatatg ggtgtgcaca gagcatccag acagtcagca ggactgtgtc cgcagacctc    900
agtgtgtgga aacctggtgt gctcagacgc agataaacat agggtggggg gtccctggga    960
gctgaagcac ctgaatccct gggccatgtg agggccttct gtttcctcaa ctcctccatc   1020
ttcccttgtg tgtgtgtgtg tgtgtgtgtg tatgtcttgc taggatgatt tatcttctta   1080
ttcttctcca cgtctttaat tccatctccc ccctcctcct cctcctccat tcctacccc    1140
ttctcatttt ctgtcactct tgctgccccc tctgtgtctg gtccttgaat tttagaagca   1200
tatgttgact ggcctgccct cccaacctgg gtgcacagat gaattcgcct gggataagcc   1260
cctgctgcct gcttatctcc tgcaggaatt gcaactgttc tcttttgccc catattccct   1320
acaaacctct cacctcccgg ctgcttcttc tccaggaggc agtccaggca tctggcctga   1380
gccccccctca cagctctcta ccaagggtga gccctctggt ctttctttcc cacccagccc   1440
cattattgat tcattaccct tggtccacat tcccatctcc aaacctatca acacctcctg   1500
ggcaatggat tgcatacaga ccaagccagg gagtctgcta tggggccttt gccagatggt   1560
atctttgggg gccaaggtgt agagctgtca gttgctggag cctttaatta gtgcaaacct   1620
tctacactca cctttggctg ttttccttct ctgaatgctc tggggatccc aggctctcca   1680
tttttccatc ccgtggcccc agagtgccag gaaagggaag ctgtgtcagg tgtctggaaa   1740
aacagcctct cacctgactt cctcccgggg acttaggagt cctgggctca agtctgtcct   1800
atttcaaaac tcagaagcca ggagttcaga tttaggtgtg aggcctccta ggactctctt   1860
ttccaggccc ccagcctgca atccctccac ttctacagga ctcagcacag ctgttcagtc   1920
tgttggtttt cccatcctcg ggggccctag ggggtgagtg agaacgagac tggatgtcaa   1980
atccagtagc tttaagactt aagaccagac attctgaaac tggctcaact ccaccacact   2040
gcagcctgca aggcttctca gccagcagag aagtctgaac tatccccctg gggcaagtcc   2100
aaccctctga tatttagaag taccagtctg agccccaaat gtcatttatt tctgagaggt   2160
ccaggaatgt cagacccggg gtctcaggcc cccaacctcc ccccctccag cccccttcagt   2220
gagctcaggg tccctcccac ctgctctgcc agctgcactg cgtgggaacg cccagctggg   2280
ctgcaccgga gctgtcagga caagctgtgc ggttcccagc ctccctccct gcctgccaga   2340
gccagggcac tgctgcctcc cagccgtcgc ccggcaacca ctcaccactc ggatgggcca   2400
gggactgctg ggtggagaga ggggacgggt gggtgggtac tgctgggtcc tgggaaagga   2460
ggaactcctg gaggggaggg ggcgggctag attcctagat cttaaggtac gtgtatggct   2520
tgcagggata acagagcagc agggagtatt ttgggaaata gggagtattt gggaaatagg   2580
gagcagaaac cctcttctct caaggctcct aaatggtcct tcagcacctg ggtgccctct   2640
ctccgacccg caggcccacg ggagcctgag ctccgcctcc ccagggcgcg gaagctggcg   2700
aagccccagg gattcccatt tatagcttgg tttccactca gctcagtccc tccaggactc   2760
```

```
gggctgagca agtttcttcc attcccttct ctcctccctc cacccccttc tcctcctcct   2820

tctccttctt ttcttcctcc tcattcccgc ctccccttca acctcagcag ggtgcaggtg   2880

tccaactcga acaagggccc caacttggac tcagatgttc ccactctcag accccctgat   2940

aatgccgtcc gcacacaagg cgcgggagtt tctcaatggg aagaggccgg gactctagga   3000

ggcggggcga ataggattcc tcccgcctag tgggtccctc gcagtcctag ggttgcaacc   3060

cttgagcggt agagaacacc ggagactgcg gatgagccag atttcgggga cataaaatct   3120

tccagcccgg agagaattgt gtgcagagag ggctccagt ccagcgtggt gtgagaggcg    3180

tgctatcaag aaagaagttg gaggggaacc agtgcaaccc taactctgcg agatcttggg   3240

gtacacacac tcgggggtac c                                              3261
```

<210> SEQ ID NO 27
<211> LENGTH: 740
<212> TYPE: DNA
<213> ORGANISM: Artificial
<220> FEATURE:
<223> OTHER INFORMATION: an artificially synthesized sequence

<400> SEQUENCE: 27

```
ggtaccgcca ccatggtgag caagggcgag gagctgttca ccggggtggt gcccatcctg     60

gtcgagctgg acggcgacgt aaacggccac aagttcagcg tgtccggcga gggcgagggc    120

gatgccacct acggcaagct gaccctgaag ttcatctgca ccaccggcaa gctgcccgtg    180

ccctggccca ccctcgtgac caccctgacc tacggcgtgc agtgcttcag ccgctacccc    240

gaccacatga agcagcacga cttcttcaag tccgccatgc ccgaaggcta cgtccaggag    300

cgcaccatct tcttcaagga cgacggcaac tacaagaccc gcgccgaggt gaagttcgag    360

ggcgacaccc tggtgaaccg catcgagctg aagggcatcg acttcaagga ggacggcaac    420

atcctggggc acaagctgga gtacaactac aacagccaca acgtctatat catggccgac    480

aagcagaaga acggcatcaa ggtgaacttc aagatccgcc acaacatcga ggacggcagc    540

gtgcagctcg ccgaccacta ccagcagaac acccccatcg gcgacggccc cgtgctgctg    600

cccgacaacc actacctgag cacccagtcc gccctgagca aagaccccaa cgagaagcgc    660

gatcacatgg tcctgctgga gttcgtgacc gccgccggga tcactctcgg catggacgag    720

ctgtacaagt aagcggccgc                                                740
```

<210> SEQ ID NO 28
<211> LENGTH: 2064
<212> TYPE: DNA
<213> ORGANISM: Artificial
<220> FEATURE:
<223> OTHER INFORMATION: an artificially synthesized sequence

<400> SEQUENCE: 28

```
atcgatgaac aagatgaggc atctggcctc agcccccagc ttcaccctcg atgctggact     60

tccatcttcc ctcacatgct tgactccttg ccctcctccc acctcccctc tcccaactgc    120

tctctacacc ccctgggaaa tgggctggat gccgagctgg gggagtggct ctgtcctggg    180

ggccctcgcc agatggtgtc cctaggtgcc agagcgtgga gctgtccctt gctggggcct    240

ttaataagca caaaccttcc accctccacc ttgattgttt tccttctctg catgctcctg    300

ggaccttggg ctctccatct ttccatgtcc gtagccccag agagccagga aggggaagcg    360

gcgtcaagtg cctggaaaaa cagccccatg acttgagttc ctccctaaga ctcaggagtt    420

ccagccccat gtccatccta tttcaaaatc caggcactag ataagccaca cagaagccgg    480
```

```
gagtgtaggc ccccagatcc ctcccctctc agaccctggg gtctcagtcc cttctctcca    540
aggactcggg aatttgggcc tctgatcctc ctggccacac tacccacccc cgcacctccc    600
catacacaca cacacacaca cacacacaca cacacacaca cacatataca cacaggactt    660
aggacagatg ttcacggtct gatttccaaa tcctcctggg cctgtgtggg ggtggggaga    720
gattggcaga tagatccacc gactcttaag acttaagacc agatattctg acccctgtca    780
ccctcttcca agtgcaccat gcacttgagt gcaccttgag tctccagcct ctcaaggaac    840
cgggagatca ggccatcagc gtctcagcca gcaaaggcct gaaccaccag tcccttataa    900
ccctgtaagt ccaaccccca ctcccaaccc cactccccca tttagggaca cggagtctga    960
gcctaagaac agtggagaat ctgaatgtgg accctccagt tcttacaggt ccaggaatgt   1020
cagatcaggg tcccagcccc ccagccctcc ttcaggctgc tcggggtccc tcccacctgc   1080
tcggccagct gcgcagcgtg ggaacgcccc agctgggctg catggagccg tcaggacaag   1140
ctgcgcggtt cccagcctcc ctgcctgccc cggcccggca ccgccgcctc ccagccgtcg   1200
ccgggcaacc aggccgaggg gcccggccgg ccgagtgggg agaggggttg ggctgggact   1260
gcggggtcct gggaaaggag gggccgaggg cctggattcc tgggtcttag gacgtgctgt   1320
agtttgcagc aataacaagg gaacagaggg atattttgag gaggggtttt gaggctgggg   1380
gagtcgaggt aggggtccca actgtccccc aggtatcggc gtgccctctt cccgacgcgc   1440
aggcccgggg gagccccgga ccccgcatcc cccagggcgc ggaaactggc gaggccccag   1500
gagctcccat ttatagctca gtttccactg agcgcagtcc ctctaggacc tgggctgagc   1560
aagtttcttc cactctctcc cttccctcct cctcacccct tgcctgcccc tcaaccccgg   1620
cagggcgcag gtgtccaacc cagccgggac cccctccctc ctcgaaccca ggtgttccgg   1680
ctcccagacc ccaattgagc tgggggcgcc cacccgccgg gggatcccgc cctgcgtccc   1740
ccattcatcc gcgtctcagc cgcgggagtt tctcaacggg aagagggcgg agctcccggg   1800
gggcggaccc gggcggggcg agcgggatcg ggccctcttg ggtctcccca gagacccagg   1860
ccgcggaact ggcaggcgtt tcagagcgtc agaggctgcg gatgagcaga cttggaggac   1920
tccaggccag agactaggct gggcgaagag tcgagcgtga agggggctcc gggccagggt   1980
gacaggaggc gtgcttgaga ggaagaagtt gacgggaagg ccagtgcgac ggcaaatctc   2040
gtgaaccttg ggggacgagg tacc                                          2064
```

METHOD FOR OBTAINING PANCREATIC PROGENITOR CELL USING NEPH3

CROSS-REFERENCE TO RELATED APPLICATIONS

The present application is a U.S. National Phase of PCT/JP 2009/071089, filed Dec. 18, 2009, which claims the benefit of Japanese Application No. 2008 -326401, filed on Dec. 22, 2008, and Japanese Application No. 2009 -040667, filed on Feb. 24, 2009, the disclosures of which are hereby incorporated herein by reference in their entirety.

TECHNICAL FIELD

The present invention relates to the use and such of the gene for distinguishing, detecting, identifying, isolating, obtaining, and the like of pancreatic progenitor cells.

BACKGROUND ART

Pancreas is an important organ that secretes various digestive enzymes to digest food as well as various hormones to control blood glucose concentration. It is known that functional breakdown of the pancreas due to autoimmune disease, cancer, obesity, or such results in pathological elevation of blood glucose concentration, causing various complications. Diabetes is developed due to deficiency in quantity or deterioration in the function of insulin secreted from β cells present in the pancreas. The therapeutic methods include exercise therapy, diet therapy, oral hypoglycemic agents, and insulin injection. Meanwhile, cell transplantation therapy is performed, in which pancreatic β cells harvested from brain-dead patients are transplanted into diabetes patients. However, the extreme scarcity of donors is problematic in cell transplantation therapy. Recently, transplantation technology has been developed to differentiate pancreatic multipotent progenitor cells to be transplanted from human embryonic stem (ES) cells, and it has drawn attention as a method that solves the donor problem (Kroon E et al., Nat. Biotechnol. (2008) 26(4): 443-52). However, when human ES cell-derived pancreatic progenitor cells are transplanted, only a fraction of the cells differentiated from ES cells differentiate into pancreatic progenitor cells and the remaining cells differentiate into completely different cell populations. Hence, in consideration of safety and efficacy, it is believed to be very important to remove undifferentiated ES cells and to enrich pancreatic multipotent progenitor cells through sorting using specific antibodies. Additionally, conventional technologies cannot distinguish, detect, identify, isolate, and/or obtain pancreatic progenitor cells in a viable state that does not contain foreign genes, proteins, and such; and thus it is desirable to distinguish, detect, identify, isolate, and/or obtain pancreatic progenitor cells in a viable state that do not contain foreign genes, proteins, and such.

By the way, it has been known that the Nephrin-like 3 (Neph3) gene is expressed in central nervous system progenitor cells after division arrest, such as dopamine-producing neuron progenitor cells and GABA-producing inhibitory neuron progenitor cells (WO 2004/038018; WO 2008/096817). However, it is unknown that the gene is relevant to pancreatic multipotent progenitor cells.

PRIOR-ART DOCUMENTS

Patent Documents

[Patent Document 1] WO 2004/038018
[Patent Document 2] WO 2008/096817

Non-Patent Documents

[Non-patent Document 1] Kroon E et al., Nat. Biotechnol. (2008) 26(4): 443-52

DISCLOSURE OF THE INVENTION

Problems to be Solved by the Invention

The present invention was achieved in view of the above circumstances. An objective of the present invention is to provide methods for distinguishing, detecting, identifying, isolating, and/or obtaining pancreatic progenitor cells, which use as an indicator a marker that can selectively distinguish pancreatic progenitor cells, cell populations and the like prepared by the methods.

Means for Solving the Problems

The Nephrin-like 3 (Neph3) gene encodes a membrane protein having immunoglobulin-like domains in its extracellular region. The Neph3 gene is also known as "65B13" gene, and has been reported to be transiently expressed in central nervous system progenitor cells after division arrest, such as dopamine-producing neuron progenitor cells and GABA neuron progenitor cells (WO 2004/038018; WO 2008/096817). However, there has been no report on the relevance of the gene to pancreatic progenitor cells. The present inventors analyzed in detail the Neph3 gene expression during pancreatic development, and as a result revealed that Neph3 was expressed in a fraction of pancreatic primordial cells, and the expression pattern was highly similar to those of pancreatic duodenal homeobox factor-1 (Pdx-1) and pancreas transcription factor 1 subunit alpha (Ptf1a) known as indicators of multipotent pancreatic progenitor cells (or pancreatic multipotent progenitor cells). Further analysis was carried out to characterize Neph3-positive cells in the pancreatic primordium. The result showed that most of the Neph3-positive cells were positive for both Pdx-1 and Ptf1a. In addition, most of the Neph3-positive cells also expressed carboxypeptidase A1 (pancreatic) (Cpa1), which is another indicator for multipotent pancreatic progenitor cells (Zhou Q. et al., Dev. Cell, (2007) 13 (1): 103-114).

As described above, Neph3 is expressed in multipotent pancreatic progenitor cells, in particular, on the cell surface, and is useful as a surface marker for multipotent pancreatic progenitor cells. Thus, viable multipotent pancreatic progenitor cells can be simply distinguished, detected, identified, isolated, and/or obtained by using Neph3 as an indicator. The Neph3 gene and protein can be used to distinguish, detect, identify, isolate and/or obtain multipotent pancreatic progenitor cells from cell populations potentially containing multipotent pancreatic progenitor cells.

Specifically, the present invention relates to markers that enable selective detection of pancreatic progenitor cells, methods that use the markers as an indicator to distinguish, detect, identify, isolate, and/or obtain pancreatic progenitor cells, as well as cell populations distinguished, detected, identified, isolated, and/or obtained by the methods, and reagents and the like for use in the methods. More specifically, the present invention provides:

[1] a method for producing a cell population comprising a pancreatic progenitor cell, which comprises the step of distinguishing, detecting, and/or identifying the expression of a translated product of a Nephrin-like 3 (Neph3) gene in an endodermal cell sample, and the step of collecting, isolating, and/or obtaining a cell expressing the translated product of the gene;
[2] the method of [1], wherein the endodermal cell sample is a central nervous system lineage cell-depleted cell sample;
[3] the method of [1], wherein the endodermal cell sample is an abdomen-derived cell sample;
[4] the method of any one of [1] to [3], which additionally comprises the step of distinguishing, detecting, identifying, collecting, isolating, and/or obtaining the expression of a translated product and/or transcript of any one or a combination of pancreatic and duodenal homeobox factor-1 (Pdx-1), pancreas specific transcription factor-1a (Ptf1a), carboxypeptidase A1 (pancreatic) (Cpa1), and epiplakin 1 (EPPK1) genes;
[5] the method of [4], wherein the combination consists of pancreatic and duodenal homeobox factor-1 (Pdx-1) and carboxypeptidase A1 (pancreatic) (Cpa1);
[6] the method of any one of [1] to [5], wherein the step of distinguishing, detecting, and/or identifying, and/or the step of collecting, isolating, and/or obtaining are achieved by using an immunochemical method;
[7] a cell population prepared by the method of any one of [1] to [6].
[8] a method for distinguishing, detecting, identifying, collecting, isolating, and/or obtaining a pancreatic progenitor cell, which comprises the step of distinguishing, detecting, and/or identifying the expression of a translated product of a Neph3 gene in an endodermal cell sample.
[9] the method of [8], wherein the endodermal cell sample is a central nervous system lineage cell-depleted cell sample;
[10] the method of [8], wherein the endodermal cell sample is an abdomen-derived cell sample;
[11] the method of any one of [8] to [10], which additionally comprises the step of distinguishing, detecting, identifying, collecting, isolating, and/or obtaining the expression of a translated product and/or transcript of any one or a combination of pancreatic and duodenal homeobox factor-1 (Pdx-1), pancreas specific transcription factor-1a (Ptf1a), carboxypeptidase A1 (pancreatic) (Cpa1), and epiplakin 1 (EPPK1) genes;
[12] the method of [11], wherein the combination consists of pancreatic and duodenal homeobox factor-1 (Pdx-1) and carboxypeptidase A1 (pancreatic) (Cpa1); and
[13] the method of any one of [8] to [12], wherein the method for distinguishing, detecting, identifying, collecting, isolating, and/or obtaining a pancreatic progenitor cell is an immunochemical method.

Effects of the Invention

The present invention successfully identified a pancreatic progenitor cell marker and used its expression as an indicator to isolate pancreatic progenitor cells. The present invention is useful in preparing materials for transplantation therapy to treat pancreatic disorders and the like, and searching specific genes as well as in drug discovery that target pancreatic progenitor cells and others. Since the marker gene identified by the present inventors encodes a membrane protein, the marker can be used as an indicator to distinguish, detect, identify, isolate, and/or obtain pancreatic progenitor cells in a viable state that does not contain foreign genes, proteins, and such without the need to use foreign genes, proteins, or such. Since the methods for obtaining pancreatic progenitor cells using the marker of the present invention yield highly pure pancreatic progenitor cells, they are expected to be applied, for example, to drug discovery that targets pancreatic disease such as diabetes.

Figure 1:
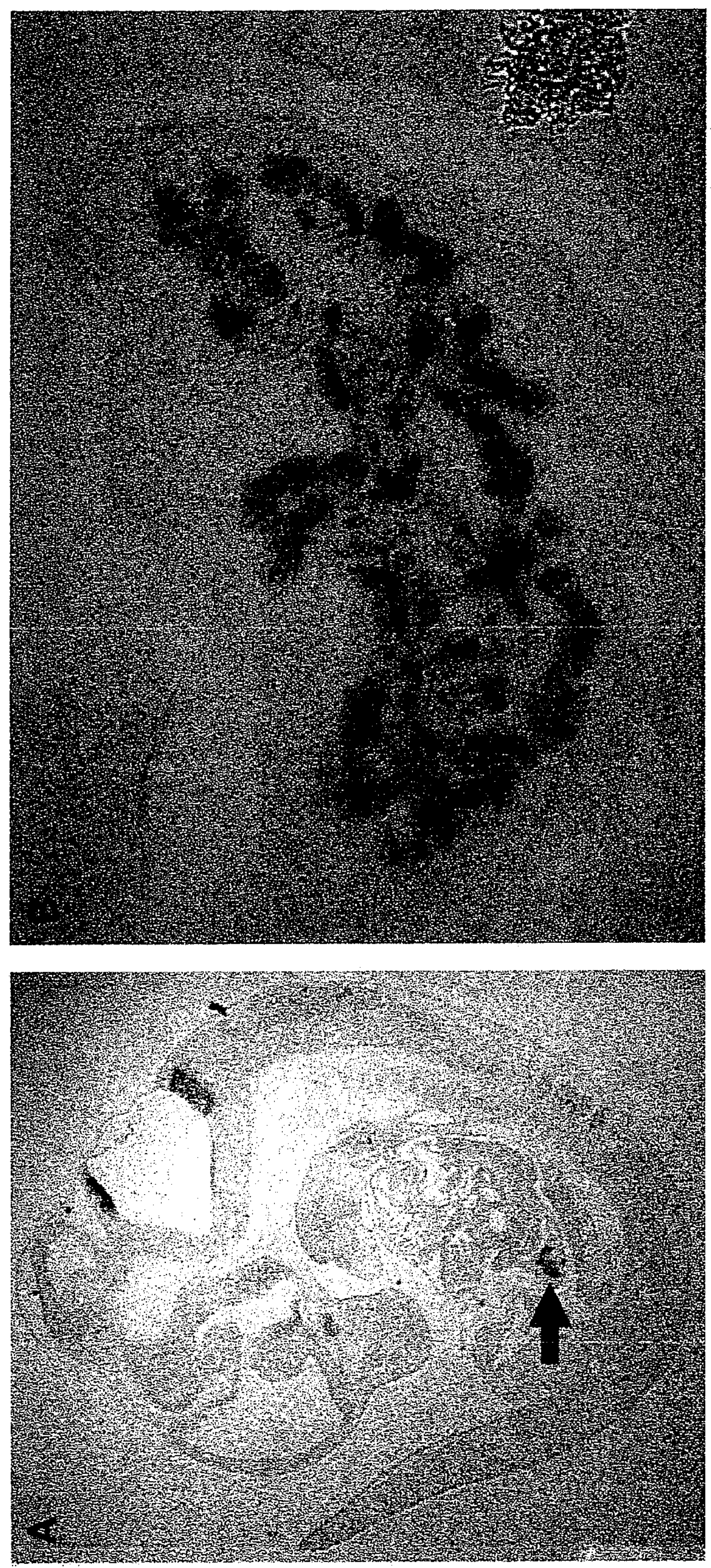
FIG. 1 shows in photographs an expression pattern of Neph3 in fetal mice. A: whole image of E12.5 fetus; B: E12.5 pancreatic primordium.

MODE FOR CARRYING OUT THE INVENTION (Neph3 Gene and Protein)

The present invention provides methods for detecting pancreatic progenitor cells, which use as an indicator the expression of Neph3 which is a selective marker gene for pancreatic progenitor cells. In the present invention, the Neph3 gene includes genes generally known as Neph3, and homologues and counterparts thereof. The Neph3 gene is also referred to as the 65B13 gene (WO 2004/038018). The Neph3 protein refers to a protein encoded by the Neph3 gene. Specifically, the Neph3 gene of the present invention includes, for example, two genes called 65B13-a (SEQ ID NO: 1) and 65B13-b (SEQ ID NO: 3), both of which are alternative isoforms of the Neph3 gene (the amino acid sequences encoded by the respective genes are shown in SEQ ID NOs: 2 and 4). The coding region of 65B13-a is at positions 178 to 2277 in SEQ ID NO: 1, encoding a protein of 700 amino acids. The 17 amino acid residues encoded by the sequence of positions 178 to 228 constitute a signal sequence, while the 17 amino acid residues encoded by the sequence of positions 1717 to 1767 constitute a transmembrane domain. Meanwhile, the coding region of 65B13-b is at positions 127 to 2076 in SEQ ID NO: 3, encoding a protein of 650 amino acids. The 17 amino acid residues encoded by the sequence of positions 127 to 178 constitute a signal sequence, while the 17 amino acid residues encoded by the sequence of positions 1516 to 1566 constitute a transmembrane domain. The N-terminal region before the transmembrane domain is an extracellular domain. Specifically, the extracellular domain is an amino acid sequence encoded by nucleotides at positions 229 to 1716 in 65B13-a or nucleotides at positions 179 to 1515 in 65B13-b.

Furthermore, the Neph3 gene of the present invention also includes, for example, the genes of SEQ ID NOs: 5, 7, 9, 11, 13, 15, 17, 19, and 21 (the amino acid sequences encoded by the genes are shown in SEQ ID NOs: 6, 8, 10, 12, 14, 16, 18, 20, and 22, respectively). The coding region of SEQ ID NO: 5 is at positions 668 to 2767, encoding a protein of 700 amino acids. The 19 amino acid residues encoded by the sequence of positions 668 to 724 constitute a signal sequence, while the 494 amino acid residues encoded by the sequence of positions 725 to 2206 constitute an extracellular domain. The coding region of SEQ ID NO: 7 is at positions 130 to 2229, encoding a protein of 700 amino acids. The 19 amino acid residues encoded by the sequence of positions 130 to 186 constitute a signal sequence, while the 494 amino acid residues encoded by the sequence of positions 187 to 1668 constitute an extracellular domain. The coding region of SEQ ID NO: 9 is at positions 199 to 2097, encoding a protein of 633 amino acids. The 20 amino acid residues encoded by the sequence of positions 199 to 258 constitute a signal sequence, while the 490 amino acid residues encoded by the sequence of positions 259 to 1728 constitute an extracellular domain. The coding region of SEQ ID NO: 11 is at positions 199 to 2322, encoding a protein of 708 amino acids. The 20 amino acid residues encoded by the sequence of positions 199 to 258 constitute a signal sequence, while the 490 amino acid residues encoded by the sequence of positions 259 to 1728 constitute an extracellular domain. The coding region of SEQ ID NO: 13 is at positions 199 to 2322, encoding a protein of 708 amino acids. The 20 amino acid residues encoded by the sequence of positions 199 to 258 constitute a signal sequence, while the 490 amino acid residues encoded by the sequence of positions 259 to 1728 constitute an extracellular domain. The coding region of SEQ ID NO: 15 is at positions 15 to 1913, encoding a protein of 633 amino acids. The 20 amino acid residues encoded by the sequence of positions 15 to 74 constitute a signal sequence, while the 490 amino acid residues encoded by the sequence of positions 75 to 1544 constitute an extracellular domain. The coding region of SEQ ID NO: 17 is at positions 199 to 1947, encoding a protein of 583 amino acids. The 20 amino acid residues encoded by the sequence of positions 199 to 258 constitute a signal sequence, while the 440 amino acid residues encoded by the sequence of positions 259 to 1578 constitute an extracellular domain. The coding region of SEQ ID NO: 19 is at positions 15 to 1763, encoding a protein of 583 amino acids. The 20 amino acid residues encoded by the sequence of positions 15 to 74 constitute a signal sequence, while the 440 amino acid residues encoded by the sequence of positions 75 to 1394 constitute an extracellular domain. The coding region of SEQ ID NO: 21 is at positions 196 to 2259, encoding a protein of 688 amino acids. The 20 amino acid residues encoded by the sequence of positions 196 to 255 constitute a signal sequence, while the 470 amino acid residues encoded by the sequence of positions 256 to 1665 constitute an extracellular domain. In addition, the Neph3 gene of the present invention also includes, for example, the sequences of accession numbers XM_994164, AL136654, XM_512603, XR_012248, XM_541684, and XM_583222.

The Neph3 gene of the present invention includes not only polynucleotides specifically exemplified above but also isoforms, splicing variants, and allelic mutants thereof. Such polynucleotides include the nucleotide sequences of SEQ ID NOs: 1, 3, 5, 7, 9, 11, 13, 15, 17, 19, and 21, preferably sequences of the coding region thereof, and more preferably sequences of the coding region excluding their signal sequence portion, and polynucleotides that hybridize under stringent conditions to the complementary strand of any one of these, or a probe prepared from any one of the above sequences. Such polynucleotides can be obtained from cDNA libraries or genomic libraries of a desired animal by known hybridization methods such as colony hybridization, plaque hybridization, and Southern blotting. The animals from which the Neph3 gene is derived are not particularly limited, and include desired animals such as rodents including mice and rats, mammals including rabbits, hamsters, chickens, dogs, pigs, bovines, goats, and sheep, and primates including monkeys and apes, and humans. With regard to methods for constructing cDNA libraries, one can refer to "Molecular Cloning, A Laboratory Manual 2nd ed." (Cold Spring Harbor Press (1989)). It is also possible to use cDNA libraries and genomic libraries available on the market.

More specifically, in constructing a cDNA library, total RNA is first prepared from cells, organs, tissues, or such (for example, pancreatic primordia, cell samples in which pancreatic progenitor cells are induced by differentiation from pluripotent stem cells, or such) that are expected to express a polynucleotide of the present invention, by known techniques such as guanidine ultracentrifugation (Chirwin et al., Biochemistry (1979) 18: 5294-9) or AGPC method (Chomczynski and Sacchi Anal. Biochem. (1987) 162: 156-9), followed by mRNA purification using an mRNA Purification Kit (Pharmacia), etc. A kit for direct mRNA preparation, such as the QuickPrep mRNA Purification Kit (Pharmacia), may also be used. Next, cDNA is synthesized from the resulting mRNA using reverse transcriptase. cDNA synthesis kits such as the AMV Reverse Transcriptase First-strand cDNA Synthesis Kit (Seikagaku Corporation) are also available commercially. Other methods that use the 5'-RACE method to synthesize and amplify cDNA by PCR may also be used (Frohman et al., Proc. Natl. Acad. Sci. USA (1988) 85: 8998-9002; Belyaysky et al., Nucleic Acids Res. (1989) 17: 2919-32). In addition, in order to construct cDNA libraries containing a high percentage of full-length clones, known techniques such as the oligo-capping method (Maruyama and Sugano. Gene (1994) 138: 171-4; Suzuki. Gene (1997) 200: 149-56) can also be employed. The cDNA obtained in this manner can then be incorporated into a suitable vector. The Neph3 gene can be obtained by screening a library prepared as described above by hybridization using probes prepared based on the sequence of a polynucleotide described above.

The stringent hybridization conditions of the present invention include, for example, hybridization under the post-hybridization wash conditions of "2×SSC, 0.1% SDS, 50° C.", "2×SSC, 0.1% SDS, 42° C.", or "1×SSC, 0.1% SDS, 37° C.", and more stringent hybridization conditions of the present invention include, for example, hybridization under the post-hybridization wash conditions of "2×SSC, 0.1% SDS, 65° C.", "0.5×SSC, 0.1% SDS, 42° C.", "0.2×SSC, 0.1% SDS, 65° C.", or "0.1×SSC, 0.1% SDS, 65° C." (1×SSC: 150 mM NaCl and 15 mM sodium citrate (pH 7.0)). More specifically, it is possible to use a method using Rapid-hyb buffer (Amersham Life Science). The method is carried out as follows. After pre-hybridization is performed at 68° C. for 30 minutes or more, a probe is added and allowed to form hybrids by incubation at 68° C. for one hour or more, followed by washing three times with 2×SSC/0.1% SDS at room temperature for 20 minutes, washing three times with 1×SSC/0.1% SDS at 37° C. for 20 minutes, and finally washing twice with 1×SSC/0.1% SDS at 50° C. for 20 minutes. More preferably, the pre-hybridization solution and hybridization solution contain, for example, 5×SSC, 7% (W/V) SDS, 100 μg/ml denatured salmon sperm DNA, 5×Denhardt's solution (1×Denhardt's solution contains 0.2% polyvinylpyrrolidone, 0.2% bovine serum albumin, and 0.2% Ficoll), and after 30 minutes to one hour of pre-hybridization at 65° C., hybridization is carried out at the same temperature overnight (6 to 8 hours). This can also be carried out using, for example, the Expresshyb Hybridization Solution (CLONTECH), by performing pre-hybridization at 55° C. for 30 minutes or more, adding a labeled probe and incubating at 37° C. to 55° C. for one hour or more, washing three times in 2×SSC, 0.1% SDS at room temperature for 20 minutes each, and washing once at 37° C. for 20 minutes with 1×SSC, 0.1% SDS. Here, conditions of higher stringency can be achieved by increasing the temperature for pre-hybridization, hybridization, or second wash. For example, the pre-hybridization and hybridization temperature can be raised to 60° C., and to 65° C. or 68° C. for higher stringency. In addition to conditions such as salt concentration of the buffer and temperature, a person with ordinary skill in the art can also integrate other conditions such as probe concentration, probe length, and reaction time, to obtain isoforms of the genes of the present invention, allelic mutants, and corresponding genes derived from other organisms. References such as "Molecular Cloning, A Laboratory Manual 2$^{nd}$ ed." (Cold Spring Harbor Press (1989), Sections 9.47-9.58 in particular), "Current Protocols in Molecular Biology" (John Wiley & Sons (1987-1997), Sections 6.3-6.4 in particular), "DNA Cloning 1: Core Techniques, A Practical Approach 2$^{nd}$ ed." (Oxford University (1995), Section 2.10 for conditions in particular) can be referred to for detailed information on hybridization procedures.

Probes to be used in hybridization can be prepared, for example, by the nick translation method, random primer method, PCR, in vitro translation, or the like (Feinberg, A. P. and Vogelstein, B., Anal. Biochem. (1983) 132: 6-13; Feinberg, A. P. and Vogelstein, B., Anal. Biochem. (1984) 137: 266-267; Saiki R K, et al., Science (1985) 230: 1350; Saiki R K, et al., Science (1988) 239: 487). In the random primer method, it is possible to use random hexamer ($pd(N)_6$), random nonamer ($pd(N)_9$), or the like (for example, Random Primer DNA Labeling Kit, Takara Bio Inc., Otsu, Japan). The length of template DNA to be used in probe preparation is, for example, 20 consecutive nucleotides or more, preferably 30, 40, 50, 70, 100, 150, 200, 250, 300, 350, 400, 450, 500, 600, 700, 800, or 1,000 consecutive nucleotides or more. The average probe length is, for example, 20 nucleotides or more, preferably 30, 40, 50, 70, 100, 150, 200, 250, 300, 350, 400, 450, 500, 600, 700, 800, or 1,000 nucleotides or more, and for example, 5000 nucleotides or less, preferably 4,000, 3,000 or 2,000 nucleotides or less. Even if short-length nucleic acids are contained in the probes, such short-length probes hardly affect hybridization because they cannot hybridize with nucleic acids under stringent hybridization conditions.

Specifically, the Neph3 gene of the present invention includes nucleic acids that hybridize under stringent conditions to a polynucleotide comprising the nucleotide sequence of SEQ ID NO: 1, 3, 5, 7, 9, 11, 13, 15, 17, 19, or 21, and/or a complementary sequence thereof, preferably a sequence of the coding region thereof and/or a complementary sequence thereof, and more preferably a sequence of the coding region excluding the signal sequence portion and/or a complementary sequence thereof, or a probe prepared from the polynucleotide, and which are expressed in pancreatic progenitor cells, preferably in multipotent pancreatic progenitor cells. Herein, "expressed in pancreatic progenitor cells" means endogenously expressed in pancreatic progenitor cells. For example, when a target gene is expressed in the pancreatic primordium, it is understood that the gene is expressed in pancreatic progenitor cells. Pancreatic progenitor cells can also be identified by using other pancreatic progenitor cell markers. For example, when a cell expressing a target gene also expresses both Pdx-1 and Ptf1a, it is understood that the cell is a pancreatic progenitor cell. Neph3-positive pancreatic progenitor cells are preferably cells expressing Pdx-1 and Ptf1a, more preferably cells that additionally express Cpa1. Specifically, the Neph3 gene of the present invention is preferably a gene that is expressed in cells endogenously expressing Pdx-1 and Ptf1a, more preferably a gene that is expressed in cells endogenously expressing Pdx-1, Ptf1a, and Cpa1.

The Neph3 genes can be isolated by hybridization. Besides isolation by hybridization, the gene can be amplified, for example, by gene amplification technique (PCR) (Current Protocols in Molecular Biology, John Wiley & Sons (1987) Section 6.1-6.4) using primers designed based on polynucleotides comprising the nucleotide sequence of SEQ ID NO: 1, 3, 5, 7, 9, 11, 13, 15, 17, 19, or 21, and/or a complementary sequence thereof, preferably a sequence of the coding region thereof and/or a complementary sequence thereof, and more preferably a sequence of the coding region excluding the signal sequence, and/or a complementary sequence thereof.

The Neph3 gene also includes polynucleotides that comprise nucleotide sequences that have high identity to the nucleotide sequence of the Neph3 gene exemplified herein, and which are expressed in pancreatic progenitor cells, preferably in multipotent pancreatic progenitor cells. Specifically, the Neph3 gene includes polynucleotides that comprise a nucleotide sequence that has high identity, specifically 70% or higher, preferably 80% or higher, more preferably 85% or higher, and sill more preferably 90% or higher (for example, 95% or higher, 96% or higher, 97% or higher, 98% or higher, or 99% or higher sequence identity) to the nucleotide sequence of SEQ ID NO: 1, 3, 5, 7, 9, 11, 13, 15, 17, 19, or 21, preferably a sequence of the coding region thereof, and more preferably a sequence of the coding region excluding the signal sequence portion, and which are expressed in pancreatic progenitor cells, preferably in multipotent pancreatic progenitor cells.

The Neph3 gene of the present invention also includes polynucleotides that have high identity to the amino acid sequences of proteins encoded by the Neph3 genes exemplified herein, and which are expressed in pancreatic progenitor cells, preferably in multipotent pancreatic progenitor cells. Specifically, the Neph3 gene of the present invention includes polynucleotides encoding an amino acid sequence that has high identity, specifically 70% or higher, preferably 80% or higher, more preferably 85% or higher, and sill more preferably 90% or higher (for example, 95% or higher, 96% or higher, 97% or higher, 98% or higher, or 99% or higher sequence identity) to amino acid sequences encoded by sequences of the coding region of SEQ ID NO: 1, 3, 5, 7, 9, 11, 13, 15, 17, 19, or 21, preferably sequences of the coding region thereof, preferably amino acid sequence encoded by sequences of the coding region excluding the signal sequence portion, and which are expressed in pancreatic progenitor cells, preferably in multipotent pancreatic progenitor cells.

Such sequence identity can be determined based on the BLAST algorithm (Altschul Proc. Natl. Acad. Sci. USA (1990) 87: 2264-8; Karlin and Altschul, Proc. Natl. Acad. Sci. USA (1993) 90: 5873-7). The BLASTP and BLASTN programs for determining amino acid and nucleotide sequence identities, respectively (Altschul et al., J. Mol. Biol. (1990) 215: 403-10), are developed based on this algorithm, and can be used to determine sequence identity. Specifically, the analytical method can be referred to, for example, on the web pages of National Center for Biotechnology Information (NCBI). A target sequence to be compared is aligned with a reference sequence, for example, sequence of the coding region of SEQ ID NO: 1, 3, 5, 7, 9, 11, 13, 15, 17, 19, or 21 (specifically, the nucleotide sequence of positions 178 to 2280 in SEQ ID NO: 1; positions 127 to 2079 in SEQ ID NO: 3; positions 668 to 2770 in SEQ ID NO: 5; positions 130 to 2232 in SEQ ID NO: 7; positions 199 to 2100 in SEQ ID NO:

9; positions 199 to 2325 in SEQ ID NO: 11; positions 15 to 2325 in SEQ ID NO: 13; positions 15 to 1916 in SEQ ID NO: 15; positions 199 to 1950 in SEQ ID NO: 17; positions 15 to 1766 in SEQ ID NO: 19; or positions 196 to 2262 in SEQ ID NO: 21) or an amino acid sequence encoded by the sequence of SEQ ID NO: 2, 4, 6, 8, 10, 12, 14, 16, 18, 20, or 22, respectively. Sequence identity is calculated as the ratio between number of identical nucleotides or amino acids and total number of nucleotides or amino acids in the reference sequence (including inserted gaps in the reference sequence but excluding inserted gaps outside of the reference sequence). The gaps inserted in the reference sequence are calculated as mismatches in the alignment.

In the present invention, the Neph3 genes also comprise polynucleotides that comprise a nucleotide sequence with one or more nucleotide insertions, substitutions, deletions, and/or additions (addition refers to, for example, adding one or more nucleotides to either or both of the ends of a nucleotide sequence) in sequences of the coding region of SEQ ID NO: 1, 3, 5, 7, 9, 11, 13, 15, 17, 19, or 21 (the nucleotide sequence of positions 178 to 2280 in SEQ ID NO: 1; positions 127 to 2079 in SEQ ID NO: 3; positions 668 to 2770 in SEQ ID NO: 5; positions 130 to 2232 in SEQ ID NO: 7; positions 199 to 2100 in SEQ ID NO: 9; positions 199 to 2325 in SEQ ID NO: 11; positions 15 to 2325 in SEQ ID NO: 13; positions 15 to 1916 in SEQ ID NO: 15; positions 199 to 1950 in SEQ ID NO: 17; positions 15 to 1766 in SEQ ID NO: 19; or positions 196 to 2262 in SEQ ID NO: 21), and which are expressed in pancreatic progenitor cells, preferably in multipotent pancreatic progenitor cells. The number of different nucleotides is not particularly limited; however, it is, for example, 500 or less, preferably 450 or less, 400 or less, 350 or less, 300 or less, 250 or less, 200 or less, 150 or less, 100 or less, 50 or less, or 30 or less (20 or less, 10 or less, or 5 or less). In the present invention, the Neph3 genes also comprise polynucleotides that encode an amino acid sequence with one or more amino acid insertions, substitutions, deletions, and/or additions (addition refers to adding one or more amino acids to either or both of the termini of an amino acid sequence) in amino acid sequences (SEQ ID NO: 2, 4, 6, 8, 10, 12, 14, 16, 18, 20, or 22) encoded by sequences of the coding region of SEQ ID NO: 1, 3, 5, 7, 9, 11, 13, 15, 17, 19, or 21, and which are expressed in pancreatic progenitor cells, preferably in multipotent pancreatic progenitor cells. The number of different amino acids is not particularly limited; however, it is, for example, 500 or less, preferably 250 or less, 200 or less, 180 or less, 150 or less, 120 or less, 100 or less, 80 or less, 70 or less, 60 or less, 50 or less, 40 or less, 30 or less, 20 or less, or 10 or less (for example, 5, 4, 3, 2, or 1). Such variants are generally seen as isoforms or polymorphisms. Furthermore, it is well known that a mutant polypeptide having an amino acid sequence with one or more amino acid deletions, insertions, substitutions, or additions retains the same biological activity as the original polypeptide (Mark et al., Proc. Natl. Acad. Sci. USA (1984) 81: 5662-6; Zoller and Smith, Nucleic Acids Res. (1982) 10: 6487-500; Wang et al., Science (1984) 224: 1431-3; Dalbadie-McFarland et al., Proc. Natl. Acad. Sci. USA (1982) 79: 6409-13). Herein, "one or more nucleotide insertions, substitutions, deletions, and/or additions in a polynucleotide" and "one or more amino acid insertions, substitutions, deletions, and/or additions in an amino acid sequence" mean that multiple nucleotides or amino acids in a polynucleotide or amino acid sequence are altered by known technical methods such as site-directed mutagenesis or by naturally occurring substitution and the like. In the case of polynucleotides, single nucleotide polymorphisms (SNP) are also included in the meaning. The number of altered nucleotides or amino acids is, for example, 1 to 30, preferably 1 to 20, more preferably, 1 to 10, even more preferably 1 or several (9 or less) nucleotides or amino acids, particularly preferably 1 to 4, and most preferably one or two, and these alterations may be insertions, substitutions, deletions, and/or additions. Such altered nucleotide sequences can preferably comprise a sequence with one or more amino acid mutations (for example, one to several, or 1, 2, 3, or 4 amino acid mutations) that do not affect the protein function. Alternatively, such altered nucleotide sequences can be a sequence with mutations in which one or more codons are substituted with different codons encoding the same amino acids so that the encoded amino acid sequences remain unaltered (silent mutations). Preferably, the altered amino acid sequences can be those with one or more (for example, one to several, or 1, 2, 3, or 4) conservative amino acid substitutions. Herein, "conservative substitution" means that one or more amino acid residues are substituted with other chemically similar amino acids so as not to substantially alter the protein function. For example, conservative substitution includes substitution of a hydrophobic residue with a different hydrophobic residue or substitution of a polar residue with a different polar residue having equivalent electric charge. Every amino acid that can be altered to yield a functionally similar amino acid by such substitution is known in the art. Specifically, non-polar (hydrophobic) amino acids include, for example, alanine, valine, isoleucine, leucine, proline, tryptophan, phenylalanine, and methionine; polar (neutral) amino acids include, for example, glycine, serine, threonine, tyrosine, glutamine, asparagine, and cysteine; positively charged (basic) amino acids include, for example, arginine, histidine, and lysine; and negatively charged (acidic) amino acids include, for example, aspartic acid and glutamic acid.

More specifically, the Neph3 gene of the present invention includes the following polynucleotides:

(i) a polynucleotide comprising the coding sequence of SEQ ID NO: 1, 3, 5, 7, 9, 11, 13, 15, 17, 19, or 21;

(ii) a polynucleotide that comprises the nucleotide sequence encoding the amino acid sequence of SEQ ID NO: 2, 4, 6, 8, 10, 12, 14, 16, 18, 20, or 22, and which is expressed in pancreatic progenitor cells;

(iii) a polynucleotide that comprises a nucleotide sequence with one or more nucleotide insertions, substitutions, deletions, and/or additions (addition refers, for example, to adding to either or both of the ends) in the coding sequence of SEQ ID NO: 1, 3, 5, 7, 9, 11, 13, 15, 17, 19, or 21, and which is expressed in pancreatic progenitor cells;

(iv) a polynucleotide that comprises a nucleotide sequence encoding an amino acid sequence with one or more amino acid insertions, substitutions, deletions, and/or additions (addition refers, for example, to adding to either or both of the termini) in the amino acid sequence encoded by SEQ ID NO: 1, 3, 5, 7, 9, 11, 13, 15, 17, 19, or 21 (the amino acid sequence of SEQ ID NO: 2, 4, 6, 8, 10, 12, 14, 16, 18, 20, or 22), and which is expressed in pancreatic progenitor cells;

(v) a polynucleotide that hybridizes under stringent conditions to the complementary strand of a polynucleotide comprising the coding sequence of SEQ ID NO: 1, 3, 5, 7, 9, 11, 13, 15, 17, 19 or 21, and which is expressed in pancreatic progenitor cells;

(vi) a polynucleotide that comprises a nucleotide sequence that has high identity to the coding sequence of SEQ ID NO: 1, 3, 5, 7, 9, 11, 13, 15, 17, 19, or 21, and which is expressed in pancreatic progenitor cells; and (vii) a polynucleotide that comprises a nucleotide sequence encoding an amino acid sequence that has high identity to the amino acid sequence encoded by SEQ ID NO: 1, 3, 5, 7, 9, 11, 13, 15, 17, 19, or 21 (the amino acid sequence of SEQ ID NO: 2, 4, 6, 8, 10, 12, 14, 16, 18, 20, or 22), and which is expressed in pancreatic progenitor cells.

In the present invention, the Neph3 protein also includes polypeptides encoded by the Neph3 genes described above. Specifically, the protein comprises the following polypeptides:

(i) a polypeptide comprising the amino acid sequence of SEQ ID NO: 2, 4, 6, 8, 10, 12, 14, 16, 18, 20, or 22;

(ii) a polypeptide that comprises an amino acid sequence with one or more amino acid insertions, substitutions, deletions, and/or additions (addition refers, for example, to adding to either or both of the termini) in the amino acid sequence of SEQ ID NO: 2, 4, 6, 8, 10, 12, 14, 16, 18, 20, or 22, and which is expressed in pancreatic progenitor cells;

(iii) a polypeptide encoded by a polynucleotide that hybridizes under stringent conditions to the complementary strand of a polynucleotide encoding the amino acid sequence of SEQ ID NO: 2, 4, 6, 8, 10, 12, 14, 16, 18, 20, or 22 (for example, a polynucleotide comprising the coding sequence of SEQ ID NO: 1, 3, 5, 7, 9, 11, 13, 15, 17, 19, or 21), and which is expressed in pancreatic progenitor cells; and (iv) a polypeptide that comprises an amino acid sequence with high identity to the amino acid sequence of SEQ ID NO: 2, 4, 6, 8, 10, 12, 14, 16, 18, 20, or 22, and which is expressed in pancreatic progenitor cells.

A polynucleotide that constitutes the Neph3 gene can be appropriately produced by hybridization or PCR from cells expressing the Neph3 gene, or by chemical synthesis, or the like. The nucleotide sequence of the obtained polynucleotide can be determined by conventional methods, for example, the dideoxynucleotide chain termination method (Sanger et al., Proc. Natl. Acad. Sci. USA (1977) 74: 5463). Alternatively, the sequence can also be analyzed using an appropriate DNA sequencer.

The Neph3 protein can be collected from cells expressing the Neph3 gene described above. For example, the Neph3 gene is expressed using a desired expression vector, and the produced protein is collected. A protein encoded by the Neph3 gene of the present invention (Neph3 protein) is typically a single-pass transmembrane protein having immunoglobulin domains, and possibly a type I membrane protein which has an extracellular domain on its N-terminus, and a cytoplasmic domain on its C-terminus. The Neph3 protein preferably contains five immunoglobulin domains in its extracellular domain. The extracellular domain of a polypeptide can be identified by using the PSORT program (Nakai, K. and Horton, P., Trends Biochem. Sci, (1999) 24(1): 34-35; psort.ims.u-tokyo.ac.jp/) or such. Specifically, the extracellular domains determined by using the PSORT program are the amino acid sequence of positions 21 to 510 in the amino acid sequence of SEQ ID NO: 2, 4, 10, 12, 14, or 16, the amino acid sequence of positions 20 to 513 in the amino acid sequence of SEQ ID NO: 6 or 8, the amino acid sequence of positions 21 to 460 in the amino acid sequence of SEQ ID NO: 18 or 20, and the amino acid sequence of positions 21 to 490 in the amino acid sequence of SEQ ID NO: 22. The Neph3 genes of the present invention may also be expressed, for example, in dopamine-producing neuron progenitor cells in the midbrain. Alternatively, the Neph3 genes of the present invention may be expressed in GABA-producing neuron progenitor cells. Preferably, the Neph3 proteins have a self-binding activity through immunoglobulin domains (WO 2004/038018).

(Pancreatic Progenitor Cells)

Herein, a pancreatic progenitor cell refers to a progenitor cell committed to pancreatic cell. More specifically, a pancreatic progenitor cell refers to a cell that is not terminally differentiated and is primarily destined to differentiate into at least any cell that constitutes a mature pancreas, or a cell whose phenotype is equivalent to that of the cell described above. Such cells may be endodermal cells, for example, those derived from endodermal cells of a gastrointestinal endodermal lineage. For example, pancreatic progenitor cells may be cells in the pancreatic primordium of embryos or culture thereof. Alternatively, pancreatic progenitor cells may be cells induced by differentiation from endodermal stem cells, gastrointestinal undifferentiated endodermal cells, embryonic stem (ES) cells, or other pluripotent stem (PS) cells. Herein, "stem cell" refers to a cell having the ability to transform into a specific cell upon receiving instructions to transform into a specific cell, i.e., the ability to differentiate into the specific cell. In addition, the stem cell has self-renewal/regeneration ability over a long period of time in an undifferentiated state before transformation. Embryonic stem cells (ES cells), adult stem cells (iPS cells), and embryonic germ cells can be harvested from embryos, adults, and fetuses, respectively, all of which are included in the stem cells of the present invention. ES cells are cells harvested during the period of differentiation of a fertilized egg to develop a fetus, which is an early embryonic stage. ES cell is also referred to as a pluripotent stem cell because it has properties to develop into any type of cells in a body. ES cells can be harvested from inner layer cells (inner cell mass) of blastocyst five or six days after fertilization and cultured. Furthermore, induced pluripotent stem cells (iPS cells) which are conferred with pluripotency by initializing somatic cells such as skin cells through introduction of Oct3, Sox2, Klf4, and the like are also included in the artificial pluripotent stem cells. In addition, pluripotent cells induced from adipocytes are also included in the stem cells. Various types of stem cells such as ES cells, iPS cells, and pluripotent cells induced from adipocytes can be used in the present invention, as long as they are capable of differentiating into various types of cells.

There are various known methods for differentiating pancreatic progenitor cells from pluripotent stem cells or the like (Kubo A et al., Development (2004) 131: 1651-1662; Tada S et al., Development (2005) 132: 4363-4374; Yasunaga M et al., Nat Biotechnol (2005) 23: 1542-1550; Gadue P et al., Proc Natl Acad Sci USA (2006) 103: 16806-16811; D'Amour K A et al., Nat Biotechnol (2005) 23: 1534-1541; McLean A B et al., STEM CELLS (2007) 25: 29-38; D'Amour K A et al., Nat Biotechnol (2006) 24: 1392-1401; Shiraki, N. et al., Stem Cells (2008) 26: 874-885; Kroon E et al., Nat. Biotechnol. (2008) 26(4): 443-52). However, the ratio of pancreatic progenitor cells obtained by the above-described methods is not necessarily high. The methods of the present invention can dramatically increase the purity of viable pancreatic progenitor cells in cell samples containing pancreatic progenitor cells differentiated by the methods described in the above references.

In the present invention, the pancreatic progenitor cell refers to a cell that can differentiate into at least any of endocrine cells, exocrine cells, or duct cells in pancreas. The pancreatic progenitor cells are preferably cells that can differentiate into at least endocrine cells. For example, pancreatic cells may be cells that have the ability to differentiate into at least any of α cells, β cells, δ cells, and pancreatic polypeptide (PP)-producing cells, preferably into all of these cells. Alternatively, the pancreatic progenitor cells of the present invention preferably have the ability to differentiate into at least β cells. Furthermore, the pancreatic progenitor cells do not yet have, for example, any of the characteristics of mature pancreatic cells. For example, at least the pancreatic progenitor cells do not secrete an equivalent amount of the same polypeptides as mature pancreatic endocrine cells (specifically, for example, the secretion level is ½ or less than that of mature cells, preferably ⅓ or less, ⅕ or less, ⅛ or less, 1/10 or less, 1/20 or less, 1/30 or less, or 1/50 or less, or not detectable). For example, the pancreatic progenitor cells do not secrete any of insulin, glucagon, somatostatin, and PP equivalently as mature cells (specifically, for example, the secretion levels are ½ or less than those of mature cells, preferably ⅓ or less, ⅕ or less, ⅛ or less, 1/10 or less, 1/20 or less, 1/30 or less, or 1/50 or less, or not detectable). Alternatively, cellular maturity can also be assessed by examining the expression of marker genes characteristic of each cell type, and such methods are well known to those skilled in the art (Shiraki, N. et al., Stem Cells (2008) 26: 874-885). In a preferred embodiment, the expression levels of genes that are known to be significantly elevated in mature pancreatic endocrine cells are significantly low in pancreatic progenitor cells as compared to mature cells (the levels are, for example, 70% or less, 60% or less, 50% or less, 40% or less, 30% or less, 20% or less, 10% or less, or 5% or less, or not detectable). Such genes include, for example, genes encoding proteins selected from insulin 1 (Ins1), insulin 2 (Ins2), glucagon (Gcg), pancreatic polypeptide (Ppy), somatostatin (Sst), Nkx6.1, cytokeratin 19 (CK19), islet amyloid polypeptide (Iapp) (Nishi M et al., Proc Natl Acad Sci USA (1989) 86: 5738-5742), Kir6.2 (Sakura H, et al., FEBS Lett (1995) 377: 338-344), glucose transporter 2 (Glut2), amylase, and dolichos biflorus agglutinin (DBA).

In the present invention, the pancreatic progenitor cells also include multipotent pancreatic progenitor cells. "Multipotent pancreatic progenitor cells" (also referred to as pancreatic multipotent progenitor cells) refers to pancreatic progenitor cells retaining multipotency. Specifically, multipotent pancreatic progenitor cells may be cells that have the ability to differentiate into the three types of cells that constitute pancreas, i.e., endocrine cell, exocrine cell, and duct cell. Endocrine cells include, for example, α cells, β cells, δ cells, and PP cells. Whether cells can differentiate into endocrine cells can be confirmed by assessing their differentiation into any of the cells described above. Markers specific to each cell (for example, glucagon, insulin, somatostatin, and PP each corresponds to the above-described cells) are known. Exocrine cell markers include amylase. Duct cell markers include, for example, DBA. Cell differentiation can be assessed by using these markers or such. The multipotent pancreatic progenitor cells express, for example, pancreatic and duodenal homeobox factor-1 (Pdx-1), pancreas specific transcription factor-1a (Ptf1a), or carboxypeptidase A1 (pancreatic) (Cpa1). The multipotent pancreatic progenitor cells preferably express Pdx-1 and Ptf1a, and more preferably also express Cpa1.

Following are well known to those skilled in the art: pancreatic and duodenal homeobox factor-1 (Pdx-1) (accession NM_000209.3, code sequence (CDS) 109-957, NP_000200.1; NM_008814.3, CDS 109-960, NP_032840.1; XM_543155.2, CDS 1-1596, XP_543155.2; XM_509600.2, CDS 113-961, XP_509600.2; XM_583722.3, CDS 1-855, XP_583722.1; XM_001234635.1, CDS 1-693, XP_001234636.1), Ptf1a (pancreas specific transcription factor-1a (Ptf1a) (accession NM_178161.2, CDS 1-984, NP_835455.1; NM_018809.1, CDS 199-1170, NP_061279.1; NM_207641.2, CDS 89-883, NP_997524.1; XM_001146416.1, CDS 1-579, XP_001146416.1; NM_053964.1, CDS 234-1211, NP_446416.1), Carboxypeptidase A1 (pancreatic) (Cpa1) (accession NM_001868.1, CDS 8-1264, sig_peptide 8-55, mat_peptide 56-1264, NP_001859.1, sig_peptide 1-16, mat_peptide 17-419; NM_174750.2, CDS 27-1283, sig_peptide 27-74, mat_peptide 375-1283, NP_777175.1, sig_peptide 1-16, mat_peptide 117-419; NM_025350.3, CDS 244-1500, NP_079626.2; XM_851827.1, CDS 30-1313, XP_856920.1; NM_016998.2, CDS 309-1565, sig_peptide 312-356, mat_peptide 639-1565; NM_204584.1, CDS 17-1273, sig_peptide 17-67, mat_peptide 353-1273), and epiplakin 1 (EPPK1) (NM_031308.1 (CDS 14-15283), XM_372063 (CDS 1-7185); NM_144848.2 (CDS 1134-20777), NM_173025 (CDS 95-2305), XM_910512 (CDS 1-7725), NP_112598, XM_001074770 (CDS 1-10374), XP_001074770, XM_001059215 (CDS 1-10086), XP_001059215, NM_144848.2 (CDS 1134-20777), NP_659097). Expression of these can be detected by methods known to those skilled in the art.

(Endodermal Cell Samples)

Herein, "endodermal cell sample" refers to a cell sample mainly consisting of endodermal cells. The endoderm is formed by undifferentiated cells in the early vertebrate embryo, which have the ability to differentiate into every type of somatic cells (pluripotent cells). A fertilized egg first becomes a blastula, which is a globular cell mass, by somatic division. A portion of the blastula surface invaginates (gastrulation). The invaginated portion becomes a primitive gut. An embryo at this stage is called gastrula. Thus, difference between the outer side and inner side (primitive gut side) becomes distinct. The outer side becomes the ectoderm, while the inner side becomes the endoderm. Cells in the endoderm as well as endoderm lineage cells derived from the endoderm are endodermal cells. Alternatively, endodermal cells can be prepared by artificially differentiating endodermal cell progenitor cells such as multipotent stem cells.

An "endodermal cell sample" of the present invention may be a sample of pure endodermal cells or a sample partially containing other cells. In an endodermal cell sample of the present invention, the percentage of endodermal cells in the total cells is preferably 50% or more, more preferably 60% or more, 70% or more, 80% or more, 90% or more, 95% or more, or 100%. The "endodermal cell sample" of the present invention includes any cell samples as long as pancreatic progenitor cells can be prepared from the cell samples by using a translated product or transcript of the Neph3 gene. In the present invention, an "endodermal cell sample" of the present invention is preferably prepared by performing the step of selecting or enriching the endoderm to some extent.

Such endodermal cell samples can be prepared by known methods based on the induction of stem cells such as described in the above references. Alternatively, it is possible to use samples obtained from fetuses.

(Neuronal-lineage-cell Depleted Cell Sample)

A "central nervous system-lineage-cell depleted cell sample" refers to a cell sample in which central nervous system cells and cells capable of differentiating into central nervous system cells are depleted. Meanwhile, a "neuronal-lineage-cell depleted cell sample" refers to a cell sample in which nerve cells and cells capable of differentiating into nerve cells are depleted. "Cells capable of differentiating into nerve cells" refers to ectodermal progenitor cells before differentiation into the nerve. The ectoderm is formed by undifferentiated cells in the early vertebrate embryo, which have the ability to differentiate into every type of somatic cells (pluripotent cells). A fertilized egg first becomes a blastula, which is a globular cell mass, by somatic division. A portion of the blastula surface invaginates (gastrulation). The invaginated portion becomes a primitive gut. An embryo at this stage is called gastrula. Thus, difference between the outer side and inner side (primitive gut side) becomes distinct. The outer side becomes the ectoderm, while the inner side becomes the endoderm. Cells in the ectoderm as well as ectoderm lineage cells derived from the ectoderm are ectodermal cells. The ectodermal cells also include cells prepared by artificially differentiating ectoderm lineage cells from ectodermal cell progenitor cells such as multipotent stem cells. In the present invention, preferably neuronal lineage cell-depleted cell samples, more preferably ectoderm-lineage-cell depleted cell samples are used as central-nervous-system-cell depleted cell samples. Such neuronal-lineage-cell depleted cell samples may be, for example, cell samples in which neuronal lineage cells are depleted, i.e., neuronal-lineage-cell depleted cell samples. The central-nervous-system-cell depleted cell samples may be, for example, cell samples in which central nervous system (CNS) lineage cells are depleted, i.e., CNS-lineage-cell depleted cell samples. These cell samples may be ectodermal cell-depleted cell samples.

Nerve cells and cells capable of differentiating into nerve cells also include nerve cells and cells that can be induced from stem cells to differentiate into the nerve. The "neuronal-lineage-cell depleted cell sample" also includes cell samples from which nerve cells and cells that can be induced from stem cells to differentiate into the nerve are depleted.

Such "neuronal-lineage-cell depleted cell sample" may be a cell sample strictly depleted of nerve cells, or a sample that partially contains other cells. Preferred neuronal-lineage-cell depleted cell samples of the present invention are cell samples that are completely depleted of nerve cells and cells capable of differentiating into nerve cells (however, they are not cells that can differentiate into the endoderm), and which contain endodermal cells. The "neuronal-lineage-cell depleted cell sample" of the present invention includes any cell samples as long as pancreatic progenitor cells can be prepared from the cell samples by using a translated product or transcript of the Neph3 gene. In the present invention, the "neuronal-lineage-cell depleted cell sample" is preferably prepared by performing the step of removing nerve cells and cells capable of differentiating into nerve cells to some extent.

Such "neuronal-lineage-cell depleted cell samples" can be prepared by removing cells capable of differentiating into the nerve using known methods based on the induction of stem cells, as described in the above references.

(Abdomen-derived Cell Sample)

An "abdomen-derived cell sample" refers to a cell sample that can be prepared from an abdomen. In this case, cells that can be prepared from a fetal abdomen are preferred. Herein, the "abdomen" refers to parts other than the head, upper limbs (arms), and lower limbs (legs).

The abdomen-derived cell sample may be a pure cell sample containing only abdominal cells, or a sample partially containing other cells. In an abdomen-derived cell sample of the present invention, the percentage of abdominal cells in the total cells is preferably 50% or more, more preferably 60% or more, 70% or more, 80% or more, 90% or more, or 95% or more. The "abdomen-derived cell sample" of the present invention includes any cell samples as long as pancreatic progenitor cells can be prepared from the cell samples by using a translated product or transcript of the Neph3 gene. An "abdomen-derived cell sample" of the present invention is preferably prepared by performing the step of selecting or enriching abdominal cells to some extent.

(Detection Method)

In the methods of the present invention, pancreatic progenitor cells are detected (including the meaning of distinguished, identified, collected, prepared, selected, enriched, isolated, and/or obtained) by detecting the Neph3 gene expression. Specifically, the methods of the present invention for detecting pancreatic progenitor cells comprise the step of detecting the expression of the Neph3 gene in a cell sample potentially containing pancreatic progenitor cells. The cell sample potentially containing pancreatic progenitor cells refers to a cell sample in which pancreatic progenitor cells are expected to be detected (including the meaning of distinguished, identified, collected, prepared, selected, enriched, isolated, and/or obtained). Such cell sample may be, for example, a cell sample that is known to contain pancreatic progenitor cells, or a cell sample that is expected to contain pancreatic progenitor cells. Preferred cell samples are cell samples containing pancreatic progenitor cells. When the Neph3 expression is detected in a cell sample, the sample is suggested to contain pancreatic progenitor cells. On the other hand, when Neph3 expression is not detected, it is suggested that the sample does not contain pancreatic progenitor cells. Alternatively, when Neph3-expressing cells are detected, the cells are suggested to be pancreatic progenitor cells. The cells can be collected to isolate pancreatic progenitor cells.

Herein, detection of pancreatic progenitor cells may be detecting the presence or absence of pancreatic progenitor cells, and may be, for example, a method for identifying whether pancreatic progenitor cells are contained in a cell sample. Alternatively, detection may be assessing whether a cell is a pancreatic progenitor cell, determining the distribution of pancreatic progenitor cells (for example, in tissue sections or whole organs by hybridization or the like), or measuring the pancreatic progenitor cell ratio. Meanwhile, the methods for detecting pancreatic progenitor cells comprise a desired process including detection of pancreatic progenitor cells. Such methods may include, for example, methods that distinguish, identify, collect, prepare, select, enrich, isolate, and/or obtain pancreatic progenitor cells after detecting the cells. A method for detecting pancreatic progenitor cells is included in a desired method comprising, for example, the steps of detecting, distinguishing, identifying, preparing, selecting, enriching, collecting, isolating, and/or obtaining pancreatic progenitor cells. For example, the methods of the present invention are included in methods for assaying or screening compounds that regulate the differentiation of pancreatic progenitor cells, which are described below.

A cell sample to be used in the methods of the present invention for detecting pancreatic progenitor cells may be a population of cells isolated or cultured by desired methods. Such cell sample is, for example, preferably a culture product containing pancreatic progenitor cells resulting from in vitro differentiation. In vitro differentiation of pancreatic progenitor cells can be achieved by known methods using, as a starting material, ES cells, induced pluripotent stem cells (iPS), or multipotent cells induced from adipocytes, or the like. Alternatively, such cell sample may be cells derived from a pancreatic primordium. Meanwhile, a cell sample may contain Neph3-positive cells besides pancreatic progenitor cells, as long as the sample contains Neph3-positive pancreatic progenitor cells. Preferably, a cell sample is a sample that contains pancreatic progenitor cells as the highest proportion of Neph3-positive cells. The detection methods of the present invention are also methods for detecting and/or producing cell groups (populations) comprising pancreatic progenitor cells.

Cell samples may be, for example, cell suspensions or tissue sections. Alternatively, cell samples may be individually isolated single cells. The Neph3 expression may be detected in individual cells by cytometry or such. The preferred cell sample does not contain or contains a low ratio of central nervous system progenitor cells (dopamine-producing neuron progenitor cells and GABA-producing neuron progenitor cells) expressing Neph3. For this purpose, it is preferable to prepare a cell sample that does not contain such central nervous system cells. For example, it is preferable to use cell samples that do not contain central nervous system progenitor cells such as pancreatic primordium-derived cells and cell samples of pancreatic progenitor cells differentiated from multipotent stem cells. However, even if a cell sample contains neuron progenitor cells, whether the Neph3-positive cells are pancreatic progenitor cells or neuron progenitor cells can be easily tested by using other pancreatic progenitor cell markers and neuron progenitor cell markers. The methods of the present invention for detecting pancreatic progenitor cells also relate to methods that additionally comprise the step of detecting or selecting (or removing) dopamine-producing neuron progenitor cells and GABA-producing neuron progenitor cells from a cell sample. The present invention also relates to methods that additionally comprise the step of detecting pancreatic progenitor cell markers other than Neph3. Furthermore, the preferred cell sample of the present invention does not contain ectodermal cells, or contains a low ratio of ectodermal cells relative to endodermal cells. Preferably, cells in the cell sample consist of endodermal cells or progenitor cells thereof. Alternatively, in the present invention, the cell sample may be a product of induced differentiation of multipotent stem cells into endodermal cells (for example, pancreatic progenitor cells). However, even if a cell sample contains a low ratio of neuron progenitor cells, pancreatic progenitor cells can be detected or selected in a highly specific manner by the methods of the present invention when the sample contains a sufficient number of pancreatic progenitor cells. Cell samples to be used in the methods of the present invention preferably contain a higher ratio of pancreatic progenitor cells than neuron progenitor cells. More preferably, the cell sample contains pancreatic progenitor cells, for example, twice or more, more preferably three times or more, four times or more, five times or more, six times or more, seven times or more, eight times or more, nine times or more, ten times or more, 20 times or more, or 30 times or more of the number of neuron progenitor cells. In the preferable cell samples to be used in the methods of the present invention, the percentage of pancreatic progenitor cells is the highest or expected to be the highest among Neph3-positive cells. For example, in such cell samples, 50% or more, more preferably 60% or more, 70% or more, 75% or more, 80% or more, 85% or more, 90% or more, or 95% or more of Neph3-positive cells are pancreatic progenitor cells. Furthermore, in the cell samples used in the present invention, preferably 50% or more, more preferably 60% or more, 70% or more, 75% or more, 80% or more, 85% or more, 90% or more, or 95% or more of Neph3-positive cells are Pdx-1-, Ptf1a-, Cpa1-, and/or EPPK1-positive cells.

Furthermore, it is preferable that cell samples that potentially contain pancreatic progenitor cells do not contain mature pancreatic cells, in particular, mature β cells, or contain them at a lower ratio than pancreatic progenitor cells. For example, the cell samples do not contain mature β cells, preferably any mature endocrine cells (α cells, β cells, δ cells, and PP cells), or the total number of mature endocrine cells in the cell sample is smaller than the number of pancreatic progenitor cells. More preferably, the cell samples do not contain any mature pancreatic cells including exocrine cells and duct cells, or the total number of mature pancreatic cells in the cell sample is smaller than the number of pancreatic progenitor cells. For example, it is preferable that cells contained in the cell samples do not yet have any of the characteristics of mature pancreatic cells. For example, none of the cells contained in the cell samples significantly secrete the same polypeptides as mature pancreatic endocrine cells (specifically, for example, the secretion levels are ½ or less, preferably ⅓ or less, ⅕ or less, ⅛ or less, 1/10 or less, 1/20 or less, 1/30 or less, or 1/50 or less than those of mature cells, or not detectable). For example, the cell samples do not contain cells that significantly secrete insulin (more specifically, the same secretion level as mature β cells, for example, 60% or more, 70% or more, or 80% or more of the insulin secretion level of mature β cells). For example, cells contained in the cell samples do not significantly secrete any of insulin, glucagon, somatostatin, pancreatic polypeptide (PP), and amylase (specifically, for example, the secretion levels are ½ or less, preferably ⅓ or less, ⅕ or less, ⅛ or less, 1/10 or less, 1/20 or less, 1/30 or less, or 1/50 or less than those of mature cells, or not detectable). Such cell samples include, for example, cell samples that do not contain mature pancreatic cells, such as pancreatic primordium-derived cells and culture products of pancreatic progenitor cells differentiated from multipotent stem cells. However, even if a cell sample contains such mature pancreatic cells, whether the Neph3-positive cells are pancreatic progenitor cells or mature pancreatic cells can be tested by using other pancreatic progenitor cell markers and/or mature pancreatic cell markers. The methods of the present invention for detecting pancreatic progenitor cells also relate to methods that additionally comprise the step of detecting or selecting (or removing) mature pancreatic cells from cell samples. The present invention also relates to methods that additionally comprise the step of detecting a pancreatic progenitor cell marker other than Neph3. Meanwhile, even if a cell sample contains mature pancreatic cells at a low percentage, pancreatic progenitor cells can be detected or selected in a highly specific manner by the methods of the present invention when the sample contains a sufficient number of pancreatic progenitor cells. The preferable cell samples to be used in the methods of the present invention contain pancreatic progenitor cells at a higher percentage than mature pancreatic. More preferably, the cell samples contain pancreatic progenitor cells, for example, twice or more, more preferably three times or more, four times or more, five times or more, six times or more, seven times or more, eight times or more, nine times or more, ten times or more, 20 times or more, or 30 times or more of the number of mature pancreatic cells. The methods of the present invention are also methods for detecting (including identifying, isolating, collecting, selecting, and enriching) cell groups (cell populations) that significantly contain pancreatic progenitor cells.

Various methods for detecting gene expression are known to those skilled in the art. Such method can be suitably used to detect the expression. The methods include, for example, methods for detecting gene transcripts, methods for detecting translated products of genes, and methods for detecting gene promoter activity (transcription activity). Specifically, detection of gene expression can be achieved by using reagents (probes, primers, antibodies, etc.) that specifically detect the transcript or translated product of a gene of interest or by using a reporter gene linked under the promoter regulation of the gene. Such reporter genes are not particularly limited. For example, it is possible to use a desired heterologous gene (specifically, a gene other than Neph3 that is linked to the promoter in the natural state). Such genes include, for example, those commonly used as a reporter gene, such as GFP and luciferase genes. Herein, the expression of a gene transcript may be transcription of the gene, while expression of the translated product of a gene may be translation of the gene transcript. Specifically, discrimination, detection, and/or identification of the expression of a gene transcript may be the discrimination, detection, and/or identification of transcription of the gene, respectively, and discrimination, detection, and/or identification of the expression of a gene translated product may be the discrimination, detection, and/or identification of the translated product of the gene, respectively. The detection of a gene transcript can be achieved, for example, by directly or indirectly detecting the transcript (mRNA) of the gene. For example, Northern blot analysis or in situ hybridization is useful for directly detecting the mRNA of interest in a cell sample. Alternatively, methods such as RT-PCR enable detection of the corresponding cDNA of the mRNA of interest after cDNA is synthesized from mRNA. Gene translated products can be detected by using antibodies, ligands, or the like, which bind to the translated products (proteins). The detection can be achieved, for example, by immunoprecipitation, pull-down assay, Western blotting, flow cytometry, or the like (Sambrook and Russell, Molecular Cloning, 3rd ed., Cold Spring Harbor Laboratory Press, Cold Spring Harbor, N.Y., USA, 2001).

(Probes/Primers)

More specifically, for example, the transcripts or their cDNA can be detected using reagents that specifically detect transcripts of the Neph3 gene of the present invention or their complementary strands. Such reagents include, for example, polynucleotides that specifically hybridize to the transcripts or complementary strands thereof. The length of polynucleotides is not particularly limited, as long as they can detect Neph3 transcripts. The polynucleotides may be short polypeptides (i.e., so-called "oligonucleotides"). Long polynucleotides can be used, for example, as a probe or such, while short polynucleotides can be used not only as probes but also as primers for RT-PCR or such, DNA chips, or the like. In general, polynucleotides for detecting the transcripts comprise at least 15 consecutive nucleotides of the sequence of a Neph3 gene transcript or the complementary sequence thereof, preferably at least 16, 17, 18, 19, 20, 22, 25, 27, 30, 35, 40, or 50 consecutive nucleotides. Such polynucleotides are useful as primers or probes for detecting pancreatic progenitor cells. When the polynucleotides are used as primers, their length is typically 200 nucleotides or less, preferably 150 nucleotides or less, 100 nucleotides or less, 80 nucleotides or less, 60 nucleotides or less, or 50 nucleotides or less. When the polynucleotides are used as probes, their length is typically 5,000 nucleotides or less, preferably 4,000 nucleotides or less, 3,000 nucleotides or less, 2,000 nucleotides or less, 1,000 nucleotides or less, or 800 nucleotides or less.

More specifically, when used as probes, the polynucleotides typically contain 15 to 1,000 nucleotides, preferably 25 to 500 nucleotides. Furthermore, the polynucleotides are used after they are appropriately labeled with radioisotopes, non-radioactive compounds, or the like When used as primers, the polynucleotides desirably consist of at least 15, preferably 20, 22, 25, or 30 nucleotides. When used as a primer, such polynucleotide can be designed in a form such that a sequence complementary to its target sequence is placed in the 3'-end region and restriction site sequences, tags, and the like are added in the 5'-end region. Such polynucleotides can be used to detect not only the expression of the Neph3 gene but also mutations in the Neph3 gene. The mutations potentially cause abnormalities in the regulation of pancreatic cell differentiation. Thus, the polynucleotides are expected to be useful for diagnosis of pancreatic disease or the like.

The above-described polynucleotides hybridize to Neph3 transcripts or cDNAs thereof (specifically, the complementary strands). It is preferable that they specifically hybridize to the Neph3 transcripts or cDNAs thereof (complementary strand). "Specifically hybridize" means a significantly strong hybridization to Neph3 transcripts or cDNAs thereof as compared to other sequences. For example, a probe comprising a nucleotide sequence complementary to a Neph3 transcript (i.e., antisense probe), and a probe comprising a complementary strand thereof (i.e., sense probe; control) are hybridized to mRNA, tissue sections, or the like prepared from cell samples containing pancreatic progenitor cells. The specificity can be confirmed if a significantly stronger signal is detected with the antisense probe as compared to the sense probe.

Unlike genomic DNA hybridization, it is believed that an extremely high specificity is not required because the types of mRNAs in a cell sample are typically limited. Alternatively, when detection is carried out by combining two or more primers or oligonucleotides such as in PCR, even if the specificity of individual oligonucleotides is low, it is possible to exert sufficient specificity by combining oligonucleotides. Designing primers to appropriately amplify a nucleic acid of interest is routinely carried out by those skilled in the art. The present invention also relates to primer sets consisting of two or more polynucleotides (for example, sets consisting of one or more primer pairs) for detecting Neph3 transcripts (for example, polynucleotides that hybridize to Neph3 transcripts or complementary strands thereof).

Polynucleotides for detecting Neph3 transcripts comprise a sequence complementary to Neph3 transcript or a complementary sequence thereof. Of the sequence, at least 15, 18, 20, 22, 25, 28, or 30 consecutive nucleotides may be completely complementary, or at least 70%, preferably 80%, more preferably 90%, and still more preferably 95% or more (for example, 97% or 99%) of the nucleotides may be completely complementary. "Completely complementary" means that a sequence is formed in which T (U in RNA), A, G, and C correspond to A, T or U, C, and G, respectively, in a nucleotide sequence.

The methods for detecting pancreatic progenitor cells, which are based on detection of a Neph3 gene transcript, comprise, for example, the steps of:

(a) incubating mRNA derived from a test cell sample or cDNA prepared from the mRNA with a polynucleotide that specifically hybridizes to the Neph3 gene transcript or a complementary strand thereof; and (b) detecting hybridization between the mRNA or cDNA and the polynucleotide.

Herein, when mRNA prepared from a cell sample is detected, incubation may be carried out using a polynucleotide that hybridizes to a Neph3 gene transcript. Alternatively, when a strand complementary to mRNA (the first strand of cDNA, etc.) is detected, incubation may be carried out using a polynucleotide that hybridizes to a sequence complementary to the Neph3 gene transcript. Alternatively, when a double-stranded cDNA or the like prepared from mRNA is used, incubation may be carried out using a polynucleotide that hybridizes to the Neph3 gene transcript and/or complementary strand thereof. Such hybridization can be detected by various nucleic acid detection methods using polynucleotides as a probe or primer. A typical method is the conventional hybridization method which uses polynucleotides as a probe. Hybridization can be achieved under the conditions described herein. Polynucleotides that specifically hybridize can be detected under such conditions. Polynucleotides may be appropriately labeled. Specifically, it is possible to use probes labeled with a radioisotope or non-radioactive compound. The radioisotopes to be used as a label include, for example, $^{32}P$, $^{35}S$, and $^{3}H$. When a radiolabeled polynucleotide probe is used, RNA that binds to a probe can be detected by detecting silver particles by emulsion autoradiography. Meanwhile, conventional non-radioisotopic compounds that are used to label polynucleotide probes are known, and include biotin and digoxigenin. The detection of biotin-labeled markers can be achieved, for example, using fluorescent-labeled avidin or avidin labeled with an enzyme such as alkaline phosphatase or horseradish peroxidase. On the other hand, the detection of digoxigenin-labeled markers can be achieved by using fluorescent-labeled anti-digoxigenin antibody or anti-digoxigenin antibody labeled with an enzyme such as alkaline phosphatase or horseradish peroxidase. When enzyme labeling is used, the detection can be made by allowing stable dye to deposit at marker positions by incubation with an enzyme substrate. When the polynucleotide hybridizes to a target nucleic acid, the cells from which the nucleic acid is derived are suggested to be pancreatic progenitor cells.

Nucleic acids can also be detected via gene amplification using the above-described polynucleotides as a primer. The above-described methods of the present invention comprise, for example, the steps of:

(a) performing gene amplification using mRNA derived from a test cell sample or cDNA prepared from the mRNA as a template and polynucleotides that specifically hybridize to the Neph3 gene transcript or a complementary strand thereof as primers; and (b) detecting the amplified product.

Gene amplification can be achieved using known methods, for example, polymerase chain reaction (PCR) or the like using a thermostable polymerase. For example, mRNA in a cell sample can be indirectly detected by RT-PCR, in which cDNA is synthesized from mRNA prepared from the cell sample by reverse transcription, and PCR is carried out using the synthesized cDNA. The amplified product generated by gene amplification can be detected by known methods. Meanwhile, a primer pair to be used in the amplification may be designed so that both the sense and antisense primers are placed within the region of Neph3 gene sequence. Alternatively, when the template cDNA is inserted into a vector or the like, either sense or antisense primer is designed to be placed within the Neph3 gene sequence and the other may be placed within the vector sequence.

In the present invention, polynucleotides for specifically detecting Neph3 transcript preferably hybridize to a Neph3 transcript or a complementary strand thereof at 42° C., for example, in an aqueous solution of a salt concentration (for example, the concentration of monocation such as $Na^{+}$) of 150 mM or lower (for example, a buffer (pH 7.0) containing 50 to 150 mM NaCl and may additionally contain appropriate divalent salts, reducing agents, proteins, sugars, etc.). More preferably, the polynucleotides hybridize at 45, 48, 50, 52, or 55° C. Whether the polynucleotides hybridize or not can be tested, for example, as follows. A membrane immobilized with a Neph3 transcript or complementary strand thereof is incubated with a labeled polynucleotide for hybridization; and the membrane is examined to assess whether it retains the label after being washed under the conditions described above (for example, in 1×SSC). Alternatively, the state of annealing and dissociation of nucleic acids can be determined by measuring absorbance at various temperatures after hybridization in an aqueous solution. Alternatively, amplification is carried out at an annealing temperature described above using the Neph3 transcript or a complementary strand thereof as a template and polynucleotides of interest as primers. Then, hybridization can be assessed by testing whether the expected PCR product is amplified. It is understood that the primers hybridize to the template when the desired product is amplified, because the desired PCR product is not amplified when the primers do not hybridize to the template.

As described above, polynucleotides that specifically hybridize to the Neph3 gene transcript or a complementary strand thereof are useful in detecting pancreatic progenitor cells (for example, multipotent pancreatic progenitor cells). The present invention provides the use of polynucleotides that specifically hybridize to the Neph3 gene transcript or a complementary strand thereof for detecting, distinguishing, identifying, selecting, preparing, enriching, collecting, isolating, and/or obtaining pancreatic progenitor cells. The present invention also provides reagents for detecting, distinguishing, identifying, selecting, preparing, enriching, collecting, isolating, and/or obtaining pancreatic progenitor cells, which comprise polynucleotides that specifically hybridize to the Neph3 gene transcript or cDNA thereof. In addition, the present invention provides kits and packages for detecting, distinguishing, identifying, selecting, preparing, enriching, collecting, isolating, and/or obtaining pancreatic progenitor cells, which comprise polynucleotides that specifically hybridize to the Neph3 gene transcript or cDNA thereof. The present invention also provides compositions for detecting, selecting, and such (detecting, distinguishing, identifying, selecting, preparing, enriching, collecting, isolating, and/or obtaining) pancreatic progenitor cells, which comprise polynucleotides that specifically hybridize to the Neph3 gene transcript or cDNA thereof. The compositions may comprise desired pharmaceutically acceptable carriers, specifically, for example, salts, sugars, proteins, pH buffers, and water. Polynucleotides for detecting Neph3 transcript can be used in a form of powder or solution as a reagent for detecting, distinguishing, identifying, selecting, preparing, enriching, collecting, isolating, and/or obtaining pancreatic progenitor cells.

In general, a nucleic acid and a polynucleotide refer to a polymer consisting of a number of nucleotides or nucleotide pairs such as of deoxyribonucleic acid (DNA) and/or ribonucleic acids (RNA). Such nucleic acid or polynucleotide may be constituted by natural bases, or may contain modified or artificial bases. If needed, nucleic acids or polynucleotides can also contain, for example, non-naturally occurring nucleotides such as 4-acetylcytidine, 5-(carboxyhydroxymethyl) uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methyl guano sine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N6-isopentenyladenosine, N-((9-β-D-ribofuranosyl-2-methylthiopurin-6-yl)carbamoyl)threonine, N-((9-β-D-ribofuranosylpurin-6-yl)N-methylcarbamoyl)threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9β-D-ribofuranosylpurin-6-yl)carbamoyl)threonine, 2'-O-methyl-5-methyluridine, 2'-O-methyluridine, wybutosine, and 3-(3-amino-3-carboxy propyl) uridine.

(Antibody)

Furthermore, expression of the Neph3 gene can be detected through detection of a translated product of the gene. For this purpose, for example, the Neph3 protein expression can be detected by detecting the Neph3 protein, or indirectly detected by detecting the activity of Neph3 protein or phenotypic alterations induced by the Neph3 protein. Typically, the step of detecting a Neph3 protein can be achieved by immunochemical methods, for example, using antibodies that bind to the Neph3 protein.

A translated product of the Neph3 gene can be detected, for example, by methods comprising the steps of:

(a) contacting a test cell sample with an antibody that binds to the Neph3 protein; and (b) detecting the binding between a test cell sample and the antibody.

The Neph3 protein expression can be detected, for example, by contacting an antibody that binds to the Neph3 protein with a cell sample that is expected to contain pancreatic progenitor cells, and detecting reactivity. Such cell samples may be intact cells, cell homogenates, or cell extracts. Antibodies may be immobilized onto an appropriate carrier before contacting the cells. Alternatively, cells bound to the antibody can be selectively collected via affinity purification of the antibody after cells are contacted and bound with the antibody. For example, a biotin-linked antibody can be purified by addition to plates or columns immobilized with avidin or streptavidin.

In addition to natural antibodies and fragments thereof (antigen-binding fragments), the antibodies of the present invention include various polypeptides such as those derived from antigen-binding domains of antibodies, and include, for example, polyclonal antibodies, monoclonal antibodies, chimeric antibodies, single-chain antibodies (scFV) (Huston et al., Proc. Natl. Acad. Sci. USA 1988, 85: 5879-83; The Pharmacology of Monoclonal Antibody, vol. 113, Rosenburg and Moore ed., Springer Verlag (1994) pp. 269-315), human antibodies, multispecific antibodies (LeDoussal et al., Int. J. Cancer Suppl. (1992) 7: 58-62; Paulus. Behring Inst. Mitt. (1985) 78: 118-32; Millstein and Cuello. Nature (1983) 305: 537-9; Zimmermann Rev. Physiol. Biochem. Pharmacol. (1986) 105: 176-260; Van Dijk et al. Int. J. Cancer (1989) 43: 944-9), and antibody fragments such as Fab, Fab', F(ab')2, Fc, and Fv. Moreover, antibodies may also be modified by PEG and such, as necessary. In the present invention, an antibody may also be produced in the form of a fusion protein with β-galactosidase, maltose-binding protein, GST, green fluorescent protein (GFP), or such, to allow detection without the use of a secondary antibody. In addition, an antibody may be modified by labeling with biotin or such to allow recovery using avidin, streptoavidin, etc.

An antibody that binds to Neph3 can be produced using a Neph3 protein, a fragment thereof, or a cell in which the Neph3 protein or fragment thereof is expressed, as a sensitized antigen. In addition, a short Neph3 polypeptide or a short fragment thereof used as an antigen may also be used as an immunogen by coupling to a carrier such as bovine serum albumin, Keyhole Limpet Hemocyanin, and ovalbumin. In addition, a polypeptide antigen or a fragment thereof may be used in combination with a known adjuvant such as aluminum adjuvant, Freund's complete (or incomplete) adjuvant, or pertussis adjuvant, to enhance the immune response to an antigen.

Polyclonal antibodies can be obtained from, for example, the serum of an immunized animal after immunizing a mammal with a Neph3 protein or a fragment thereof, together with an adjuvant as necessary. Although there are no particular limitations on the mammals used, typical examples include rodents, lagomorphs, and primates. Specific examples include rodents such as mice, rats, guinea pigs, and hamsters; lagomorphs such as rabbits; artiodactyls such as pigs, cows, goats, and sheep; perissodactyls such as horses; order carnivora such as dogs and cats; and primates such as monkeys including cynomolgus monkeys, rhesus monkeys, baboons, and chimpanzees. Animal immunization is carried out by suitably diluting and suspending a sensitized antigen in phosphate-buffered saline (PBS) or physiological saline, mixing with an adjuvant as necessary until emulsified, and injecting into an animal intraperitoneally or subcutaneously. The sensitized antigen mixed with Freund's incomplete adjuvant is preferably administered several times, every 4 to 21 days. Antibody production can be confirmed by measuring the level of an antibody of interest in the serum using conventional methods. Finally, the serum itself may be used as a polyclonal antibody, or it may be further purified. See, for example, "Current Protocols in Molecular Biology" (John Wiley & Sons (1987), Sections 11.12-11.13), for specific methods.

A monoclonal antibody can be produced by removing the spleen from an animal immunized in the manner described above, isolating immunocytes from the spleen, and fusing with a suitable myeloma cell using polyethylene glycol (PEG) or such to establish hybridomas. Cell fusion can be carried out according to the Milstein method (Galfre and Milstein. Methods Enzymol. (1981) 73: 3-46). Here, suitable myeloma cells are exemplified particularly by cells that allow chemical selection of fused cells. When using such myeloma cells, fused hybridomas are selected by culturing in a culture medium (HAT culture medium) that contains hypoxanthine, aminopterin, and thymidine, which destroy cells other than the fused cells. Next, a clone that produces an antibody that binds to an antigen protein or a fragment thereof is selected from the established hybridomas. Subsequently, the selected clone is introduced into the abdominal cavity of a mouse or such, and ascites is collected to obtain a monoclonal antibody. See, in addition, "Current Protocols in Molecular Biology" (John Wiley & Sons (1987), Sections 11.4-11.11) for information on specific methods.

Hybridomas can also be obtained by first sensitizing human lymphocytes that have been infected by EB virus with an immunogen in vitro, and fusing the sensitized lymphocytes with human myeloma cells (such as U266) to obtain hybridomas that produce human antibodies (Japanese Patent Application Kokai Publication No. (JP-A) S63-17688 (unexamined, published Japanese patent application)). In addition, human antibodies can also be obtained by using antibody-producing cells generated by sensitizing a transgenic animal with a human antibody gene repertoire (WO 92/03918; WO 93/02227; WO 94/02602; WO 94/25585; WO 96/33735; WO 96/34096; Mendez et al. Nat. Genet. (1997) 15: 146-156, etc.). Methods that do not use hybridomas can be exemplified by a method in which a cancer gene is introduced to immortalize immunocytes such as antibody-producing lymphocytes.

In addition, antibodies can also be produced by genetic recombination techniques (see Borrebaeck and Larrick (1990) Therapeutic Monoclonal Antibodies, MacMillan Publishers Ltd., UK). First, a gene that encodes an antibody is cloned from hybridomas or antibody-producing cells (such as sensitized lymphocytes). The resulting gene is then inserted into a suitable vector, the vector is introduced into a host, and the host is then cultured to produce the antibody. This type of recombinant antibody is also included in the antibodies herein. Typical examples of recombinant antibodies include chimeric antibodies comprising a non-human antibody-derived variable region and a human antibody-derived constant region, and humanized antibodies comprising a non-human-derived antibody complementarity determining region (CDR), human antibody-derived framework region (FR), and human antibody constant region (Jones et al. Nature (1986) 321:522-5; Reichmann et al. Nature (1988) 332: 323-9; Presta. Curr. Op. Struct. Biol. (1992) 2: 593-6; Methods Enzymol. (1991) 203: 99-121).

Antibody fragments can be produced by treating the aforementioned polyclonal or monoclonal antibodies with enzymes such as papain or pepsin. Alternatively, an antibody fragment can be produced by genetic engineering techniques using a gene that encodes an antibody fragment (see Co et al., J. Immunol. (1994) 152: 2968-76; Better and Horwitz. Methods Enzymol. (1989) 178: 476-96; Pluckthun and Skerra. Methods Enzymol. (1989) 178: 497-515; Lamoyi. Methods Enzymol. (1986) 121: 652-63; Rousseaux et al., (1986) 121: 663-9; Bird and Walker. Trends Biotechnol. (1991) 9: 132-7).

The multispecific antibodies include bispecific antibodies (BsAb), diabodies (Db), etc. Multispecific antibodies can be produced by methods such as (1) chemically coupling antibodies having different specificities with different types of bifunctional linkers (Paulus Behring Inst. Mill. (1985) 78: 118-32), (2) fusing hybridomas that secrete different monoclonal antibodies (Millstein and Cuello. Nature (1983) 305: 537-9), or (3) transfecting eukaryotic cell expression systems, such as mouse myeloma cells, with a light chain gene and a heavy chain gene of different monoclonal antibodies (four types of DNA), followed by the isolation of a bispecific monovalent portion (Zimmermann. Rev. Physio. Biochem. Pharmacol. (1986) 105: 176-260; Van Dijk et al., Int. J. Cancer (1989) 43: 944-9). On the other hand, diabodies are dimer antibody fragments consisting of two bivalent polypeptide chains that can be constructed by gene fusion. They can be produced using known methods (see Holliger et al., Proc. Natl. Acad. Sci. USA (1993) 90: 6444-8; EP404097; WO 93/11161).

Recovery and purification of antibodies and antibody fragments can be carried out using Protein A and Protein G, or according to known protein purification techniques (Antibodies: A Laboratory Manual, Ed. Harlow and David Lane, Cold Spring Harbor Laboratory (1988)). For example, when using Protein A to purify an antibody, known Protein A columns such as Hyper D, POROS, or Sepharose F. F. (Pharmacia) can be used. The concentration of the resulting antibody can be determined by measuring the absorbance or by enzyme linked immunoadsorbent assay (ELISA).

Antigen-binding activity of an antibody can be determined by absorbance measurement, or by using fluorescent antibody methods, enzyme immunoassay (EIA) methods, radioimmunoassay (RIA) methods, or ELISA. When ELISA is used, an antibody that binds to Neph3 proteins is first immobilized onto a carrier such as a plate. Neph3 proteins or fragments thereof are added, and then a sample containing the antibody of interest is added. Here, samples containing an antibody of interest include culture supernatants of antibody-producing cells, purified antibodies, etc. Next, a secondary antibody that recognizes the antibody is added, followed by the incubation of the plate. Subsequently, the plate is washed and the label attached to the secondary antibody is detected. Namely, if a secondary antibody is labeled with alkaline phosphatase, the antigen binding activity can be determined by adding an enzyme substrate such as p-nitrophenyl phosphate, and measuring the absorbance. In addition, a commercially available system such as BIAcore (Pharmacia) can also be used to evaluate antibody activities.

The obtained antibodies can recognize or detect a Neph3 protein or fragments thereof. Furthermore, since the antibodies recognize a Neph3 protein or fragments thereof, they can recognize or detect cells or the like expressing the protein or fragments thereof. The antibodies can also be used to purify a Neph3 protein or fragments thereof. In addition, the antibodies can be used to purify cells and the like expressing a Neph3 protein or fragments thereof.

Antibodies that bind to an extracellular domain of a Neph3 protein are particularly useful, because they enable detection, isolation, and separation of viable cells expressing the Neph3 protein without using the translated product and transcript of any foreign gene. Such antibodies can be obtained, for example, by selecting from antibodies that bind to a Neph3 protein using an extracellular domain of the Neph3 protein or a fragment thereof. Alternatively, antibodies may be produced by using as an antigen an extracellular domain of the Neph3 protein or a fragment thereof. Antibodies can also be produced via immunization with cells expressing the Neph3 protein, homogenate thereof (membrane fraction), or the like. The extracellular domain of the Neph3 protein can be easily checked by using the PSORT program or such, and corresponds to specifically the amino acid sequence of positions 21 to 510 in the amino acid sequence of SEQ ID NO: 2, 4, 10, 12, 14, or 16; positions 20 to 513 in the amino acid sequence of SEQ ID NO: 6 or 8; positions 21 to 460 in the amino acid sequence of SEQ ID NO: 18 or 20; or positions 21 to 490 in the amino acid sequence of SEQ ID NO: 22. Such antibodies may be those, for example, against a polypeptide consisting of the whole extracellular domain or at least six consecutive amino acids, preferably seven or more amino acids, eight or more amino acids, nine or more amino acids, ten or more amino acids, 12 or more amino acids, 15 or more amino acids, or 17 or more amino acids in an above-described amino acid sequence.

The amino acid sequences of the obtained antibodies may be suitably altered to enhance antibody stability or antigen affinity. The amino acid sequences can be altered, for example, by known methods such as site-directed mutagenesis (see "Molecular Cloning, A Laboratory Manual 2$^{nd}$ ed." (Cold Spring Harbor Press (1989)), "Current Protocols in Molecular Biology" (John Wiley & Sons (1987-1997); particularly, Section 8.1-8.5), Hashimoto-Goto et al. (1995) Gene 152: 271-5, Kunkel (1985) Proc. Natl. Acad. Sci. USA 82: 488-92; Kramer and Fritz (1987) Method. Enzymol. 154: 350-67; Kunkel (1988) Method. Enzymol. 85: 2763-6; or such). Such alteration includes one or more amino acid substitution, deletion, and/or addition. Herein, substitution includes amino acid substitutions with an amino acid having similar properties (conservative substitutions). Amino acids can be classified, based on their properties, into non-polar amino acids (Ala, Ile, Leu, Met, Phe, Pro, Trp, Val), non-charged amino acids (Asn, Cys, Gln, Gly, Ser, Thr, Tyr), acidic amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxyamino acids (Ser, Thr), amide-type amino acids (Gln, Asn), sulfur-containing amino acids (Cys, Met), aromatic amino acids (His, Phe, Trp, Tyr), heterocyclic amino acids (His, Trp), imino acids (Pro, 4Hyp), etc. Amino acid substitutions within the groups are conservative substitutions. In particular, substitutions among Ala, Val, Leu, and Ile; Ser and Thr; Asp and Glu; Asn and Gln; Lys and Arg; and Phe and Tyr are likely to maintain protein properties. There are no particular limitations on the number and sites of the mutated amino acids, as long as the substituted antibody binds to Neph3 protein.

Amino acid residues that constitute polypeptide chains of an antibody may be naturally occurring or modified amino acid residues. Such modifications include, for example, modifications by phosphate groups, sialic acids, sugar chains, and such. Examples of amino acid residue modifications include acylation, acetylation, amidation, arginylation, GPI anchor formation, crosslinking, γ-carboxylation, cyclization, covalent crosslink formation, glycosylation, oxidation, covalent bonding of a lipid or fat derivative, cystine formation, disulfide bond formation, selenoylation, demethylation, protein fragmentation treatment, covalent bonding of a nucleotide or nucleotide derivative, hydroxylation, pyroglutamate formation, covalent bonding of a flavin, prenylation, covalent bonding with a heme portion, covalent bonding of phosphatidyl inositol, formylation, myristoylation, methylation, ubiquitination, iodination, racemization, ADP-ribosylation, sulfation, and phosphorylation. Moreover, the polypeptides include precursors containing a signal peptide portion, mature forms lacking a signal peptide portion, and fusion proteins modified with other peptide sequences. Peptide sequences to be added to a polypeptide include influenza agglutinin (HA), glutathione S transferase (GST), substance P, multiple histidine tag (such as 6×His and 10×His), protein C fragment, maltose-binding protein (MBP), immunoglobulin constant region, α-tubulin fragment, β-galactosidase, B-tag, c-myc fragment, E-tag (epitope on a monoclonal phage), FLAG (Hopp et al., Bio/Technol. (1988) δ: 1204-10), lck tag, p18 HIV fragment, HSV-tag (human simple Herpes virus glycoprotein), SV40T antigen fragment, T7-tag (T7 gene 10 protein), and VSV-GP fragment (vesicular stomatitis virus glycoprotein).

Antibodies that bind to the Neph3 protein can be used as an agent for detecting (distinguishing, identifying, selecting, preparing, enriching, collecting, isolating, and/or obtaining) pancreatic progenitor cells (for example, multipotent pancreatic progenitor cells). More specifically, pancreatic progenitor cells can be detected (distinguished, identified, selected, prepared, enriched, collected, isolated, and/or obtained) by detecting the expression of the Neph3 gene in a cell sample. The present invention provides the use of antibodies that bind to a translated product of the Neph3 gene in detecting, distinguishing, identifying, selecting, preparing, enriching, collecting, isolating, and/or obtaining pancreatic progenitor cells. The present invention also provides reagents for detecting, distinguishing, identifying, selecting, preparing, enriching, collecting, isolating, and/or obtaining pancreatic progenitor cells, which comprise an antibody that binds to a translated product of the Neph3 gene. The present invention also provides kits and packages for detecting, distinguishing, identifying, selecting, preparing, enriching, collecting, isolating, and/or obtaining pancreatic progenitor cells, which comprise an antibody that binds to the translated product of the Neph3 gene. The present invention also provides compositions for detecting, distinguishing, identifying, selecting, preparing, enriching, collecting, isolating, and/or obtaining pancreatic progenitor cells, which comprise an antibody that binds to a translated product of the Neph3 gene. The compositions may comprise a desired pharmaceutically acceptable carrier, specifically for example, salts, sugars, proteins, pH buffers, and water.

Meanwhile, antibodies that bind to the Neph3 protein may be linked to a carrier. For example, cells expressing Neph3 can be easily isolated by using antibody-immobilized beads. It is preferred that carriers to be used for antibody immobilization are non-cytotoxic, and include, for example, synthetic or naturally-occurring organic polymer compounds, inorganic materials such as glass beads, silica gel, alumina, magnetic substances, and activated charcoal, and those surface-coated with a polysaccharide, synthetic polymer, or the like. The form of the carrier is not particularly limited; however, the form includes, for example, films, fibers, granules, hollow fibers, non-woven fabric, porous carriers, and honeycombed carriers, and the contact surface area can be controlled by altering their thickness, surface area, width, length, shape, and size in various ways.

(Promoter)

Alternatively, the expression of the Neph3 gene can be detected by detecting the promoter activity of the gene. Reporter constructs for detection can be prepared, for example, using the Neph3 gene promoter (including modified promoters) (see, for example, JP-A (Kokai) 2002-51775). Moreover, the Neph3 gene promoter may be partially deleted, or may be added or substituted with the whole or a portion of another promoter, as long as the resulting Neph3 gene promoter retains a transcription activity specific to pancreatic progenitor cells. For example, such reporter constructs are prepared by transfecting cells with a vector carrying a construct in which, for example, a gene encoding a detectable marker such as green fluorescent protein (GFP) is linked to a promoter portion identified by expression analysis of the Neph3 gene. Alternatively, the maker gene can be knocked-in at the Neph3 locus. In a preferred embodiment, the construct includes, for example, those described in the reference of WO 2008/096817 (panels 2 to 4 of FIG. 10). When promoter activation is detected in cells, they are suggested to be pancreatic progenitor cells. In this case, "the marker-encoding gene is linked to a promoter portion" means that the gene encoding a marker is linked in an expressible manner, and it may be directly linked to the promoter, or distantly linked to the promoter but is still under its control.

The Neph3 promoter/reporter constructs are useful as an agent for detecting (distinguishing, identifying, selecting, preparing, enriching, collecting, isolating, and/or obtaining) pancreatic progenitor cells (for example, multipotent pancreatic progenitor cells). More specifically, pancreatic progenitor cells can be detected (distinguished, identified, selected, prepared, enriched, collected, isolated, and/or obtained) using constructs for detecting Neph3 promoter activity. The present invention provides the use of nucleic acid constructs for detecting Neph3 promoter activity, in detecting, distinguishing, identifying, selecting, preparing, enriching, collecting, isolating, and/or obtaining pancreatic progenitor cells. The present invention also provides reagents for detecting, distinguishing, identifying, selecting, preparing, enriching, collecting, isolating, and/or obtaining pancreatic progenitor cells, which comprise nucleic acid constructs for detecting Neph3 promoter activity. In addition, the present invention also provides kits and packages for detecting, distinguishing, identifying, selecting, preparing, enriching, collecting, isolating, and/or obtaining pancreatic progenitor cells, which comprise nucleic acid constructs for detecting Neph3 promoter activity. The present invention further provides compositions for detecting, distinguishing, identifying, selecting, preparing, enriching, collecting, isolating, and/or obtaining pancreatic progenitor cells, which comprise nucleic acid constructs for detecting Neph3 promoter activity. The compositions may comprise a desired pharmaceutically acceptable carrier, specifically for example, salts, sugars, proteins, pH buffers, and water. The Neph3 promoter/reporter constructs may also be used to differentiate pancreatic progenitor cells into desired pancreatic cells (pancreatic α cells, pancreatic β cells, pancreatic δ cells, and/or PP cells, etc.). For example, pancreatic progenitor cells can be differentiated into pancreatic β cells by introducing and expressing a factor such as Ngn3 under the control of an expression regulatory sequence (including the promoter, enhancer, etc.) of the Neph3 gene.

More specifically, the Neph3 gene promoter is useful for expressing desired genes in pancreatic progenitor cells. A desired gene can be expressed in pancreatic progenitor cells, for example, by linking the desired gene (for example, a gene other than the Neph3 gene) under the control of the Neph3 gene promoter and providing pancreatic progenitor cells comprising the nucleic acid construct. Such pancreatic progenitor cells can be provided, for example, by introducing the nucleic acid construct into pancreatic progenitor cells, or by introducing the construct into primordial cells (for example, ES cells, iPS cells, embryos, etc.) capable of differentiating into pancreatic progenitor cells and then differentiating the cells into pancreatic progenitor cells. Since the promoter can specifically select pancreatic progenitor cells, it is not necessary to introduce the nucleic acid construct into only pancreatic progenitor cells. The promoter can express genes selectively in pancreatic progenitor cells even when introduced into cell populations containing pancreatic progenitor cells and other cells. Alternatively, the construct may be introduced into stem cells at a less-differentiated stage. The present invention provides use of the Neph3 gene promoter in expressing desired genes in pancreatic progenitor cells. The present invention also provides agents (expression reagents) for expressing desired genes in pancreatic progenitor cells, which comprise the Neph3 gene promoter. Furthermore, the present invention provides use of nucleic acids in which a desired heterologous gene (for example, a gene other than the Neph3 gene) is linked under the control of the Neph3 gene promoter, in expressing the gene in pancreatic progenitor cells. The present invention further relates to methods for expressing a heterologous gene in pancreatic progenitor cells, which comprise the step of preparing the pancreatic progenitor cells comprising a nucleic acid in which the heterologous gene is linked under the control of the Nephrin-like 3 (Neph3) gene promoter. As described below, pancreatic progenitor cells comprising a nucleic acid in which a reporter gene is linked under the control of the Neph3 gene promoter are useful in assaying or screening for substances that are effective for inducing or regulating the differentiation of pancreatic progenitor cells.

The Neph3 gene promoter can be isolated, for example, by PCR, screening of genomic libraries, or the like, using a nucleic acid of the Neph3 coding region as a primer or probe. As described in the Examples, the 2-kb fragment adjacent to the 5'-end of the Neph3 gene transcribed region exhibits sufficient promoter activity in pancreatic progenitor cells. Thus, the fragments of 5 kb, 4 kb, 3 kb, and 2 kb adjacent to the 5' end of the Neph3 gene transcribed region can be preferably used as a Neph3 gene promoter of the present invention. By suitably deleting the fragments, those skilled in the art can obtain shorter fragments (for example, fragments of 500 bp or more, or 1 kb or more) that retain the promoter activity in pancreatic progenitor cells. Such fragments can also be used as a Neph3 gene promoter of the present invention.

More specifically, the present invention also relates to:

[1] a reagent for distinguishing, detecting, identifying, collecting, isolating, and/or obtaining pancreatic progenitor cells, which comprises any one of (a) to (c) below to detect the Nephrin-like 3 (Neph3) gene expression, and use of (a) to (c) below in distinguishing, detecting, identifying, collecting, isolating, and/or obtaining pancreatic progenitor cells;

(a) an antibody that specifically binds to a translated product of the gene;

(b) a nucleic acid that specifically hybridizes to the transcript of the gene; and (c) a nucleic acid in which a heterologous gene is linked under the control of the gene promoter;

[2] a reagent for expressing a gene in pancreatic progenitor cells, which comprises the Nephrin-like 3 (Neph3) gene promoter, and use of the Nephrin-like 3 (Neph3) gene promoter in expressing the gene in pancreatic progenitor cells; and

[3] a method for expressing a heterologous gene in pancreatic progenitor cells, which comprises the step of providing pancreatic progenitor cells comprising a nucleic acid in which the heterologous gene is linked under the promoter of the Nephrin-like 3 (Neph3) gene.

(Production Method)

The methods of the present invention for detecting (including the meaning of distinguishing, identifying, collecting, preparing, selecting, enriching, isolating, and/or obtaining) pancreatic progenitor cells comprise a desired process including the step of identifying pancreatic progenitor cells through detection of the expression of a translated product and/or transcript of the Neph3 gene. The methods of the present invention for detecting pancreatic progenitor cells include, for example, methods for detecting, distinguishing, identifying, collecting, preparing, selecting, enriching, isolating, and/or obtaining pancreatic progenitor cells, which comprise detecting, distinguishing, identifying, collecting, preparing, selecting, enriching, isolating, and/or obtaining cells expressing Neph3 through detection of the expression of a translated product and/or transcript of the Neph3 gene in cells. The present invention also relates to methods for producing cell populations containing pancreatic progenitor cells (or fractions comprising pancreatic progenitor cells, or compositions comprising pancreatic progenitor cells), which comprise the steps of:

performing detection, identification, and/or selection, or the like of the expression of a translated product and/or transcript of the Neph3 gene in a cell sample containing pancreatic progenitor cells; and performing selection, isolation, and/or collection, or the like of cells expressing the gene. The cell selection, isolation, collection, or the like can be efficiently achieved, for example, by flow cytometry using antibodies that bind to the Neph3 protein. Fractions of enriched pancreatic progenitor cells can be obtained by the methods of the present invention for preparing cell population containing pancreatic progenitor cells. The obtained cells can be used to elucidate the mechanism for pancreatic differentiation or to treat diseases caused by abnormal pancreatic function.

(Combination with Other Markers)

The methods of the present invention for producing cell populations comprising pancreatic progenitor cells and methods of the present invention for detecting (including the meaning of distinguishing, identifying, selecting, preparing, enriching, collecting, isolating, and/or obtaining) pancreatic progenitor cells may additionally comprise the step of detecting (including the meaning of distinguishing, identifying, selecting, preparing, enriching, collecting, isolating, and/or obtaining) the expression of genes other than the Neph3 gene. For example, the methods of the present invention can additionally comprise the step of detecting (including the meaning of distinguishing, identifying, selecting, preparing, enriching, collecting, isolating, and/or obtaining) the expression of a transcript and/or translated product of pancreatic progenitor cell marker genes other than the Neph3 gene. Such pancreatic progenitor cell marker genes include, for example, pancreatic and duodenal homeobox factor-1 (Pdx-1), pancreas specific transcription factor-1a (Ptf1a), carboxypeptidase A1(pancreatic) (Cpa1), and epiplakin 1 (EPPK1). The methods of the present invention may comprise the step of detecting the expression of a transcript and/or translated product of one or more of pancreatic progenitor cell marker genes including those described above. Detection of the expression of transcripts and/or translated products of the genes may be performed before, after, or simultaneously at the time of detecting the expression of a transcript and/or translated product of the Neph3 gene. The expression of a number of genes can be simultaneously detected, for example, by using probes or antibodies labeled with different fluorescences. The methods of the present invention may additionally comprise, for example, the step of detecting the expression of transcripts and/or translated products of Pdx-1 and/or Ptf1a, and may further comprise, for example, the step of detecting the expression of a transcript and/or translated product of EPPK1, and may yet further comprise, for example, the step of detecting the expression of a transcript and/or translated product of the Cpa1 gene.

Such marker genes are specifically described herein as an example (see accession numbers and such exemplified herein). In addition to the sequences specifically exemplified, the Pdx-1, Ptf1a, Cpa1, and EPPK1 genes of the present invention also include isoforms, splicing variants, and allelic mutants thereof. Specifically, in the present invention, the Pdx-1, Ptf1a, Cpa1, and EPPK1 genes include the following polynucleotides:

(i) a polynucleotide comprising a coding sequence (CDS) of the nucleotide sequence of the Pdx-1, Ptf1a, Cpa1, or EPPK1 gene specified under the accession numbers exemplified herein;

(ii) a polynucleotide that is expressed in pancreatic progenitor cells and comprises a nucleotide sequence encoding the amino acid sequence of the Pdx-1, Ptf1a, Cpa1, or EPPK1 protein specified under the accession numbers exemplified herein;

(iii) a polynucleotide that is expressed in pancreatic progenitor cells and comprises a nucleotide sequence with one or more nucleotide insertions, substitutions, deletions, and/or additions (addition refers, for example, to adding one or more nucleotides to either or both of the ends of a nucleotide sequence) in the coding sequence of the nucleotide sequence of the Pdx-1, Ptf1a, Cpa1, or EPPK1 gene specified under the accession numbers exemplified herein;

(iv) a polynucleotide that is expressed in pancreatic progenitor cells and comprises a nucleotide sequence encoding an amino acid sequence with one or more amino acid insertions, substitutions, deletions, and/or additions (addition refers, for example, to adding one or more amino acids to either or both of the ends of an amino acid sequence) in the amino acid sequence encoded by the coding sequence of the nucleotide sequence of the Pdx-1, Ptf1a, Cpa1, or EPPK1 gene specified under the accession numbers exemplified herein;

(v) a polynucleotide that is expressed in pancreatic progenitor cells and hybridizes under stringent conditions to the complementary strand of a polynucleotide comprising the coding sequence of the nucleotide sequence of the Pdx-1, Ptf1a, Cpa1, or EPPK1 gene specified under the accession numbers exemplified herein;

(vi) a polynucleotide that is expressed in pancreatic progenitor cells and comprises a nucleotide sequence that has high sequence identity to the coding sequence of the nucleotide sequence of the Pdx-1, Ptf1a, Cpa1, or EPPK1 gene specified under the accession numbers exemplified herein; and (vii) a polynucleotide that is expressed in pancreatic progenitor cells and comprises a nucleotide sequence encoding an amino acid sequence that has high sequence identity to the amino acid sequence encoded by the coding sequence of the nucleotide sequence of the Pdx-1, Ptf1a, Cpa1, or EPPK1 gene specified under the accession numbers exemplified herein.

Meanwhile, in the present invention, the Pdx-1, Ptf1a, Cpa1, and EPPK1 proteins include polypeptides encoded by the respective genes described above, and specifically include the following polypeptides:

(i) a polypeptide comprising the amino acid sequence of the Pdx-1, Ptf1a, Cpa1, or EPPK1 protein specified under the accession numbers exemplified herein;

(ii) a polypeptide that is expressed in pancreatic progenitor cells and comprises an amino acid sequence with one or more amino acid insertions, substitutions, deletions, and/or additions (addition refers, for example, to adding one or more amino acids to either or both of the ends of an amino acid sequence) in the amino acid sequence of the Pdx-1, Ptf1a, Cpa1, or EPPK1 protein specified under the accession numbers exemplified herein;

(iii) a polypeptide that is expressed in pancreatic progenitor cells and encoded by a polynucleotide that hybridizes under stringent conditions to the complementary strand of a polynucleotide encoding the amino acid sequence of the Pdx-1, Ptf1a, Cpa1, or EPPK1 protein specified under the accession numbers exemplified herein; and (iv) a polypeptide that is expressed in pancreatic progenitor cells and comprises an amino acid sequence that has high sequence identity to the amino acid sequence of the Pdx-1, Ptf1a, Cpa1, or EPPK1 protein specified under the accession numbers exemplified herein.

Examples of the nucleotide sequences of the Pdx-1, Ptf1a, and Cpa1 genes are shown again below. Pdx-1 includes, for example, accession NM_000209.3 (coding sequence (CDS) 109-957), NM_008814.3 (CDS 109-960), XM_543155.2 (CDS 1-1596), XM_509600.2 (CDS 113-961), XM_583722.3 (CDS 1-855), and XM_001234635.1 (CDS 1-693); Ptf1a includes, for example, NM_178161.2 (CDS 1-984), NM_018809.1 (CDS 199-1170), NM_207641.2 (CDS 89-883), XM_001146416.1 (CDS 1-579), and NM_053964.1 (CDS 234-1211); Cpa1 includes, for example, NM_001868.1 (CDS 8-1264, sig_peptide 8-55, mat_peptide 56-1264), NM_174750.2 (CDS 27-1283, sig_peptide 27-74, mat_peptide 375-1283), NM_025350.3 (CDS 244-1500), XM_851827.1 (CDS 30-1313), NM_016998.2 (CDS 309-1565, sig_peptide 312-356, mat_peptide 639-1565), and NM_204584.1 (CDS 17-1273, sig_peptide 17-67, mat_peptide 353-1273). Meanwhile, the amino acid sequences of the Pdx-1, Ptf1a, and Cpa1 proteins include, for example, proteins encoded by the CDSs of each of the genes described above, and specifically include: NP_000200.1, NP_032840.1, XP_543155.2, XP_509600.2, XP_583722.1, and XP_001234636.1 for Pdx-1; NP 835455.1, NP_061279.1, NP 997524.1, XP_001146416.1, and NP_446416.1 for Ptf1a; NP_001859.1 (sig_peptide 1-16, mat_peptide 17-419), NP_777175.1 (sig_peptide 1-16, mat_peptide 117-419), NP_079626.2, and XP_856920.1 for Cpa1. EPPK1 includes, for example, nucleotide sequences and amino acid sequences shown in NM_031308.1 (CDS 14-15283), XM_372063 (CDS 1-7185); NM_144848.2 (CDS 1134-20777), NM_173025 (CDS 95-2305), XM_910512 (CDS 1-7725), NP_112598, XM_001074770 (CDS 1-10374), XP_001074770, XM_001059215 (CDS 1-10086), XP_001059215, NM_144848.2 (CDS 1134-20777), and NP_659097.

The specific details of hybridization conditions, alteration of multiple nucleotides or amino acids, high nucleotide or amino acid sequence identity, and others are the same as those described for the Neph3 herein. Polynucleotides that constitute the Pdx-1, Ptf1a, Cpa1, or EPPK1 gene can be appropriately produced by PCR, hybridization, chemical synthesis, or the like from cells expressing such genes. The nucleotide sequences of the obtained polynucleotides can be determined by conventional methods, for example, dideoxy nucleotide chain terminator method (Sanger et al., Proc. Natl. Acad. Sci. USA (1977) 74: 5463) or the like. Alternatively, it is possible to analyze the sequences using an appropriate DNA sequencer.

The methods of the present invention for detecting (including the meaning of distinguishing, identifying, selecting, preparing, enriching, collecting, isolating, and/or obtaining) pancreatic progenitor cells may additionally comprise, for example, the step of detecting the expression of translated products and/or transcripts of mature pancreatic cell marker genes. More specifically, cells that express translated products and/or transcripts of the genes can be distinguished from cells that do not express them by detecting the expression of translated products and/or transcripts of one or more genes specific to mature pancreatic cells. The purity of pancreatic progenitor cells can be increased by selecting cells that do not express the translated products and/or transcripts of mature pancreatic cell markers, or separating or removing cells that express them. The methods of the present invention for detecting (including the meaning of distinguishing, identifying, selecting, preparing, enriching, collecting, isolating, and/or obtaining) pancreatic progenitor cells may additionally comprise, for example, the step of detecting the expression of the translated products and/or transcripts of marker genes for dopamine-producing neuron progenitor cells and/or GABA-producing neuron progenitor cells. More specifically, cells that express genes specific to these neuron progenitor cells can be distinguished from cells that do not express the genes by detecting the expression of the translated product and/or transcript of one or more genes specific to these neuron progenitor cells. The purity of pancreatic progenitor cells can be increased by selecting cells that do not express the translated product and/or transcript of neuron progenitor cell markers, or by separating or removing cells that express them. Marker genes of dopamine-producing neuron progenitor cells include, for example, low density lipoprotein receptor-related protein 4 (Lrp4) gene (Nakayama, M. et al., Genome Res. (2002) 12(11): 1773-1784; Nakayama, M. et al., Genomics (1998) 51(1): 27-34; Accession NM_016869; XM_035037) and tyrosine hydroxylase. Marker genes of GABA-producing neuron progenitor cells include, for example, Corl1, paired box 2 (Pax2), Lim1/2, ladybird homeobox 1 (Lbx1), and Corl2 genes (Mizuhara E et al., J Biol. Chem. (2005) 280(5): 3645-55; Maricich S M et al., J Neurobiol. (1999) 41(2): 281-94; Moretti, P. et al., Gene (1994) 144(2): 213-219). Marker genes of neuron progenitor cells include, for example, Nestin and Sox1/2/3 genes. Similarly to detection of the Neph3 gene expression, the expression of these genes can be detected by detecting their transcripts and translated products, promoter activities, or the like (see WO 2004/038018 and WO 2008/096817).

Polynucleotides that specifically hybridize to the transcripts or cDNAs of the above-described marker genes, antibodies that bind to proteins encoded by the above-described marker genes, and such can be supplementary reagents for detecting pancreatic progenitor cells when used in combination with the reagents for detecting the Neph3 gene expression described herein. The present invention provides kits and packages for detecting pancreatic progenitor cells, which comprise reagents for detecting or such the Neph3 gene expression and reagents for detecting or such the expression of one or more of the above-described marker genes. In particular, polynucleotides and/or antibodies for detecting expression of the transcripts and/or translated products of an arbitrary combination of genes selected from the Pdx-1, Ptf1a, Cpa1, and EPPK1 genes are useful as additional reagents for detecting pancreatic progenitor cells in the present invention. Such reagents can be arbitrarily selected and combined from probes, primers, and primer sets comprising polynucleotides that can specifically hybridize to the transcript of each gene or a complementary strand thereof, and antibodies that bind to the translated product of each gene. These reagents can be formulated into compositions by appropriately combining them with a desired pharmaceutically acceptable carrier. The reagents may be mixed together or supplied in separate containers. In particular, kits and packages comprising antibodies that bind to each marker protein are useful as kits and packages for detecting, distinguishing, identifying, collecting, preparing, selecting, enriching, isolating, and/or obtaining, or the like pancreatic progenitor cells.

(Screening)

Furthermore, since the Neph3 gene is an indicator of pancreatic progenitor cells, substances effective for inducing or regulating the differentiation of pancreatic progenitor cells can be assayed or screened by detecting the expression of a translated product and/or transcript of the Neph3 gene. More specifically, the present invention relates to methods of assaying or screening for agents for regulating the differentiation of pancreatic progenitor cells. Compounds screened by the methods are candidate compounds for treating diseases caused by pancreas abnormal pancreatic function as they are expected to have the function of regulating pancreatic progenitor cell differentiation. Target diseases to be treated by the compounds obtained by the screening methods include, for example, diabetes.

In the present invention, the methods of assaying or screening for compounds that are capable of regulating the differentiation of pancreatic progenitor cells comprise, for example, the steps of:

(a) contacting a test sample with pancreatic progenitor cells or cells that can be differentiated into pancreatic progenitor cells; and (b) detecting the expression of a translated product and/or transcript of the Neph3 gene in the cells.

Compounds that induce or increase the expression of a translated product and/or transcript of the Neph3 gene are candidate compounds for inducing the differentiation of pancreatic progenitor cells. Meanwhile, compounds that decrease or suppress the expression of a translated product and/or transcript of the Neph3 gene are candidate compounds for eliminating the characteristics of pancreatic progenitor cells. The present invention also relates to screening methods that additionally comprise the steps of:

(c) selecting a compound that increases or decreases the expression level of a translated product and/or transcript of the Neph3 gene as compared to detection in the absence of the test sample.

The expression of a translated product and/or transcript of the Neph3 gene can be detected according to the description herein. In step (b) described above, detection can be carried out, for example, by detecting the translated product and/or transcript of the Neph3 gene, as well as measuring the Neph3 promoter activity. Polynucleotides and antibodies for use in detecting the translated product and/or transcript of the Neph3 gene can be prepared and used according to the description herein.

The assay or screening methods that use the Neph3 gene promoter include, for example, methods comprising the steps of:

(a) contacting a test sample with pancreatic progenitor cells or cells that can differentiate into pancreatic progenitor cells, which comprise a nucleic acid in which a heterologous gene is linked under the control of the Neph3 gene promoter; and (b) detecting the expression of a translated product and/or transcript of the heterologous gene in the cells.

For heterologous genes, it is possible to use genes heterologous to the promoter, specifically for example, desired genes (other than the Neph3 gene) linked to the Neph3 gene promoter in the natural state. The genes are, for example, preferably those that can easily detect expression, and specifically include GFP, luciferase, and other marker genes, and genes encoding a differentiation factor or such. Compounds that induce or increase the Neph3 gene promoter activity are candidate compounds for inducing the differentiation of pancreatic progenitor cells, while compounds that decrease or suppress the expression of a translated product and/or transcript of the Neph3 gene are candidate compounds for eliminating the characteristics of pancreatic progenitor cells. The screening methods may additionally comprise the step of:

(c) selecting a compound that increases or decreases the expression of a translated product and/or transcript of the heterologous gene as compared to detection in the absence of the test sample.

Herein, the "test sample" may be samples comprising any compound, and include, for example, the expression products of gene libraries, synthetic low-molecular-weight compound libraries, synthetic peptide libraries, antibodies, substances released by bacteria, cell (microbial, plant cell, or animal cell) extracts, cell (microbial, plant cell, or animal cell) culture supernatants, purified or partially purified polypeptides, marine organisms, extracts derived from plant, animal or such, soil, random phage peptide display libraries. Meanwhile, cells capable of differentiating into pancreatic progenitor cells include preferably multipotent cells, and specifically include ES cells, multipotent stem cells including induced multipotent stem cells, embryo-derived or artificial undifferentiated endodermal cells, and cells differentiated from these cells (Kubo A et al., Development (2004) 131: 1651-1662; Tada S et al., Development (2005) 132: 4363-4374; Yasunaga M et al., Nat Biotechnol (2005) 23: 1542-1550; Gadue P et al., Proc Natl Acad Sci USA (2006) 103: 16806-16811; D'Amour K A et al., Nat Biotechnol (2005) 23: 1534-1541; McLean A B et al., STEM CELLS (2007) 25: 29-38; D'Amour K A et al., Nat Biotechnol (2006) 24: 1392-1401; Shiraki, N. et al., Stem Cells (2008) 26: 874-885).

Cell growth and differentiation can be detected by comparing the cell condition with when the test sample is not contacted. Cell growth and differentiation can be assessed through morphological observation under a microscope, or detecting or quantifying substances produced upon cell differentiation.

Cell differentiation can be assessed by comparing the expression level of a translated product and/or transcript of the Neph3 gene in the absence of a test sample. More specifically, when a test sample induces the expression of a translated product and/or transcript of the Neph3 gene or increases the expression level as compared to detection in the absence of the test sample, it can be judged that the test sample has the ability of inducing differentiation into pancreatic progenitor cells. Herein, "increase" means, for example, 1.2 times or more, preferably twice, five times, or ten times or more. Compounds isolated by the screening are useful as agents for regulating the differentiation of pancreatic progenitor cells, and are expected to be applicable to treatment of pancreatic disease, in particular, pancreatic regenerative medicine.

EXAMPLES

Hereinbelow, the present invention will be specifically described using the Examples, but it is not to be construed as being limited thereto. All prior art documents cited herein are incorporated herein by reference.

Example 1

Analysis of Neph3 Expression in Fetal Pancreatic Primordium

At fetal stages, Neph3 is expressed in dopamine-neuron progenitor cells in the central nervous system (WO 2004/038018) and GABA-producing neuron progenitor cells in spinal cord and cerebellum (WO 2008/096817). However, it remains unknown whether Neph3 is expressed during development and differentiation other than in the central nervous system. In this context, the present inventors undertook an attempt to identify Neph3-expressing cells during embryonic development other than in the central nervous system. First, Neph3 was closely analyzed for its expression in E12.5 mouse embryos using the method described in WO 2004/038018. The result showed that Neph3 was expressed in the pancreatic primordium (FIG. 1A). Neph3 was found to be expressed selectively in a fraction of the cells in the pancreatic primordium (FIG. 1B).

Figure 2:
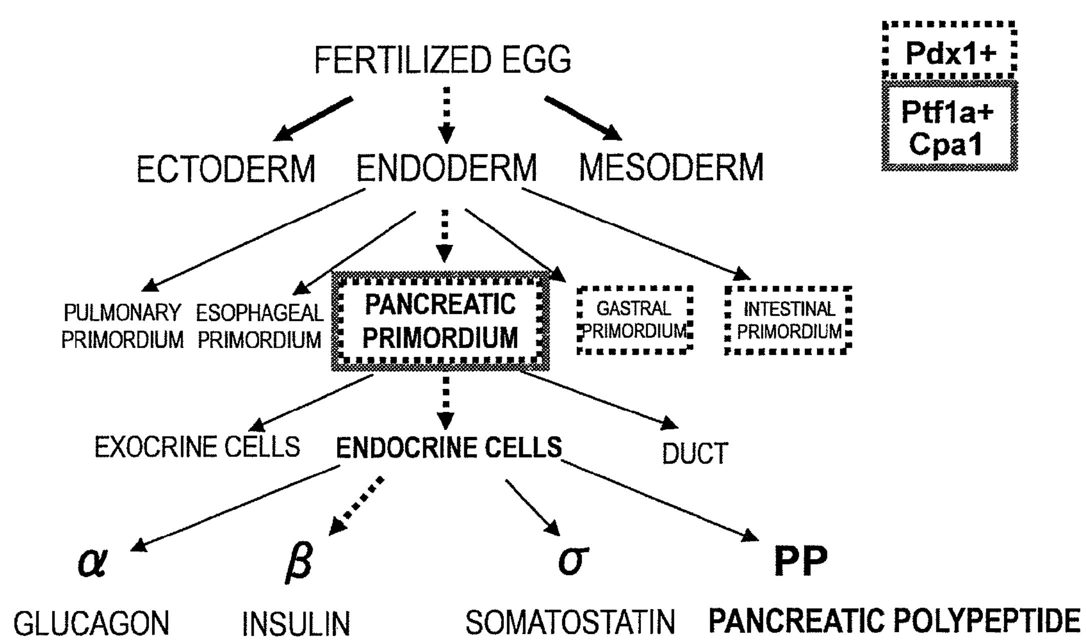
FIG. 2 shows a flow chart of the course of pancreatic development.

The pancreatic primordium produces exocrine cells that secrete digestive enzymes and the like, duct cells that convey these digestive enzymes to the duodenum, and endocrine cells that secrete various hormones such as insulin to the blood stream (FIG. 2). It is known that E12.5 mouse pancreatic primordium contains multipotent progenitor cells which have the ability to differentiate into the above-described three types of cells and progenitor cells that have a committed differentiation fate. Thus, the type of Neph3-positive cells in the pancreatic primordium was identified by the method described below. E12.5 mouse embryos were excised and fixed with 4% PFA/PBS(−) at 4° C. for two hours. Then, the solution was replaced with 20% sucrose/PBS(−) at 4° C. overnight. The embryos were embedded in OCT. After 12 μm-thick sections were prepared and attached to glass slides, they were dried at room temperature for 20 minutes and wetted with 0.1% TritonX-100/PBS(−) for five minutes. Then, the sections were blocked with 25% BlockAce for 30 minutes, and reacted with a primary antibody (in 0.1% TritonX-100/2.5% BlockAce/PBS(−)) at room temperature for two hours. The glass slides were washed twice with 0.1% TrironX-100/PBS(−) for ten minutes. Next, the sections were reacted with a fluorescently-labeled secondary antibody (in 0.1% TritonX-100/2.5% BlockAce/PBS(−)) at room temperature for 40 minutes. The sections were washed in the same way as described above and mounted on the glass slides. The following primary antibodies are used: Neph3 as described in WO 2004/038018 and Minaki Y. et al., Neurosci. Res. (2005) 52(3): 250-262; Ptf1a as described in Minaki Y. et al., Gene Expr. Patterns, (2008) 8(6): 418-423; and Pdx1 purchased from Abcam Co.

Figure 3:
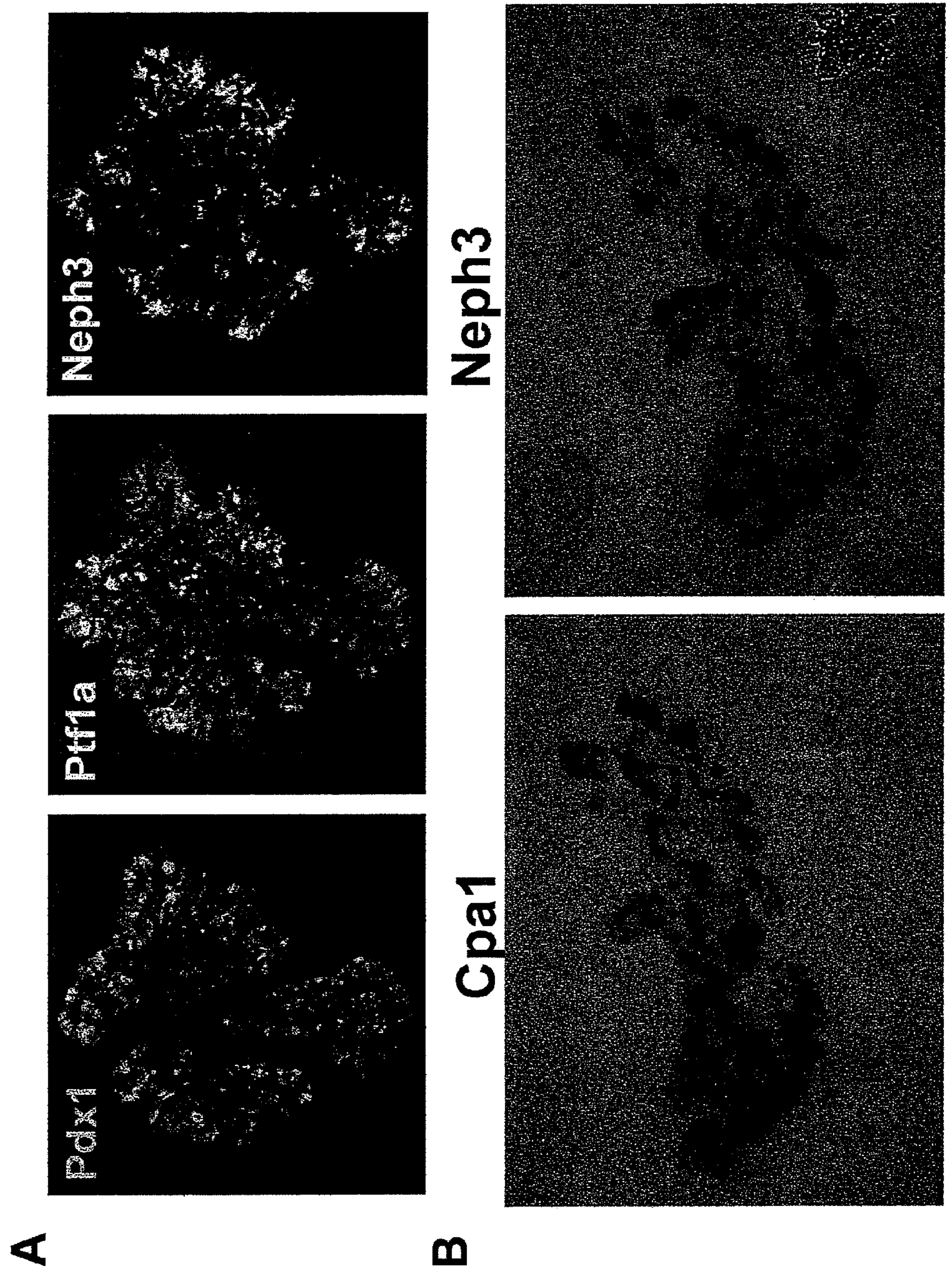
FIG. 3 shows in photographs a comparison of the expressions of Neph3, Pdx1, Ptf1a, and Cpa1 in the pancreatic primordium. A: antibody staining; B: in situ hybridization.

The result revealed that Neph3 was expressed in cells positive for Pdx1 and Ptf1a, which are factors that play important roles in the development of multipotent pancreatic progenitor cells (FIG. 3). It was also revealed that the expression pattern of Neph3 was the same as that of Cpa1, which is a multipotent pancreatic progenitor cell marker. These findings suggest that Neph3 is expressed in pancreatic multipotent progenitor cells.

Example 2

Identification and Isolation of Neph3-Positive Cells in Fetal Pancreatic Primordium To assess Neph3 expression in pancreatic multipotent progenitor cells, Neph3-positive cells were isolated according to the protocol described below and the cell type was identified. Pancreases were excised from E12.5 mouse embryos. The cells were dispersed in cell dispersion buffer AccuMax™ (Innovative Cell Technologies), and blocked with mouse FC-Block (BD) at 4° C. for ten minutes without fixation and permeation treatment. Then, the cells were stained with an anti-Neph3 monoclonal antibody (purified antibody (100 times diluted) in D-MEM/F12 medium containing 1% fetal calf serum and 1 mM EDTA) at 4° C., for 30 minutes. After washing three times with D-MEM/F 12 containing 1% fetal calf serum and 1 mM EDTA at 4° C. for 3 minutes, the cells were stained with a PE-labeled anti-hamster IgG antibody (BD, 8 μg/ml, in D-MEM/F 12 medium containing 1% fetal calf serum and 1 mM EDTA) at 4° C. for 30 minutes and washed in the same way as described above. After staining, Neph3-expressing cells were isolated using a cell sorter. The isolated cells were centrifuged at 1,000 rpm at 4° C. for ten minutes. After the supernatant was removed, the cells were spotted onto 8-well chamber glass slides (Nunc) coated with poly-L-ornithine (Sigma; 0.002% in PBS), laminin (Invitrogen; 2.5 μg/ml in PBS), and fibronectin (Sigma; 5 μg/ml in PBS). The glass slides were allowed to stand for 15 minutes to attach the cells to the slides. Then, the cells were incubated in DMEM/F12 medium containing N2 (1×; Invitrogen) and B27 (Invitrogen; 1×) at 37° C. for one hour. The culture medium was removed and the cells were washed once with 500 μl of PBS(−) at room temperature. The cells were fixed with 2% PFA/PBS(−) for 30 minutes, and permeabilized with 0.3% TrintonX-100/PBS(−) at room temperature for 30 minutes. Then, after the glass slides were blocked with 25% BlockAce at room temperature for 30 minutes, a primary antibody (in 0.1% TritonX-100/2.5% BlockAce/PBS(−)) was reacted at room temperature for two hours. After washing twice with 0.1% TrironX-100/PBS(−) for ten minutes, the cells were reacted with a fluorescently-labeled secondary antibody (in 0.1% TritonX-100/2.5% BlockAce/PBS(−)) at room temperature for 40 minutes. After washing in the same way as described above, the cell nuclei were stained. The primary antibodies against Pdx1 and Ptf1a are described in Example 1. SYTOX nucleic acid stain (Molecular probes; 100,000 times diluted) was used for nuclear staining.

Figure 4:
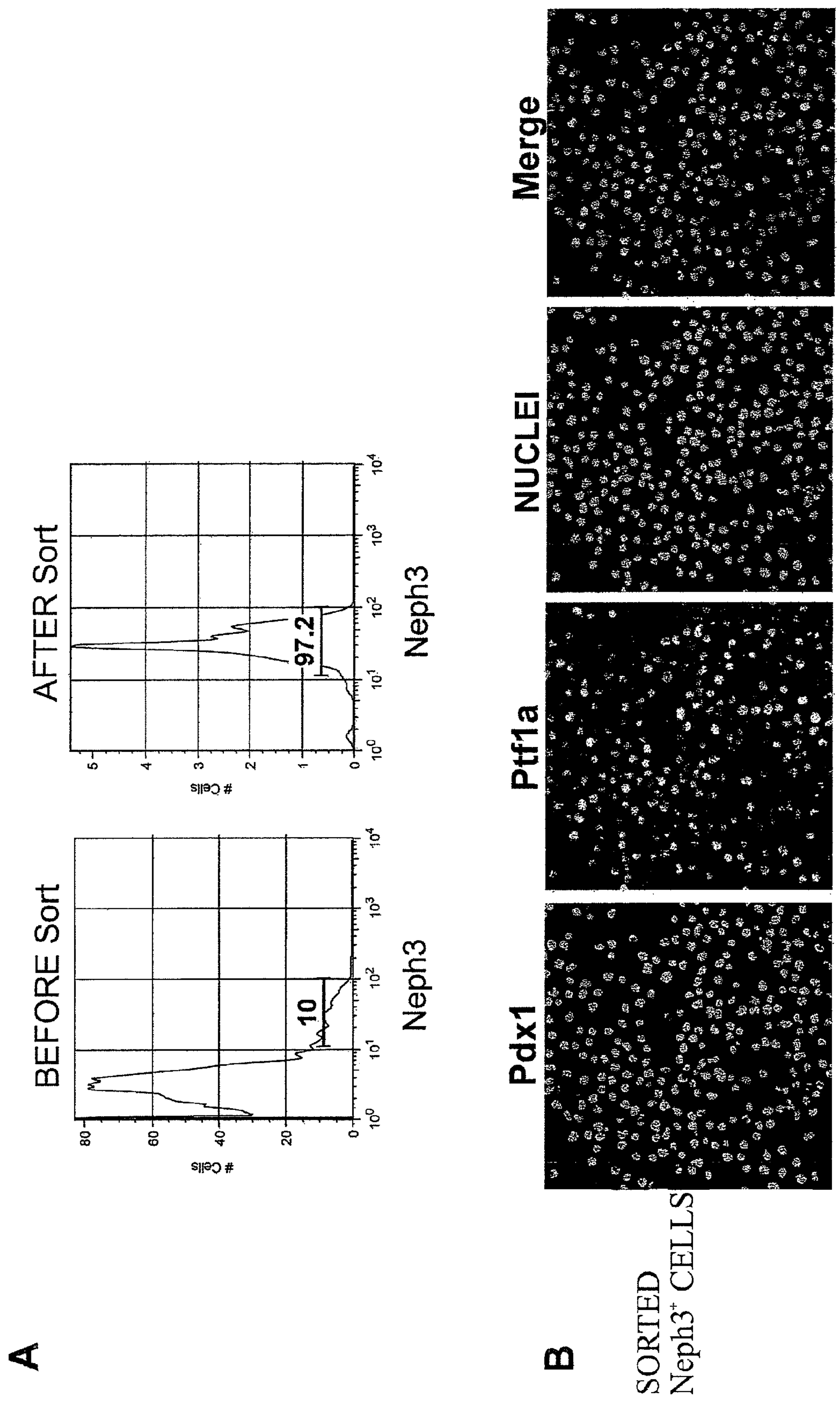
FIG. 4 shows in graphs and photographs that pancreatic multipotent progenitor cells can be isolated from fetal mice by using an anti-Neph3 antibody. A: FACS of fetal mouse pancreas using an anti-Neph3 antibody; B: antibody staining of isolated Neph3-positive cells.

As a result, Neph3 expression was confirmed on the cell surface of a fraction of the pancreatic progenitor cells and isolation of Neph3-positive cells was revealed (FIG. 4A). Furthermore, the isolated Neph3-positive cells were positive for both Pdx1 and Ptf1a. Thus, it was confirmed that Neph3 was expressed in pancreatic multipotent progenitor cells (FIG. 4B). More specifically, it was demonstrated that pancreatic multipotent progenitor cells can be isolated by using an anti-Neph3 antibody.

Example 3

Expression of Foreign Genes Using the Neph3 Promoter Specifically in Pancreatic Progenitor Cells Next, whether foreign genes can be expressed in a pancreatic progenitor cell-specific manner using the Neph3 promoter was assessed by creating transgenic mice and analyzing the expression of foreign genes according to the protocol described below.

First, the poly A addition sequence of bovine growth hormone (SEQ ID NO: 23; derived from Invitrogen pcDNA3.1+ vector) was amplified and inserted into the HindIII/XhoI site of pSP73 (Promega) to construct pSP73-polyA. Then, the synthetic DNAs of SEQ ID NOs: 24 and 25 were annealed to each other and inserted into the Asp718I/BamHI site of pSP73-polyA to construct pSP73-polyA II. A mouse genomic fragment located about 3.2 kb upstream of the translation initiation codon of Neph3 (SEQ ID NO: 26) was inserted into the ClaI/Asp718I site of pSP73-polyA II to construct pN3. Finally, GFP cDNA (SEQ ID NO: 27) was inserted as a foreign gene into the Asp718I/SalI site of pN3 to construct pN3-GFP. After linearized with ClaI, pN3-GFP was injected into the pronuclei of mouse fertilized eggs according to the method of Gordon et al. (Gordon J W et al., Proc Natl Acad Sci USA (1980) 77(12): 7380-7384), and the eggs were transplanted into foster mothers. The fetuses were recovered at embryonic day 12.5, and the expression of Neph3 and GFP mRNAs in the pancreatic primordia was analyzed by the methods described in Example 1.

Figure 5:
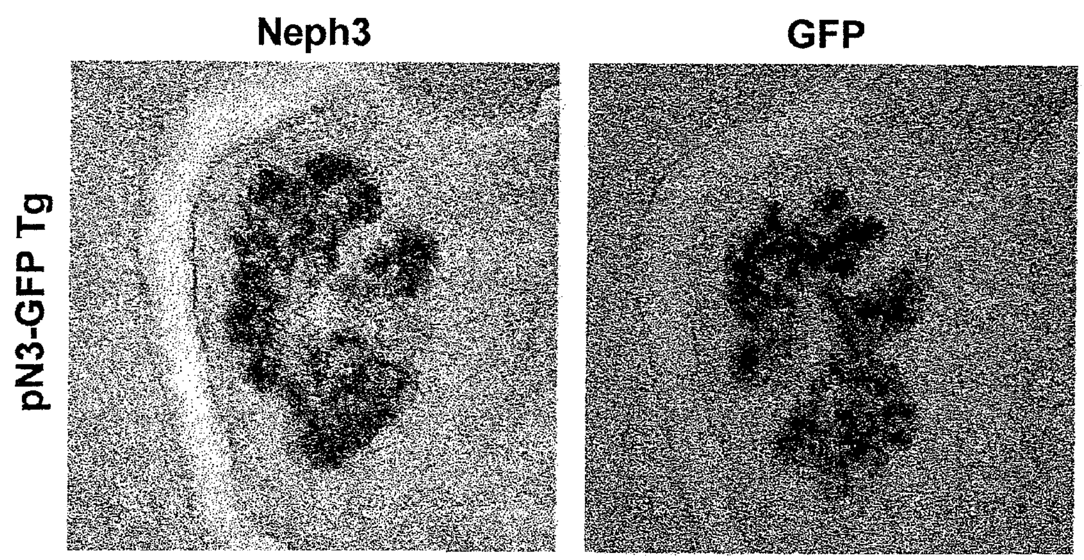
FIG. 5 shows in photographs that a foreign gene (GFP) can be specifically expressed in pancreatic progenitor cells by using a Neph3 promoter.

The result showed that the transgenic mice expressed GFP specifically in the entire Neph3-positive area (FIG. 5). This finding demonstrates that foreign genes can be expressed in a pancreatic progenitor cell-specific manner by using the Neph3 promoter.

Example 4

Pancreatic Progenitor Cell-Specific Activation of Human Neph3 Promoter

Next, whether the human Neph3 promoter is activated in a manner specific to pancreatic progenitor cell was assessed to confirm that Neph3 is also specifically expressed in human pancreatic progenitor cells. The foreign gene expression was analyzed using transgenic mice prepared according to the protocol described below.

First, a fragment of the mouse Neph3 promoter was deleted by digestion with ClaI/Asp718I from pN3-GFP described in Example 3. Then, a human genomic fragment located about 2.1 kb upstream of the translation initiation codon of Neph3 (SEQ ID NO: 27) was inserted into the same site to construct phsN3-GFP. After phsN3-GFP was linearized with ClaI and injected into the pronuclei of mouse fertilized eggs according to the method of Gordon et al. (supra), the eggs were transplanted into foster mothers. The fetuses were recovered at embryonic day 12.5, and the expression of Neph3 and GFP mRNAs in the pancreatic primordium was analyzed by the methods described in Example 3.

Figure 6:
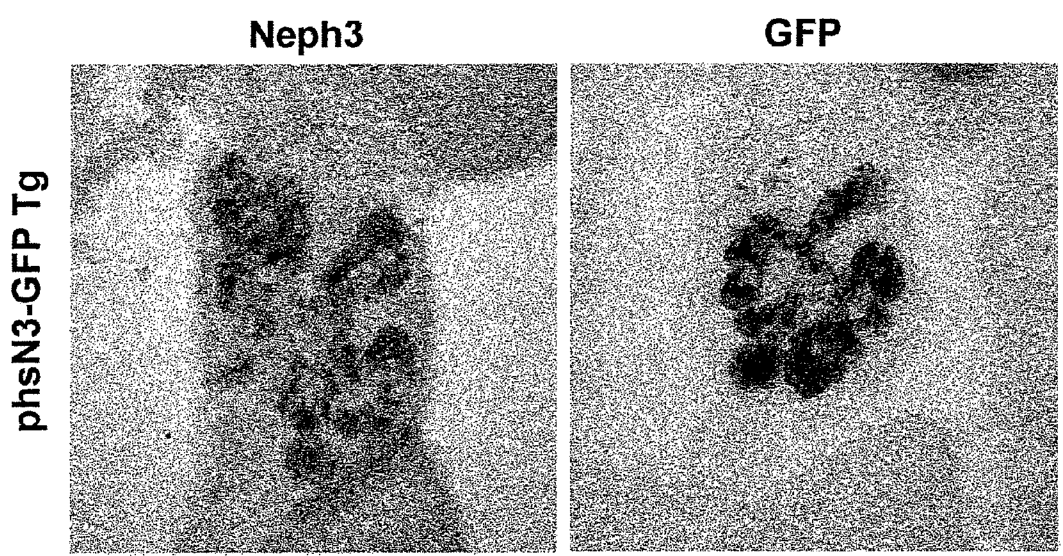
FIG. 6 shows in photographs that a human Neph3 promoter is activated in a manner specific to pancreatic progenitor cells.

The result showed that the transgenic mice expressed GFP specifically in the entire Neph3-positive area (FIG. 6). This finding demonstrates that the human Neph3 promoter was activated in a pancreatic progenitor cell-specific manner. This suggests that as in mice, human Neph3 is specifically expressed in pancreatic progenitor cells.

Industrial Applicability

Selection markers for pancreatic progenitor cells are identified by the present invention. Thus, pancreatic progenitor cells can be detected, distinguished, identified, collected, prepared, selected, enriched, isolated, and/or obtained by using the marker as an indicator. The present invention also enables collection, enrichment, isolation, and/or obtainment, or the like of viable pancreatic progenitor cells without using the translated product or transcript of any foreign gene. Thus, the present invention is very useful in preparing materials for transplantation therapy for pancreatic diseases including diabetes, and searching for genes that regulate pancreatic development and differentiation, as well as in drug discovery that targets pancreatic progenitor cells and others.

The invention claimed is:

1. A method for isolating Nephrin-like 3 (Neph3)-expressing pancreatic progenitor cells, comprising:

(a) identifying the expression of Neph3 in cells of an endodermal cell sample, wherein the cells expressing Neph3 are pancreatic progenitor cells; and (b) isolating the cells expressing Neph3 from the endodermal cell sample.

2. The method of claim 1, wherein the endodermal cell sample is a central nervous system lineage cell-depleted cell sample.

3. The method of claim 1, wherein the endodermal cell sample is an abdomen-derived cell sample.

4. The method of claim 1, further comprising identifying the expression of any one or a combination of genes selected from the group consisting of pancreatic and duodenal homeobox factor-1 (Pdx-1), pancreas specific transcription factor-1a (Ptf1a), carboxypeptidase A1 (pancreatic) (Cpa1), and epiplakin 1 (EPPK1).

5. The method of claim 1, further comprising identifying the expression of the genes pancreatic and duodenal homeobox factor-1 (Pdx-1) and carboxypeptidase A1 (pancreatic) (Cpa1).

6. The method of claim 1, wherein isolating the cells expressing Neph3 from the endodermal cell sample is achieved by using an immunochemical method.

7. A method for, detecting a pancreatic progenitor cell, which comprises identifying the expression of a translated product of a Neph3 gene in an endodermal cell sample.

8. The method of claim 7, wherein the endodermal cell sample is a central nervous system lineage cell-depleted cell sample.

9. The method of claim 7, wherein the endodermal cell sample is an abdomen-derived cell sample.

10. The method of claim 7, further comprising identifying the expression of any one or a combination of genes selected from the group consisting of pancreatic and duodenal homeobox factor-1 (Pdx-1), pancreas specific transcription factor-1a (Ptf1a), carboxypeptidase A1 (pancreatic) (Cpa1), and epiplakin 1 (EPPK1).

11. The method of claim 10, wherein the combination consists of pancreatic and duodenal homeobox factor-1 (Pdx-1) and carboxypeptidase A1 (pancreatic) (Cpa1).

12. The method of claim 7, wherein the method for detecting a pancreatic progenitor cell is an immunochemical method.

13. The method of claim 2, further comprising identifying the expression of any one or a combination of genes selected from the group consisting of pancreatic and duodenal homeobox factor-1 (Pdx-1), pancreas specific transcription factor-1a (Ptf1a), carboxypeptidase A1 (pancreatic) (Cpa1), and epiplakin 1 (EPPK1).

14. The method of claim 3, further comprising identifying the expression of any one or a combination of genes selected from the group consisting of pancreatic and duodenal homeobox factor-1 (Pdx-1), pancreas specific transcription factor-1a (Ptf1a), carboxypeptidase A1 (pancreatic) (Cpa1), and epiplakin 1 (EPPK1).

15. The method of claim 1, wherein the endodermal cell sample is a human endodermal cell sample and identifying the expression of Neph3 in cells of the endodermal cell sample is achieved by detecting a Neph3 translated product.

16. The method of claim 1, wherein the endodermal cell sample is a murine endodermal cell sample and identifying the expression of Neph3 in cells of the endodermal cell sample is achieved by detecting a Neph3 translated product.

17. A method for isolating Neph3-expressing pancreatic progenitor cells, comprising:

(a) contacting an endodermal cell sample with an anti-Neph3 antibody, wherein the cells bound by the anti-Neph3 antibody are pancreatic progenitor cells; and (b) isolating the cells bound by the anti-Neph3 antibody from the endodermal cell sample.

18. The method of claim 17, wherein the endodermal cell sample is a human endodermal cell sample and the anti-Neph3 antibody binds to the human Neph3 protein of SEQ ID NO:10, SEQ ID NO:12, SEQ ID NO:14, SEQ ID NO:16, SEQ ID NO:18, SEQ ID NO:20, or SEQ ID NO:22.

19. The method of claim 18, wherein the cells bound by the anti-Neph3 antibody are isolated using flow cytometry or antibody-immobilized beads.

20. The method of claim 18, wherein the endodermal cell sample is a central nervous system lineage cell-depleted cell sample.

21. The method of claim 17, wherein the endodermal cell sample is a murine endodermal cell sample and the anti-Neph3 antibody binds to the murine Neph3 protein of SEQ ID NO:2, SEQ ID NO:4, SEQ ID NO:6, or SEQ ID NO:8.

22. The method of claim 21, wherein the cells bound by the anti-Neph3 antibody are isolated using flow cytometry or antibody-immobilized beads.

23. The method of claim 21, wherein the endodermal cell sample is a central nervous system lineage cell-depleted cell sample.

* * * * *